(12) United States Patent
Foerster et al.

(10) Patent No.: US 11,096,682 B2
(45) Date of Patent: *Aug. 24, 2021

(54) SURGICAL INSTRUMENT FOR MANIPULATING AND PASSING SUTURE

(71) Applicant: ArthroCare Corporation, Austin, TX (US)

(72) Inventors: Seth A. Foerster, San Clemente, CA (US); Thomas Weisel, Ventura, CA (US); Roger Pisarnwongs, Valencia, CA (US)

(73) Assignee: ArthroCare Corporation, Austin, TX (US)

( * ) Notice: Subject to any disclaimer, the term of this patent is extended or adjusted under 35 U.S.C. 154(b) by 109 days.

This patent is subject to a terminal disclaimer.

(21) Appl. No.: 16/278,590

(22) Filed: Feb. 18, 2019

(65) Prior Publication Data

US 2019/0175166 A1    Jun. 13, 2019

Related U.S. Application Data

(63) Continuation of application No. 14/193,069, filed on Feb. 28, 2014, now Pat. No. 10,265,062, which is a continuation-in-part of application No. 13/760,163, filed on Feb. 6, 2013, now Pat. No. 9,936,941.

(60) Provisional application No. 61/596,160, filed on Feb. 7, 2012, provisional application No. 61/606,695, filed on Mar. 5, 2012, provisional application No. 61/905,064, filed on Nov. 15, 2013.

(51) Int. Cl.
A61B 17/04    (2006.01)
A61B 17/06    (2006.01)

(52) U.S. Cl.
CPC ...... *A61B 17/0469* (2013.01); *A61B 17/0483* (2013.01); *A61B 17/06109* (2013.01); *A61B 2017/06009* (2013.01); *A61B 2017/06042* (2013.01)

(58) Field of Classification Search
CPC ............ A61B 17/0482; A61B 17/0469; A61B 17/0483; A61B 17/0485; A61B 17/06109
See application file for complete search history.

(56) References Cited

U.S. PATENT DOCUMENTS 5,569,269 A * 10/1996 Hart .................... A61B 17/0469
                                                                      112/169
5,817,111 A * 10/1998 Riza .................... A61B 17/0483
                                                                      606/148

(Continued)

*Primary Examiner* — Alexander J Orkin
(74) *Attorney, Agent, or Firm* — Norman F. Hainer, Jr.

(57) ABSTRACT

A suture manipulating instrument for passing and retrieving suture through a tissue includes a handle mechanism, an elongate shaft extending from the handle, and a working distal end. The working distal end includes a needle body, a lumen defined by the needle body, a tissue penetrating distal tip, and a lateral slot. A preformed inner member is movably disposed within the lumen of the needle. The handle mechanism is used to extend the wire from the lateral slot of the needle, and to retract the wire into the lateral slot, allowing the working end of the instrument to grasp and manipulate suture by pinning and/or trapping the suture against the needle. In embodiments the inner member is further retracted within the needle lumen, drawing a length of suture into the needle lumen. The suture is subsequently ejected from the needle lumen to form a suture loop.

15 Claims, 53 Drawing Sheets

(56) References Cited

U.S. PATENT DOCUMENTS

| | | | |
|---|---|---|---|
| 5,895,395 A * | 4/1999 | Yeung | A61B 17/0469 |
| | | | 606/139 |
| 5,910,148 A * | 6/1999 | Reimels | A61B 17/0483 |
| | | | 606/139 |
| 9,936,941 B2 * | 4/2018 | Weisel | A61B 17/0469 |
| 10,265,062 B2 * | 4/2019 | Foerster | A61B 17/06109 |
| 2007/0142791 A1 * | 6/2007 | Yeung | A61B 17/06066 |
| | | | 604/264 |
| 2008/0154286 A1 * | 6/2008 | Abbott | A61B 17/0487 |
| | | | 606/139 |
| 2009/0228041 A1 * | 9/2009 | Domingo | A61B 17/06066 |
| | | | 606/223 |
| 2012/0209300 A1 * | 8/2012 | Torrie | A61B 17/0469 |
| | | | 606/148 |

* cited by examiner

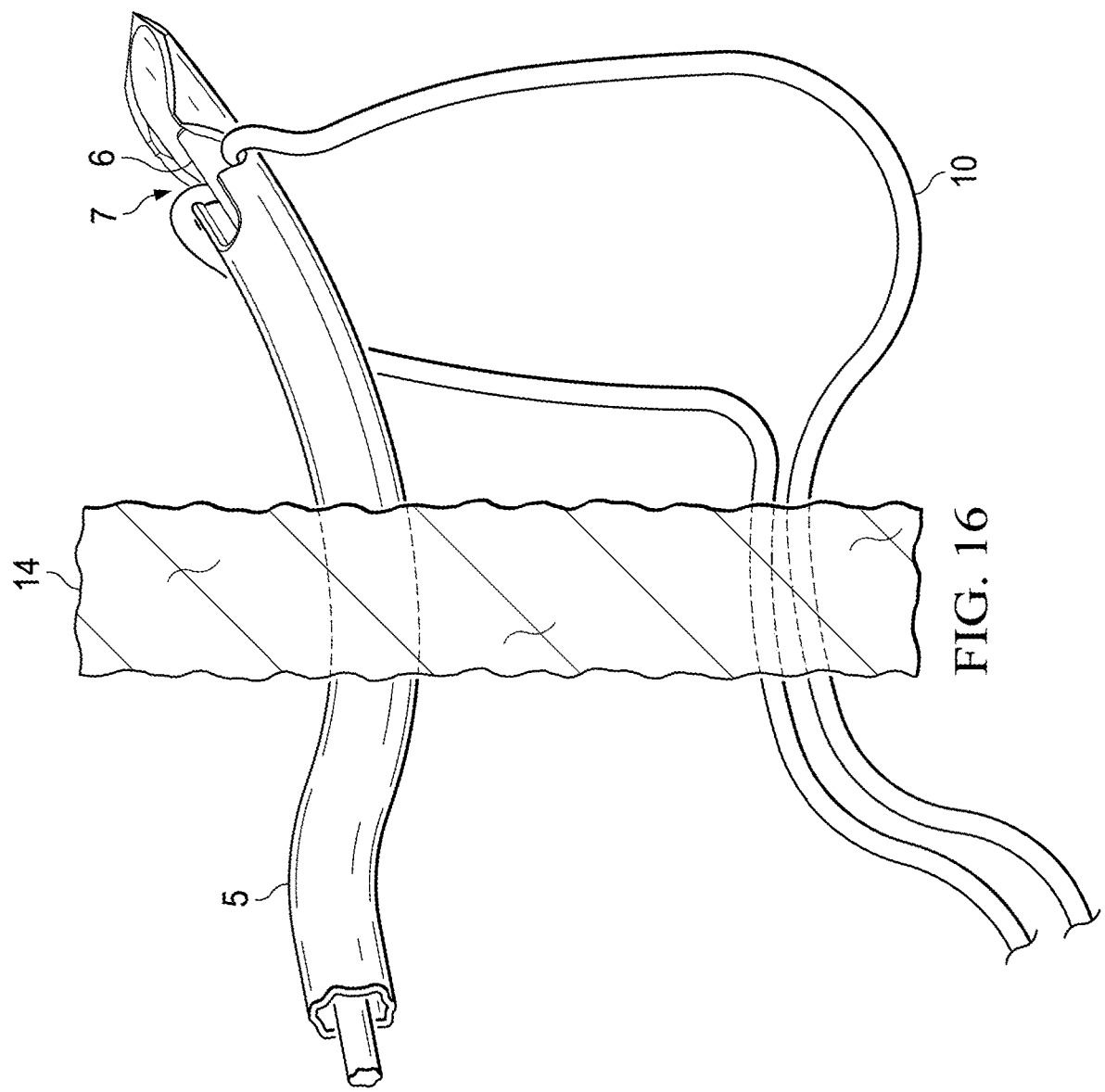

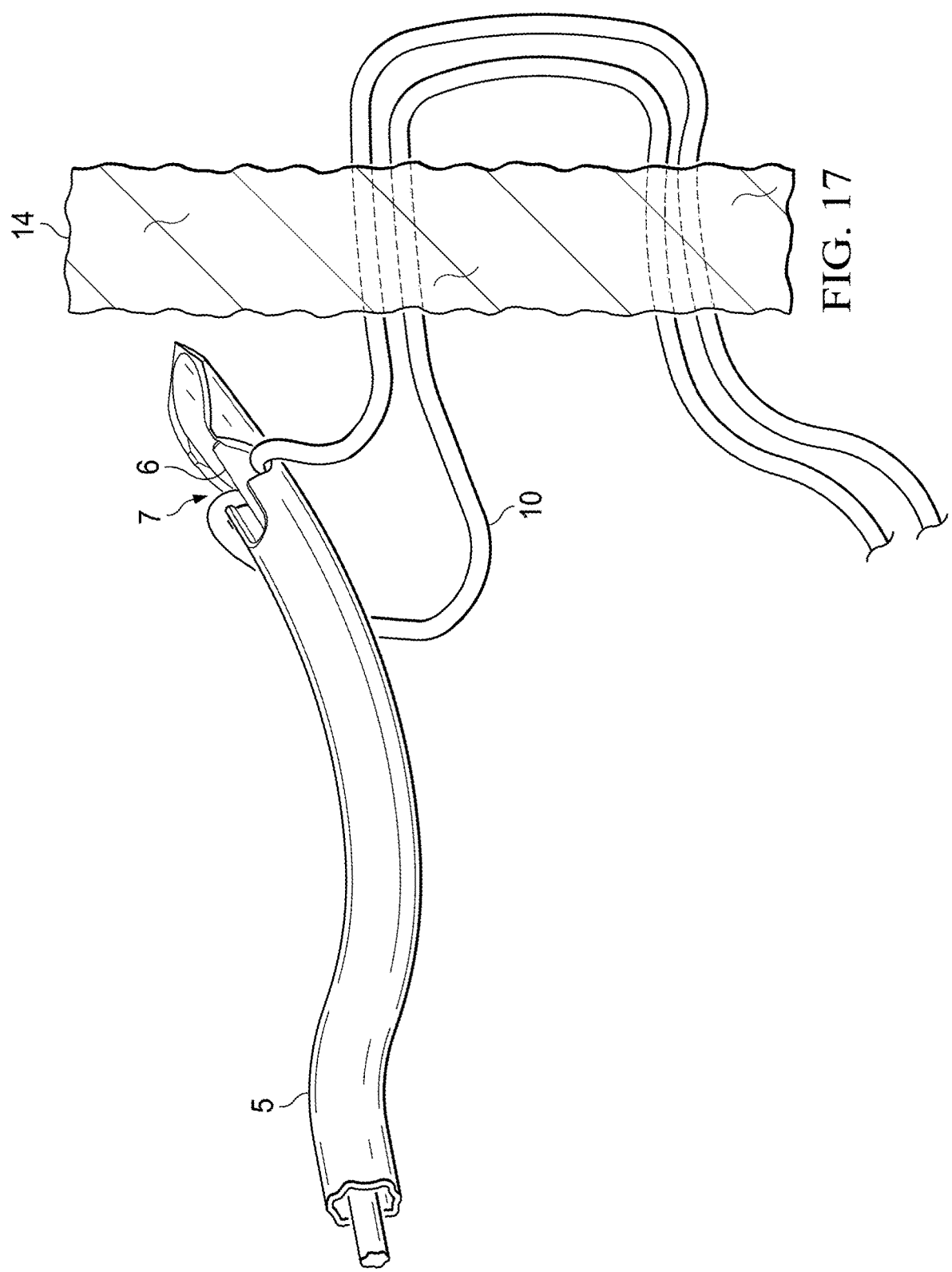

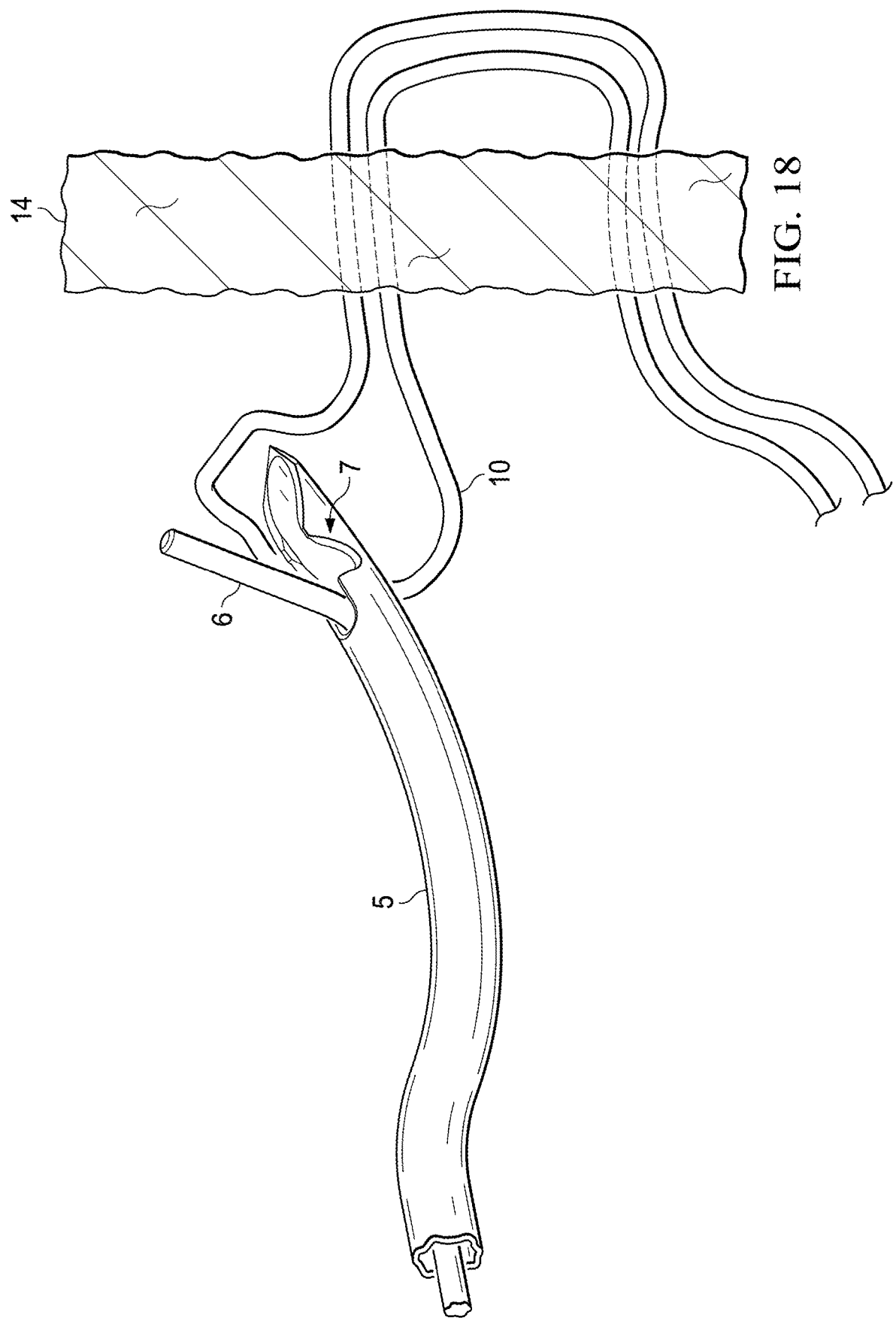

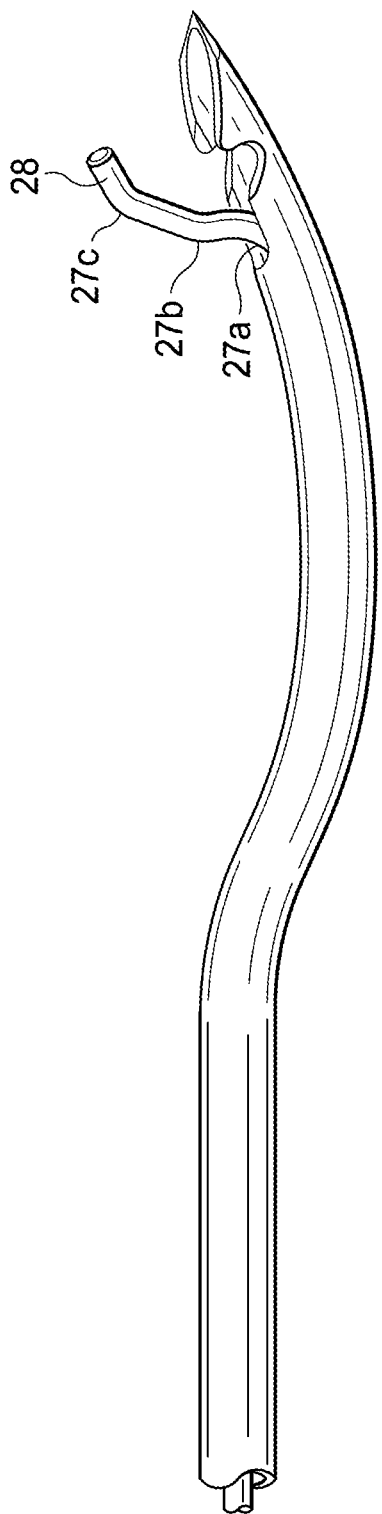
FIG. 27a
FIG. 27b

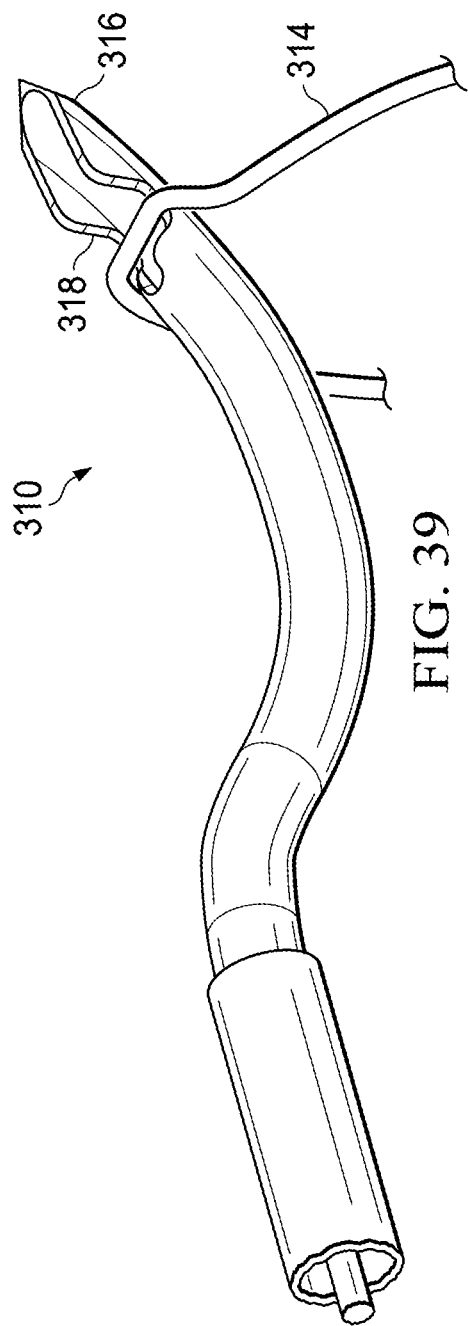
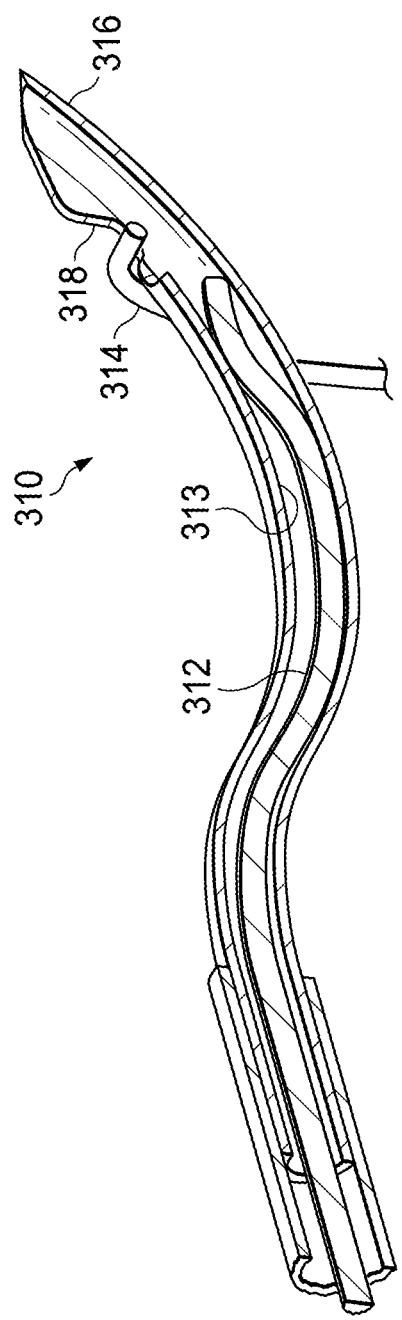

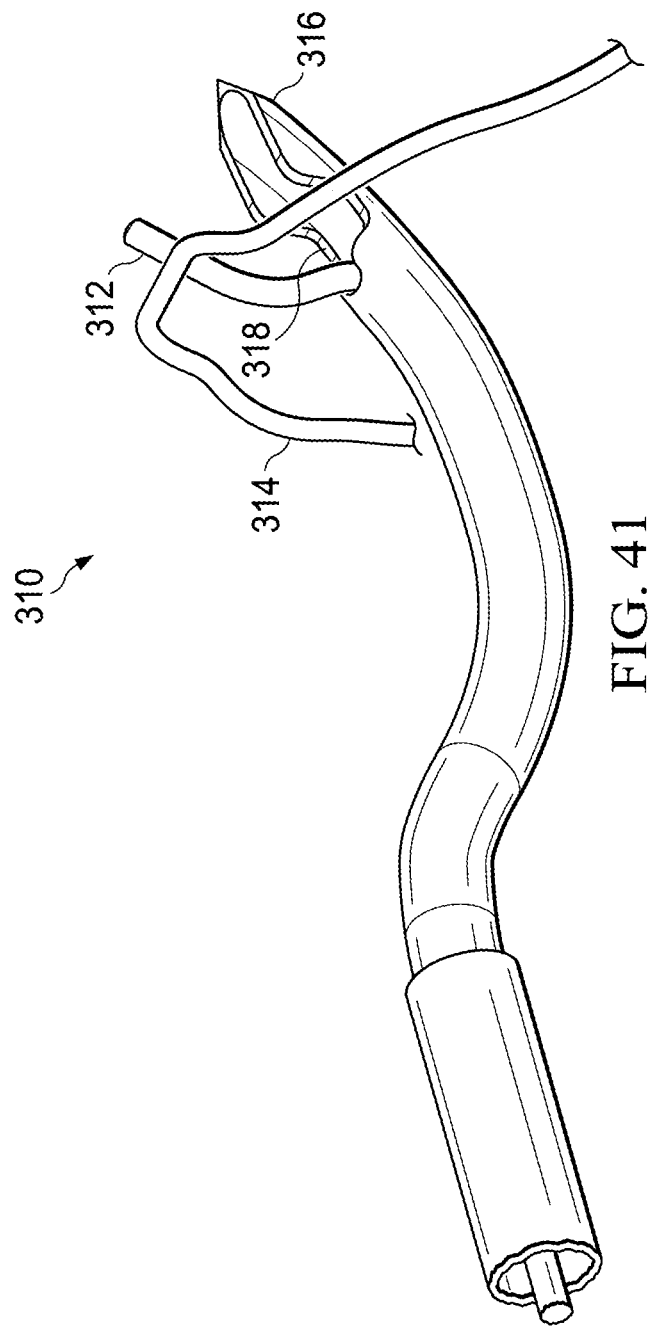

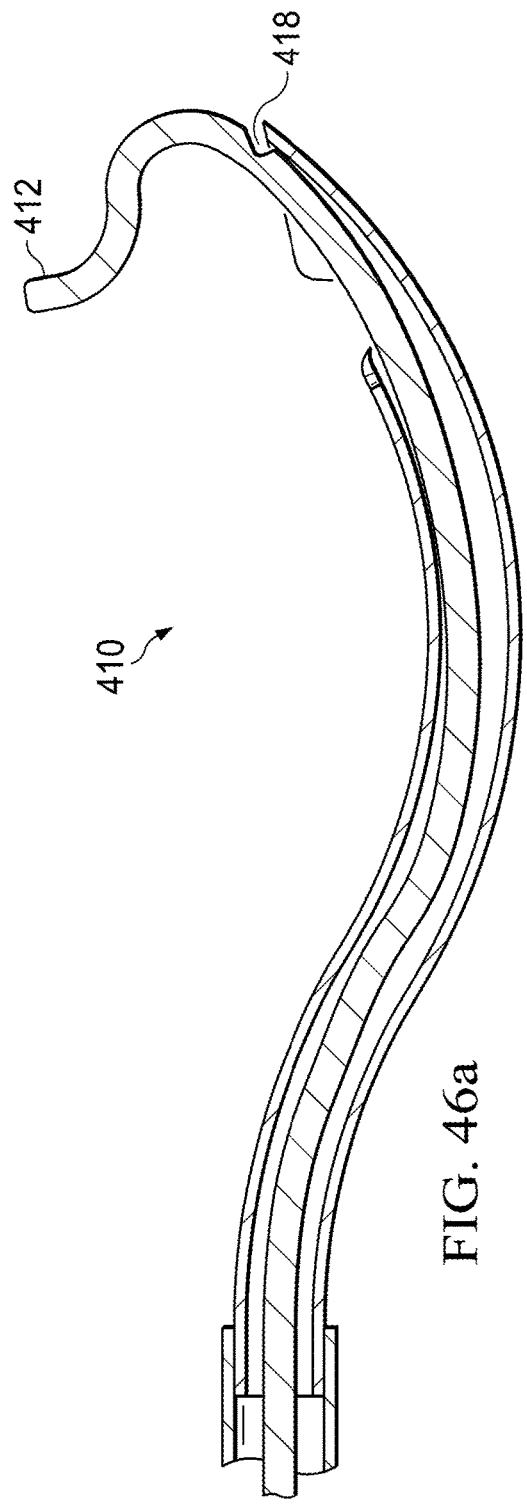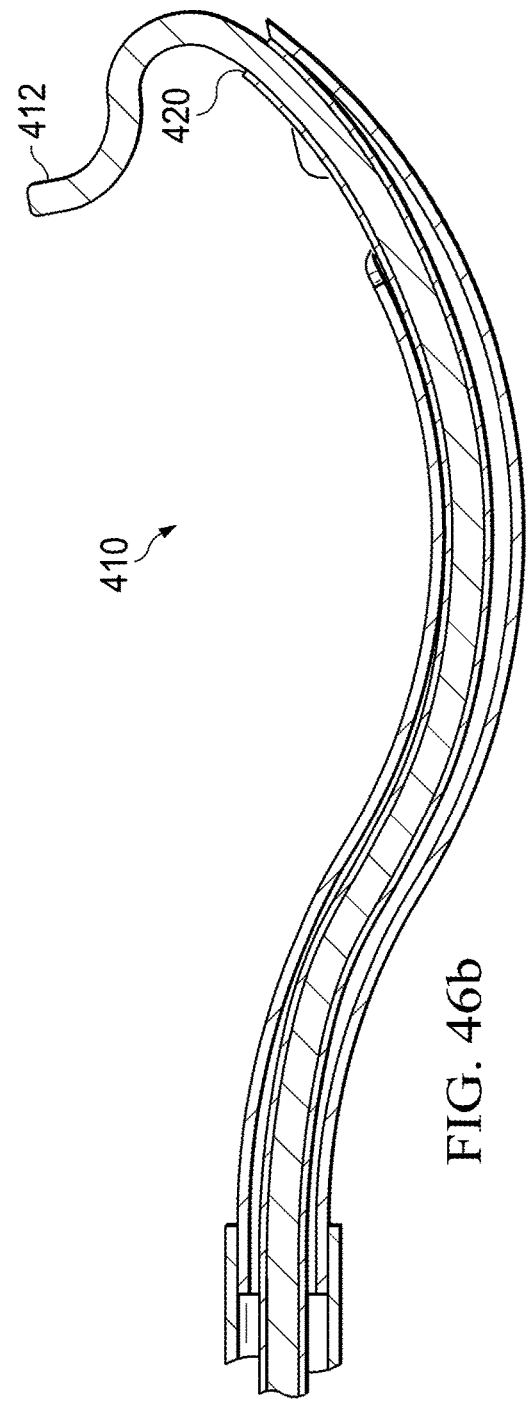
FIG. 46a
FIG. 46b

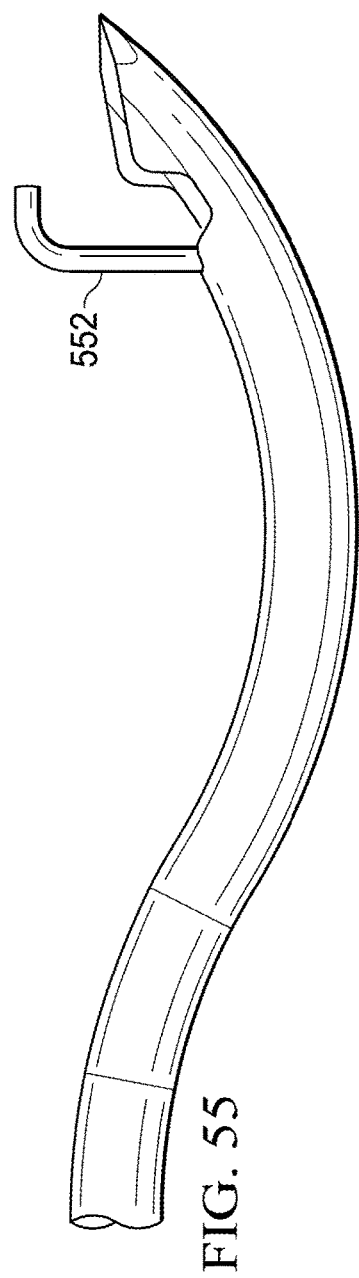
FIG. 55
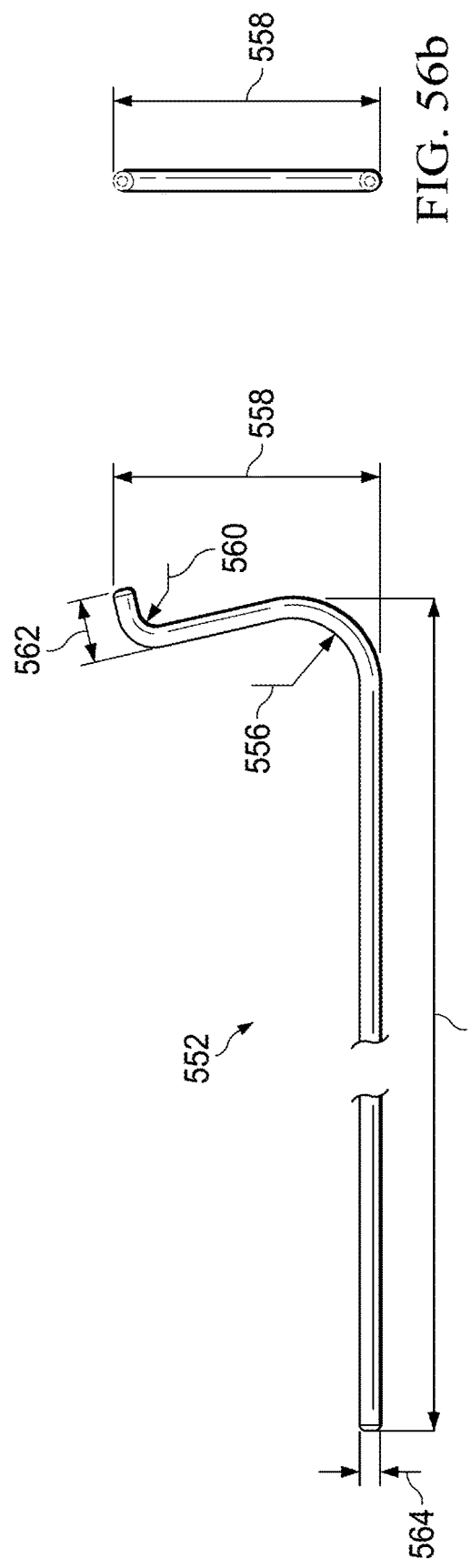
FIG. 56b
FIG. 56a

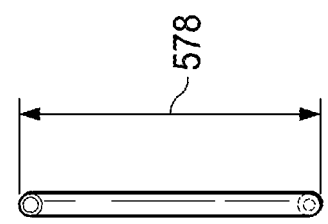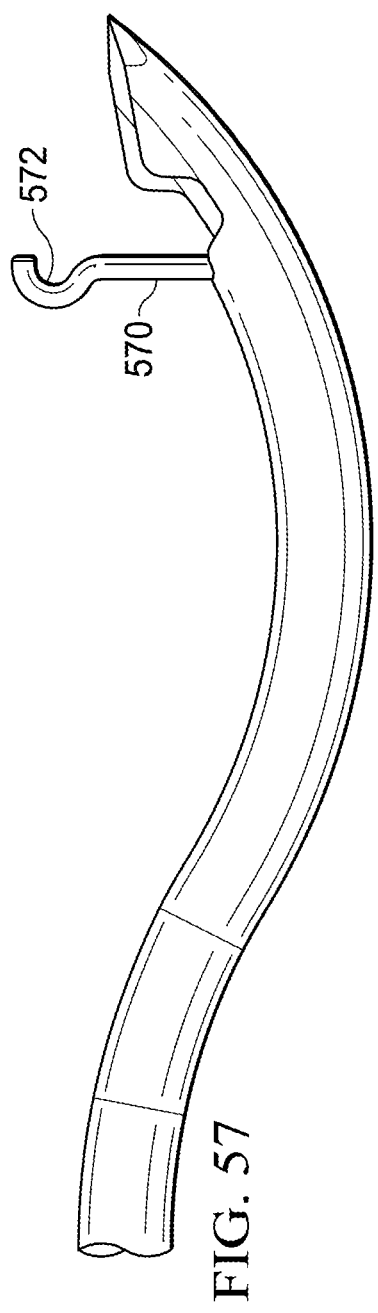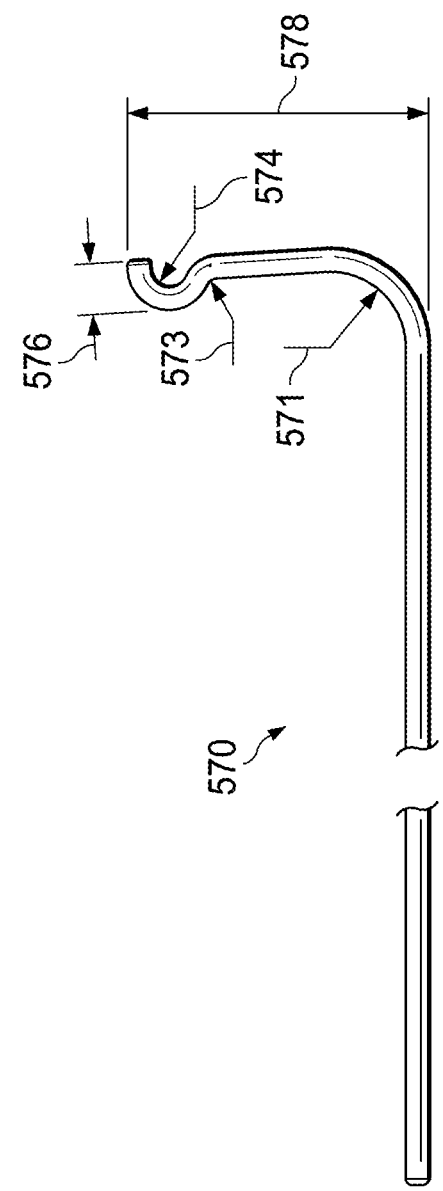

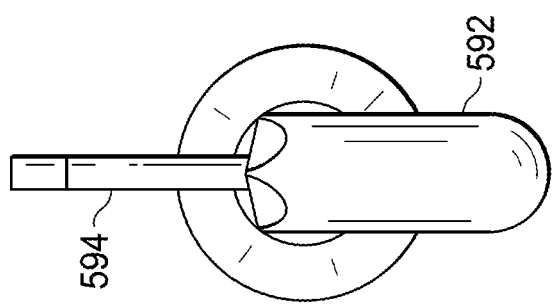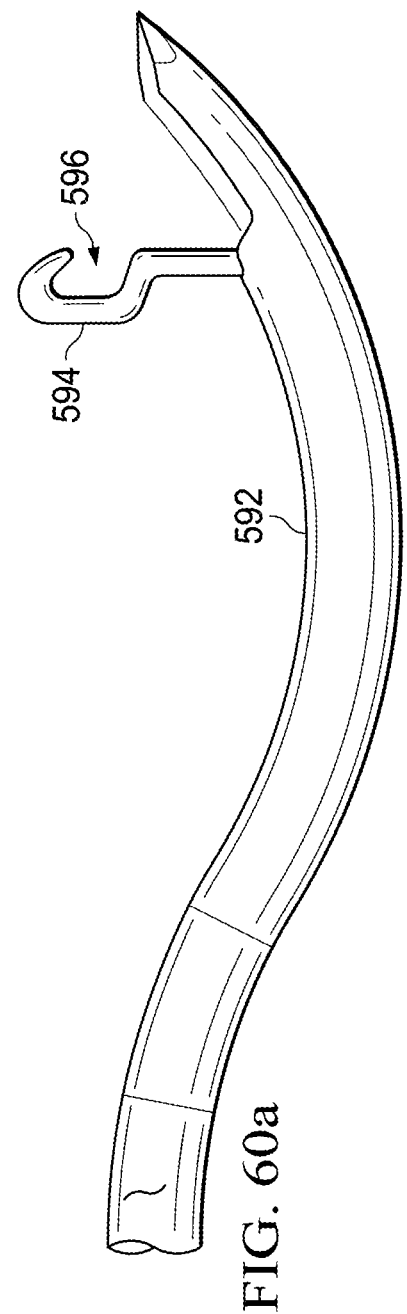
FIG. 60b
FIG. 60a

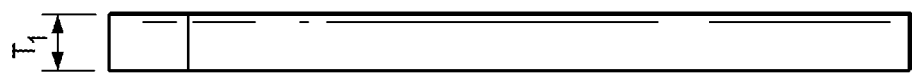
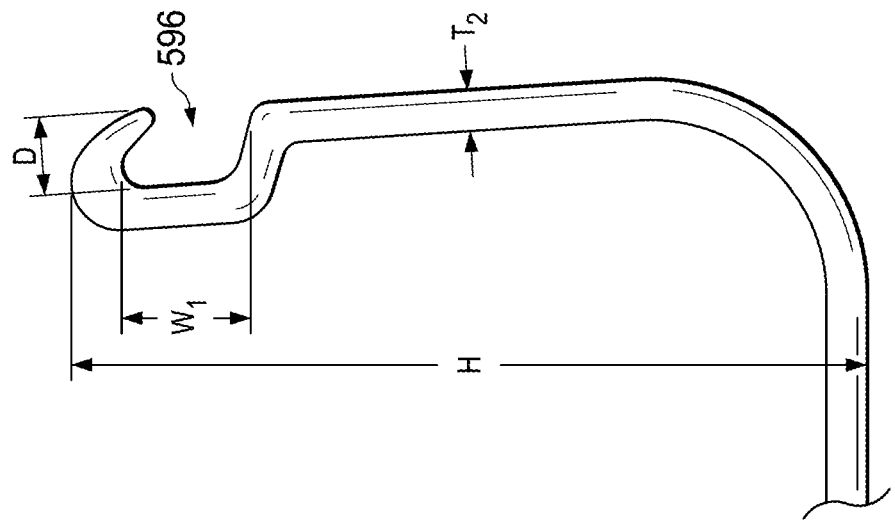
FIG. 60c
FIG. 60d

SURGICAL INSTRUMENT FOR MANIPULATING AND PASSING SUTURE

CROSS REFERENCE TO RELATED APPLICATION

This application is a continuation of U.S. patent application Ser. No. 14/193,069, filed Feb. 28, 2014, which is a continuation-in-part of U.S. patent application Ser. No. 13/760,163, filed Feb. 6, 2013, now U.S. Pat. No. 9,936,941, which claims priority to U.S. provisional application No. 61/596,160, filed Feb. 7, 2012, entitled "Instrument To Manipulate and Pass Suture" and U.S. provisional application No. 61/606,695 filed Mar. 5, 2012, entitled "Instrument To Manipulate and Pass Suture". U.S. patent application Ser. No. 14/193,069 also claims priority to U.S. provisional application No. 61/905,064, filed Nov. 15, 2013, entitled "Surgical Instrument for Manipulating and Passing Suture" each of which the entirety is incorporated by reference herein.

FIELD OF THE INVENTION

The present invention relates to a surgical instrument that can manipulate and pass suture through tissue.

BACKGROUND

Endoscopic surgery involves the performance of surgical procedures through small openings and under visualization using an endoscope. Access to a target tissue is normally provided through one or more portals formed directly in the patient's body or through one or more cannulas inserted into the patient's body through small incisions. A desired surgical procedure is carried out by a surgeon through the use of elongated instruments inserted through these cannulas.

Often it is necessary to pass suture through tissue during an endoscopic procedure. This could be required to mend a tear in the tissue or to connect two or more pieces of the soft tissue to one another. Although this task is not uncommon, passing and retrieving suture through tissue can be challenging in an endoscopic or arthroscopic procedure where visualization and space is limited.

Various endoscopic instruments have been developed to pass and retrieve suture through tissue. In some instances, retrieval of suture is accomplished by simply grasping it with regular forceps or other graspers having a suture capturing aperture formed at the distal tip when the forceps jaws are closed. Some suture retrievers include simple loops which extend from the tip of an elongated tube and which can be closed upon a suture passed through the loop.

U.S. Pat. No. 5,250,054 to Li, for example, discloses a suture retriever in the form of a knot tying device having an elongated inner rod slidably situated within an elongated outer sleeve. The distal end of the inner rod is provided with a pre-formed bend and the tip has a crochet-type hook to retrieve suture. This device, however, requires a separate needle to suture tissue.

Other devices combine a needle and suture grasper in one instrument. For example, U.S. Pat. No. 5,312,432 to Trott describes an endoscopic suturing needle having an elongated tubular housing having a needle at the distal tip and a trigger mechanism to advance and retract the needle relative to the housing. The needle is pointed and flat and has a recess provided at a predetermined distance proximal to the needle tip. The recess provides an opening to capture suture material therein. This allows the needle to either push or pull suture through selected tissue. Repeated manipulation of the suture can thus create the desired surgical stitch.

Another type of suturing needle is disclosed in U.S. Pat. No. 5,222,977 to Esser in which the needle tip is stationary and a movable slide is provided to open and close a suture receiving recess spaced a predetermined distance from the needle tip.

Many of the above referenced devices are limited because the suture needle/retrieval devices have suture snares which are situated on or in line with the needle body. Consequently, the device must be manipulated close enough to the suture to guide the suture into a suture receiving recess so the recess can be closed to retain the suture. In an endoscopic procedure positioning the suture in such close proximity to the recess can be difficult.

U.S. Pat. No. 8,066,718 to Weisel et al. discloses an expandable needle suture apparatus comprising bifurcated needle portions which define a suture slot.

U.S. Pat. No. 5,499,991 to Garman discloses a suture retriever and method for manipulating suture during endoscopic surgical procedures. The suture retriever has an elongated housing provided with a solid needle tip and a lateral opening situated proximal the needle tip. A suture engaging hook is extendable through the lateral opening and away from the axis of the housing in order to snare a suture. The hook is situated at the distal end of an elongated flexible support which is pre-formed in order to enable the hook to be laterally displaced from the axis of the needle tip when the support is moved distally relative to the lateral opening. When a suture is engaged by the hook, the latter is retracted proximally in order to place and hold the suture adjacent the lateral opening.

A problem with certain hooks (such as a full circle hook), or the like, however, is that such hooks tend to increase the size of the device profile penetrating the tissue, making endoscopic surgical procedures more challenging. Adding hinged jaw mechanisms make it harder to work in the tight needle bends required to reach certain anatomical areas such as the inferior labrum. Adding such hooks at the distal end also increases the probability of inadvertently snaring tissue, and being prevented from releasing the tissue, which may damage the tissue and/or the device.

Suturing the labrum, for example, can prove challenging particularly when the tissue is severely damaged and only small areas of tissue are available to pass suture. In such cases, a novel device would be desired that could decrease the overall profile of the feature penetrating the tissue, and optimize the working profile of the instrument to improve access to the working site.

Another shortcoming with various suturing devices is that they are relatively complex to operate, making it harder for the average surgeon to utilize, and increasing the likelihood of device failure.

Accordingly, an endoscopic suturing instrument for manipulating suture through tissue which overcomes the above described shortcomings is still desirable.

SUMMARY OF THE INVENTION

A suture manipulating instrument passes suture through tissue. The instrument comprises a handle mechanism and a working distal end. The working distal end comprises a needle and a preformed inner member extending therethrough. The handle mechanism can be used to manipulate the needle and wire in a manner which would allow the wire to grasp and manipulate suture by pinning and/or trapping the suture against the needle.

In an embodiment a suture instrument for manipulating and passing suture through a tissue comprises a handle; an elongate tubular shaft extending from the handle, and a needle extending from the distal section of the tubular shaft. The needle comprises an outer body defining a lumen extending therethrough, a tissue penetrating distal tip, and a laterally disposed slot along the body and in communication with said lumen.

In embodiments the slot may extend along the body of the needle from a first location proximal the distal tip to the distal tip. In embodiments, the distal tip may be hollow beveled structure.

In embodiments the instrument may further comprise an elongate inner member such as but not limited to a wire member. The elongate inner member is movably disposed within the lumen of the needle. The inner member moves from a retracted configuration in which at least a portion of the distal section of the inner member is situated within the slot of the needle, and an extended configuration in which the distal section of the inner member extends from the slot of the needle. The distal section of the inner member preferably has a preformed shape which the distal section assumes when the inner member is in the extended configuration and the distal section is unconstrained by the lumen of the needle and wherein the preformed shape comprises a first bend which directs the distal section of the inner member at a first angle laterally away from a needle axis. The distal section of the inner member and the slot of the needle cooperate together to clamp a suture disposed therebetween when the inner member is in the retracted configuration.

The structure of the inner member may vary widely. In one embodiment, the inner member is branchless. In another embodiment the preformed shape of the distal section of the inner member is hook-less.

The diameter of the inner diameter may be constant or vary along the length. In another embodiment, the inner member comprises a thin flat elongate body. The body may be formed from a flat sheet of material which is cut to shape.

The inner member may comprise one or more bends along its length. In one embodiment the first bend assumes a first angle of at least 45 degrees with respect to the needle axis when the inner member is unconstrained.

In another embodiment the inner member comprises a discrete second bend distal to the first bend. The second bend directs a length of the distal section of the inner member at a second angle with the needle axis, and the second angle being less than the first angle.

In another embodiment the inner wire member comprises a discrete third bend distal to the second bend.

In another embodiment, the inner member comprises two dog-leg bends which collectively form a box-hook type shape.

The shape of the needle may also vary. In one embodiment the body of the needle comprises a side wall, and a suture holding section in the side wall for locating the suture when clamped between the needle and the inner member. The suture holding section may comprise a recess in the side wall.

In embodiments the recess comprises a distal surface, a base, and a proximal surface which, when the inner member is in the retracted configuration, collectively hold the suture therebetween.

In one embodiment the distal surface forms a distal ramp and the distal ramp forms an angle between 20 and 65 degrees with the needle axis.

In embodiments the base of the suture holding section has a length greater than 0.3 mm. In one embodiment the recess has a depth greater than 0.3 mm.

In embodiments the proximal surface forms a proximal ramp and the proximal ramp forms an angle greater than 90 degrees with the needle axis.

In another embodiment the suture holding section comprises an undercut in at least one of the proximal and distal surfaces.

In another embodiment the slot further comprises a wire relief section proximal the suture holding section.

In another embodiment the inner member comprises a wire bundle.

In another embodiment the inner member comprises a trapping feature, and the trapping feature is one selected from the group consisting of a hold, ferrel, cleat, clamp, wedge, and bulb.

In another embodiment the suture instrument comprises a lever movably disposed in said handle and linked to the inner member to manipulate the inner member from the retracted configuration to the extended configuration.

In another embodiment the shape of the distal section of the needle is curved. In one embodiment the shape of the distal section of the needle is crescent shaped.

In another embodiment the distal tip of the needle comprises an open cavity for receiving a tip section of the inner member when the inner member is retracted.

In another embodiment a suture instrument for manipulating and passing suture through a tissue comprises: a handle; an elongate tubular shaft extending from the handle; and a needle extending from the distal section of the tubular shaft. The needle comprises an outer body defining a lumen extending therethrough, a tissue penetrating distal tip, and a slot along the body and in communication with said lumen; and an elongate inner member movably disposed within said lumen of said needle. The inner member and needle cooperate together to move between a plurality of configurations including: i) a closed configuration in which at least a portion of the distal section of the inner member is situated within the slot of the needle to clamp the suture therebetween; ii) an open configuration in which the distal section of the inner member extends from the slot of the needle and defines a suture capture zone between the inner member and the needle; and iii) an intermediate configuration in which the inner member and the needle loosely encircle a section of suture such that the suture is slidably held therebetween.

In another embodiment the distal section of the inner member has a hook-less preformed shape which the inner member assumes when the inner member is in the open configuration.

In another embodiment the inner member preformed shape comprises a plurality of discrete bends.

In another embodiment the needle comprises a crescent shape.

In another embodiment the slot comprises a plurality of sections, and said plurality of sections include a proximally disposed wire relief section, and a suture holding section distal to the wire relief section.

A suture instrument for manipulating and passing suture through a tissue includes a handle; an elongate tubular shaft extending from the handle. The tubular shaft comprises a distal section; a needle extending from the distal section of the tubular shaft. The needle comprises an outer body defining a lumen extending therethrough, a tissue penetrating distal tip, and a laterally disposed slot along the body and in communication with the lumen. An elongate inner member is movably disposed within the lumen of the needle, and the inner member is movable from a first retracted configuration in which at least a portion of the distal section of the inner member is situated within the slot of the needle, a second retracted configuration in which the entire distal section of the inner member is situated within the lumen of the needle, and an extended configuration in which the distal section of the inner member extends from the slot of the needle. Additionally, in embodiments, the distal section of the inner member has a preformed shape which the distal section assumes when the inner member is in the extended configuration and the distal section is unconstrained by the lumen of the needle. The preformed shape comprises a first bend which directs the distal section of the inner member at a first angle laterally away from a needle axis, the needle axis extending through the needle towards the distal tip of the needle; and the distal section of the inner member and the slot of the needle cooperate together to: (a) clamp a suture disposed therebetween when the inner member is in the first retracted configuration, (b) strip the suture from the inner member when the inner member is moved into the second retracted position subsequent to clamping the suture, and (c) eject the suture from the slot when the inner member is in the extended configuration.

In embodiments, the body of the needle comprises a side wall, and a suture holding section in the side wall for locating the suture when clamped between the needle and the inner member. The suture holding section may include a recess in the side wall. In embodiments the recess has a distal surface, a base, and a proximal surface which, when the inner member is in the retracted configuration, collectively hold the suture therebetween. The distal surface blocks the suture from entering the lumen as the inner member is moved from the first retracted configuration to the second retracted configuration. In embodiments the distal surface comprises a deformed tab.

In embodiments the lumen contains a feature to strip the suture. The lumen may comprise a detent, blocking the suture from entering the lumen as the inner member is moved from the first retracted configuration to the second retracted configuration, or a protrusion, adapted to retard the suture from further movement in the proximal direction as the inner member is moved from the first retracted configuration to the second retracted configuration.

In another embodiment a method of endoscopically manipulating and passing suture through tissue comprises the steps of: piercing the tissue at a first location with a needle to place the needle in proximity to the suture to be retrieved; extending an elongate inner member from a lateral slot in the needle thereby creating a suture capture zone between the inner member and the needle; positioning the suture capture zone around the suture; manipulating a distal tip section of the inner member into the lateral slot of the needle while the suture is within the suture capture zone, thereby clamping the suture between the inner member and the needle such that the suture is compressed between the inner member and the needle; and removing the needle from the tissue to retrieve the suture through the tissue.

In another embodiment the clamping step is carried out by retracting the inner member through the needle.

In another embodiment the inner member is further retracted within the needle lumen, drawing a length of suture into the needle lumen. The suture is subsequently ejected from the needle lumen to form a suture loop.

In another embodiment, a suture push surface on the inner member enhances grabbing, pushing, and ejecting the suture. The suture push surface may comprise a notch or asperity. An example of an asperity is a texture element or burr.

In another embodiment the method further comprises piercing the tissue at a second location with the needle while the needle is carrying the suture to place the suture through the tissue, the step of piercing the tissue at a second location being performed prior to the step of piercing the tissue at a first location. The method further comprising extending the elongate inner member from the lumen in the needle thereby unclamping the suture from the inner member and the needle; and removing the needle from the tissue, thereby leaving the suture extending through the tissue.

In another embodiment the extending step is performed by extending a distal tip of the inner member in a first direction making a first angle with a needle axis of the needle and a second direction making a second angle with the needle axis, and wherein the second angle is less than the first angle.

In another embodiment the inner member is a preformed wire and comprises a plurality of discrete bends.

In another embodiment the tissue to be sutured is a shoulder labrum.

BRIEF DESCRIPTION OF THE DRAWINGS

FIGS. 8-18 are illustrations of a surgical instrument manipulating and passing suture through tissue;

FIGS. 27*a*-27*b* are perspective and side views respectively of the working end of another suture manipulating instrument in an extended configuration;

FIGS. 34b-34c are various cross sectional views of the needle distal section and inner member shown in FIG. 34a;

FIGS. 35b-35c are various cross sectional views of the needle distal section and inner member shown in FIG. 35a;

FIGS. 36b-36c are various cross sectional views of the needle distal section and inner member shown in FIG. 36a;

FIGS. 39-40 are perspective and cross sectional views respectively of the needle distal section and inner member shown in FIG. 37, in a retracted configuration;

FIG. 41 is a perspective view of the needle distal section, suture, and inner member in an extended configuration;

FIGS. 46a-46b are side and perspective views respectively of various needle distal sections and inner members shown in extended configurations;

FIG. 55 is a side view of another needle distal section and inner member shown in an extended configuration;

FIGS. 56a-56b are side and front views respectively of the inner member shown in FIG. 55;

FIG. 57 is a side view of another needle distal section and inner member shown in an extended configuration;

FIGS. 58a-58b are side and front views respectively of the inner member shown in the needle of FIG. 57;

FIG. 59b is a side view of the inner member shown in the needle of FIG. 59a;

FIGS. 60a-60b are side and front views respectively of another needle distal section and inner member in extended configurations;

FIGS. 60c-60d are side and front views respectively of the inner member shown in the needle of FIGS. 59a-59b;

DETAILED DESCRIPTION

Before the present invention is described in detail, it is to be understood that this invention is not limited to particular variations set forth herein as various changes or modifications may be made to the invention described and equivalents may be substituted without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail).

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. It is also to be appreciated that unless defined otherwise, all technical and scientific terms used herein have the same meaning as commonly understood by one of ordinary skill in the art to which this invention belongs.

Figure 1:
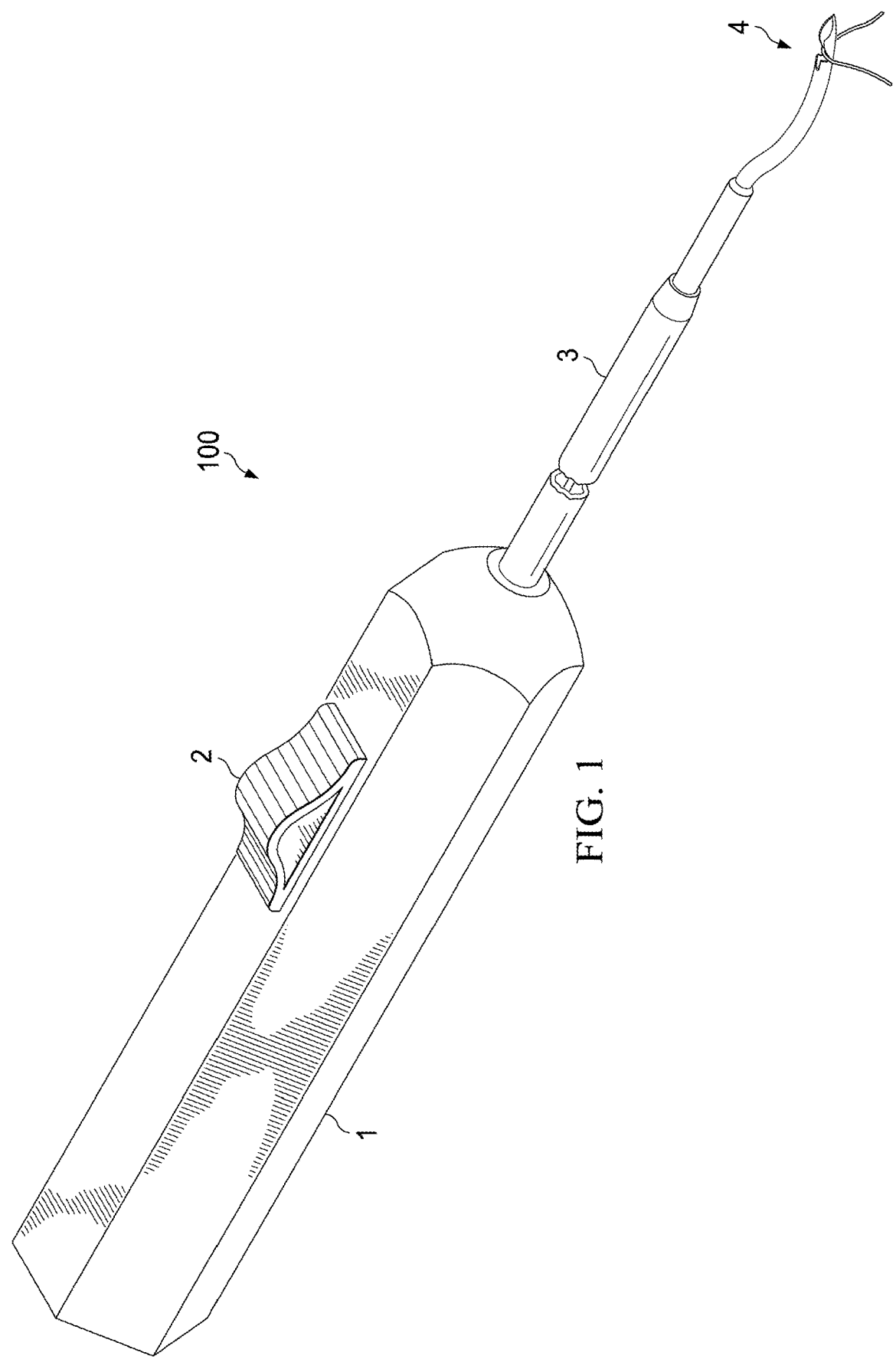
FIG. 1 is a perspective view of a suture manipulating instrument holding a suture.

A surgical instrument 100 for manipulating and passing suture is shown in FIG. 1. The instrument 100 comprises a handle 1, a lever, slide, or button 2, an elongate shaft 3, and a working end 4. Slide 2 controls the suturing manipulating mechanism at the working end 4, as will described herein.

The instrument may be used to pass and/or retrieve suture through tissue in a wide variety of applications including, for example, labrum or rotator cuff repair.

Figure 2:
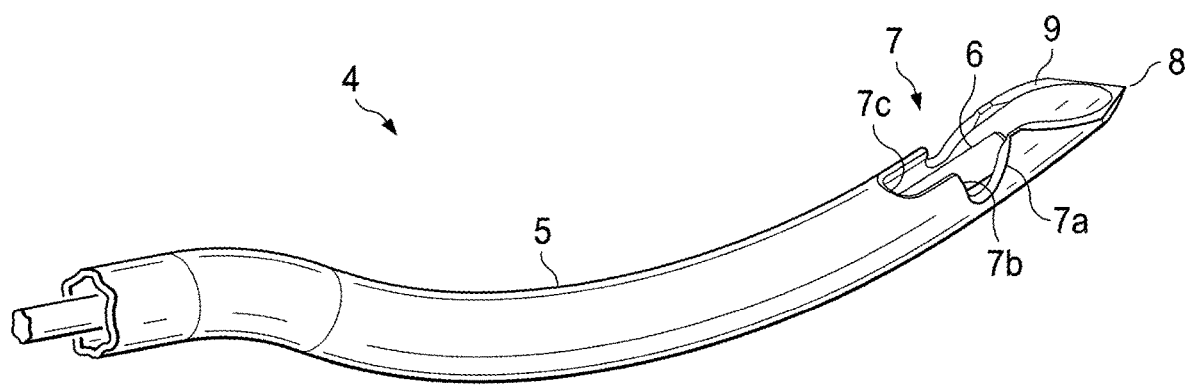
FIGS. 2-3 are perspective and cross sectional views respectively of the working end of a suture manipulating instrument in a retracted configuration.
Figure 3:
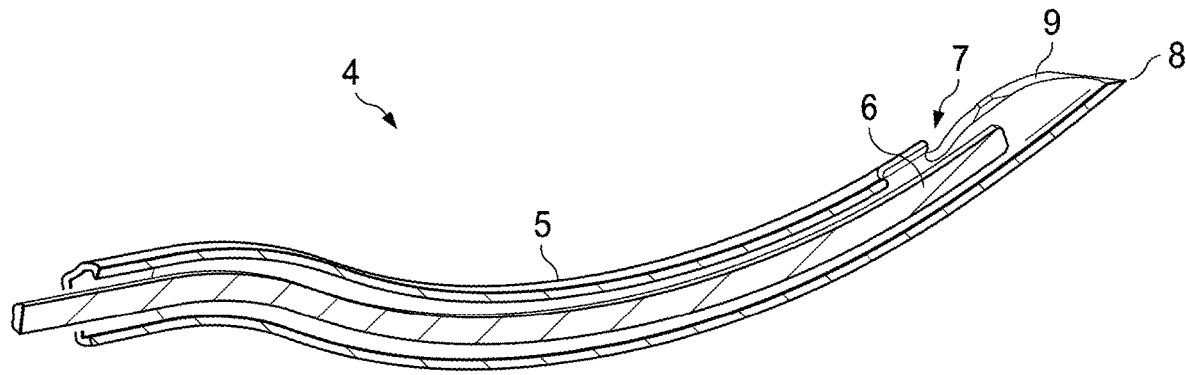

A detailed view of one possible configuration of the working end 4 is shown in FIGS. 2 and 3. The working end 4 is shown having a needle 5 and an inner member 6 (shown in a retracted state). The needle 5 has a laterally disposed suture slot 7 and a needle point or tissue penetrating distal tip 8. Needle point 8 may be formed variously, such as for example, a bevel 9 as shown in FIG. 2.

The suture slot 7 is preferably configured in such a manner to facilitate suture grasping when suture is pinned or clamped between the inner member 6 and the walls of the needle 5.

In the configuration shown in FIGS. 2-3, the suture slot 7 has a distal ramp 7a, a vertical wall 7b, and a wire relief slot 7c. As discussed herein, features 7a and 7b can have different configurations of vertical and/or ramp walls. Additionally, the needle point 8 can be used to facilitate tissue puncturing.

Figure 4:
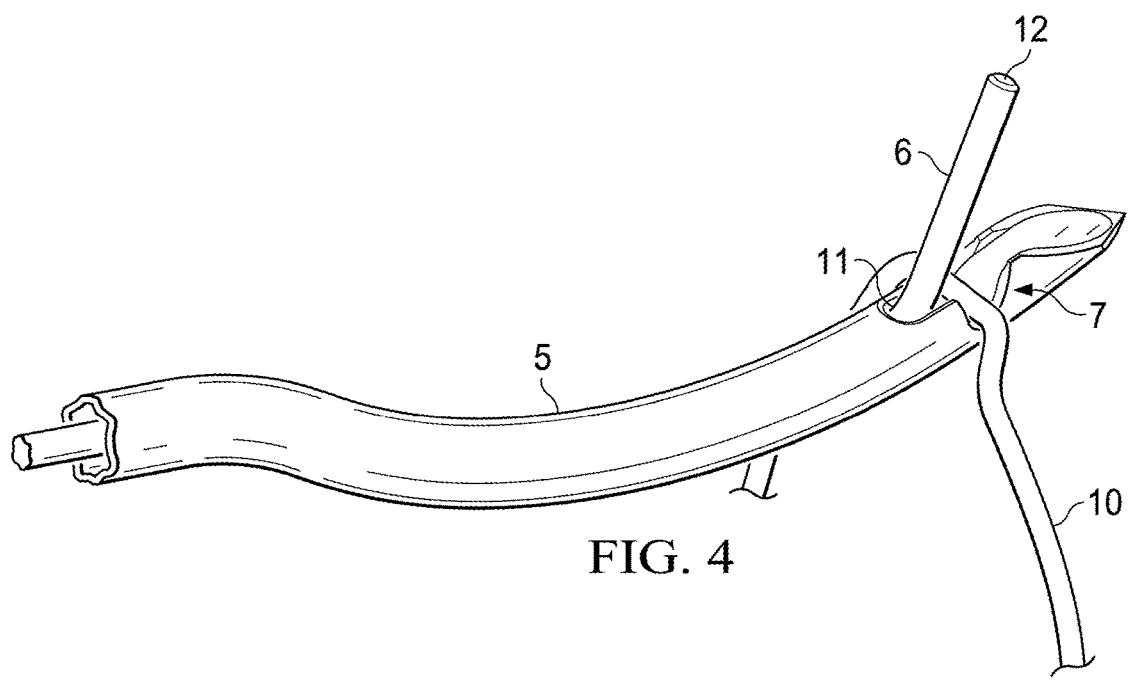
FIGS. 4-5 are perspective and cross sectional views respectively of the working end of a suture manipulating instrument in an extended configuration.
Figure 5:
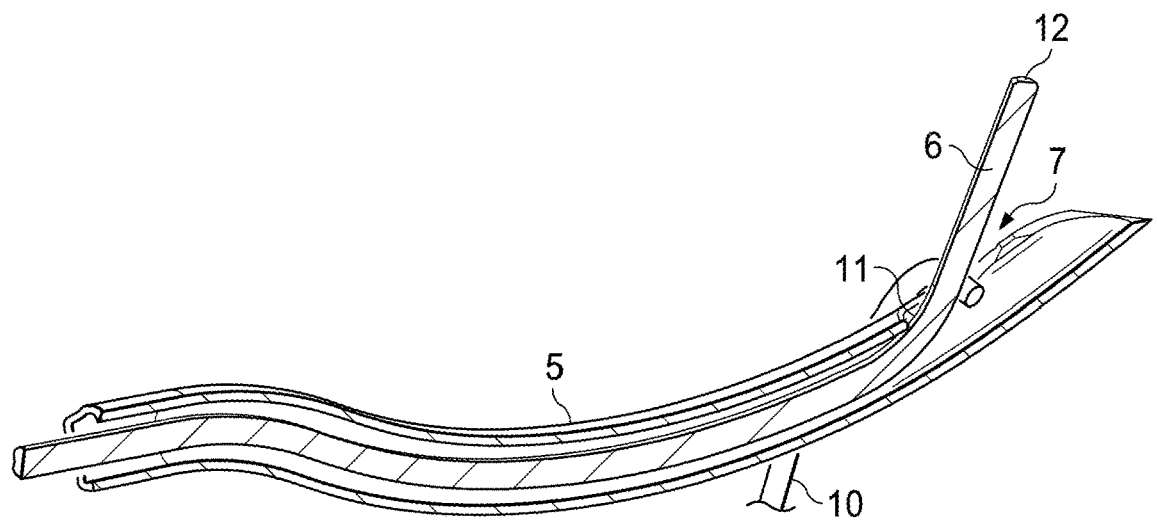

FIGS. 4 and 5 show inner member 6 in an extended or deployed state with a suture 10 lying within the suture slot 7 of needle 5. In the embodiment shown, a single proximal bend 11 is preformed in the inner member 6 proximal to the inner member tip 12.

The inner member may be formed in such a manner that causes its tip 12 to move away from the needle 5 as the inner member 6 is deployed. This action creates space (e.g., a suture capture zone) between the inner member 6 and needle 5 to allow the suture 10 to slide in between the inner member 6 and needle 5. Inner member is shown in this embodiment as a wire member. However, the inner member may be fabricated from other materials and take other forms. For example, inner member may be a metal or alloy filament, braid, or wire bundle comprising one or more elements. A preferred material is super elastic materials such as Nitinol.

The inner wire 6 is retracted once the suture 10 is properly positioned between the inner wire 6 and needle 5. Interaction between the proximal bend 11 on inner wire 6 and the suture slot 7 results in the inner wire tip 12 being displaced toward the needle axis and subsequently traps the suture 10.

Figure 6:
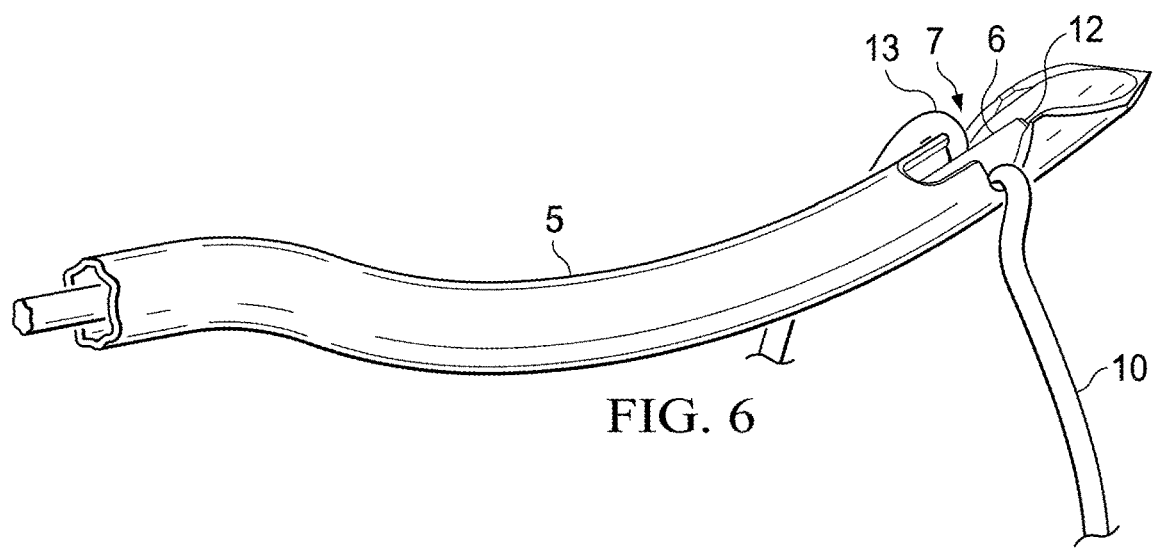
FIGS. 6-7 are perspective and cross sectional views respectively of the working end of a suture manipulating instrument in a suture grasping configuration.
Figure 7:
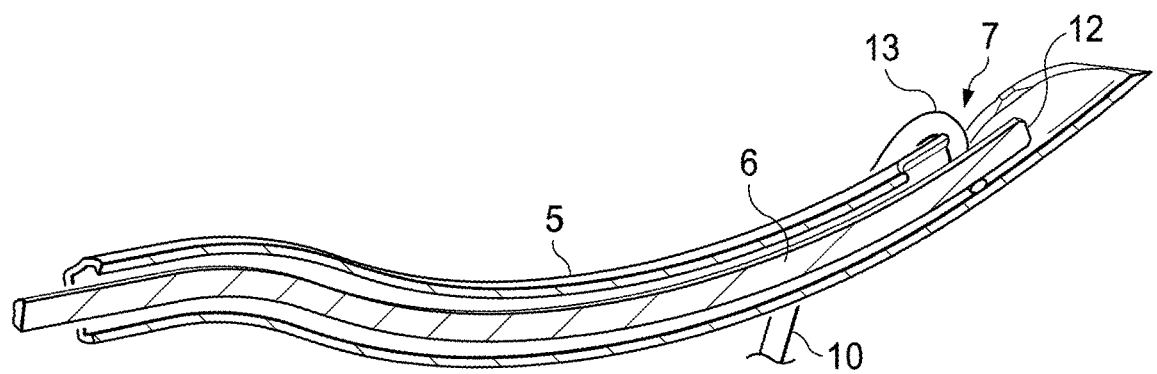

FIGS. 6 and 7 show the inner wire 6 in the retracted state with a suture 10 clamped or pinned across the suture slot 7. In this embodiment the suture 10 is forced into a circuitous or tortuous path 13 between the inner wire 6 and the suture slot 7 which increases the hold on the suture 10.

Procedure

Figure 8:
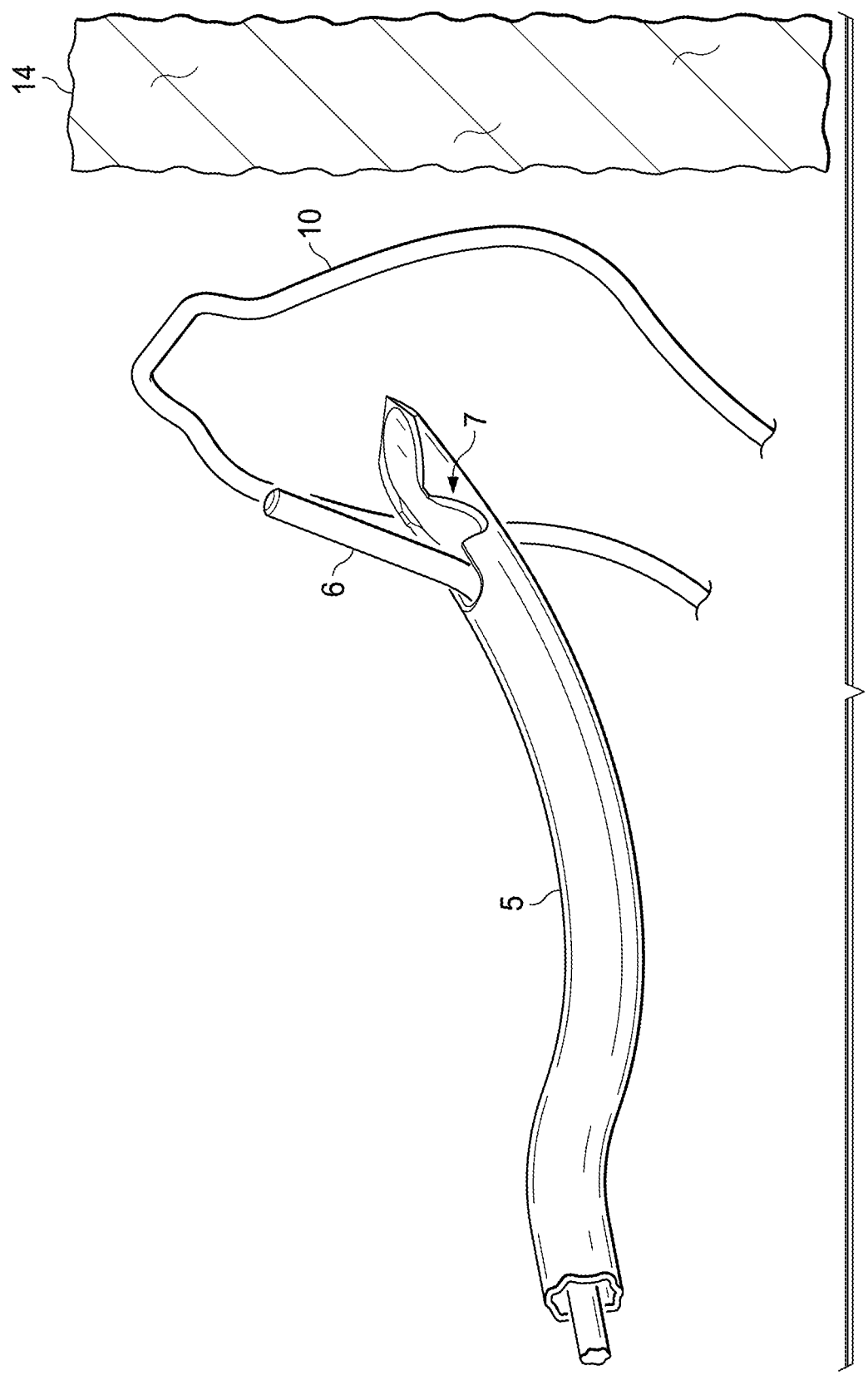

FIGS. 8 to 13 show one possible method of using the current embodiment to pass suture from one side of tissue 14 to the other. Examples of tissue include without limitation labral tissue. FIG. 8 shows the instrument with the inner member 6 in the extended or deployed state and in position to grab suture.

Figure 9:
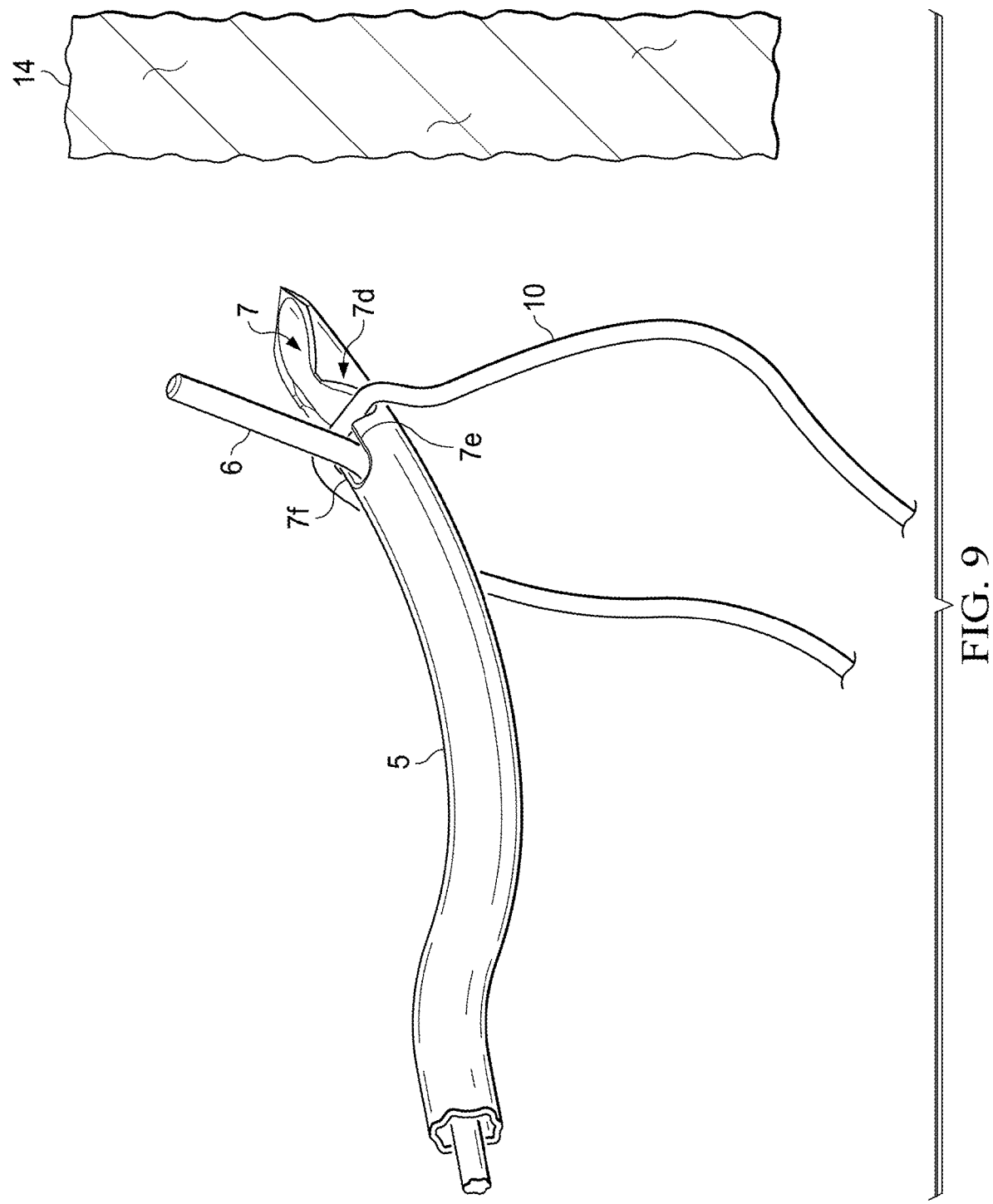

The device is then manipulated to position the suture 10 between the inner wire 6 and the suture slot 7 as shown in FIG. 9. In particular, a section of the suture 6 rests in a recess or suture capture zone 7d formed in the walls 7e, 7f of the needle 5.

Figure 10:
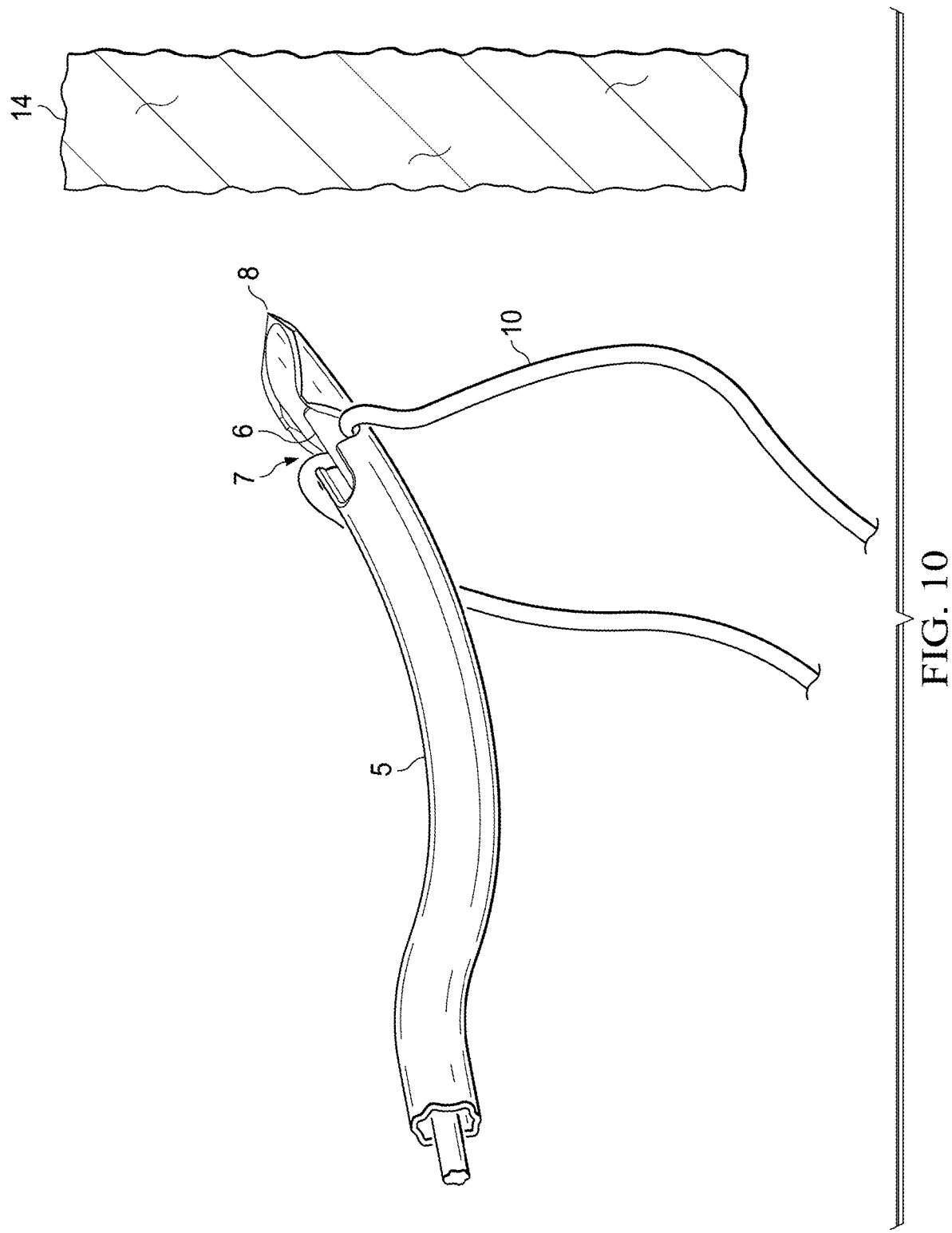

The inner wire 6 is then retracted thereby clamping, pinning or trapping the suture 10 between the inner wire 6 and the needle 5 as shown in FIG. 10.

Figure 11:
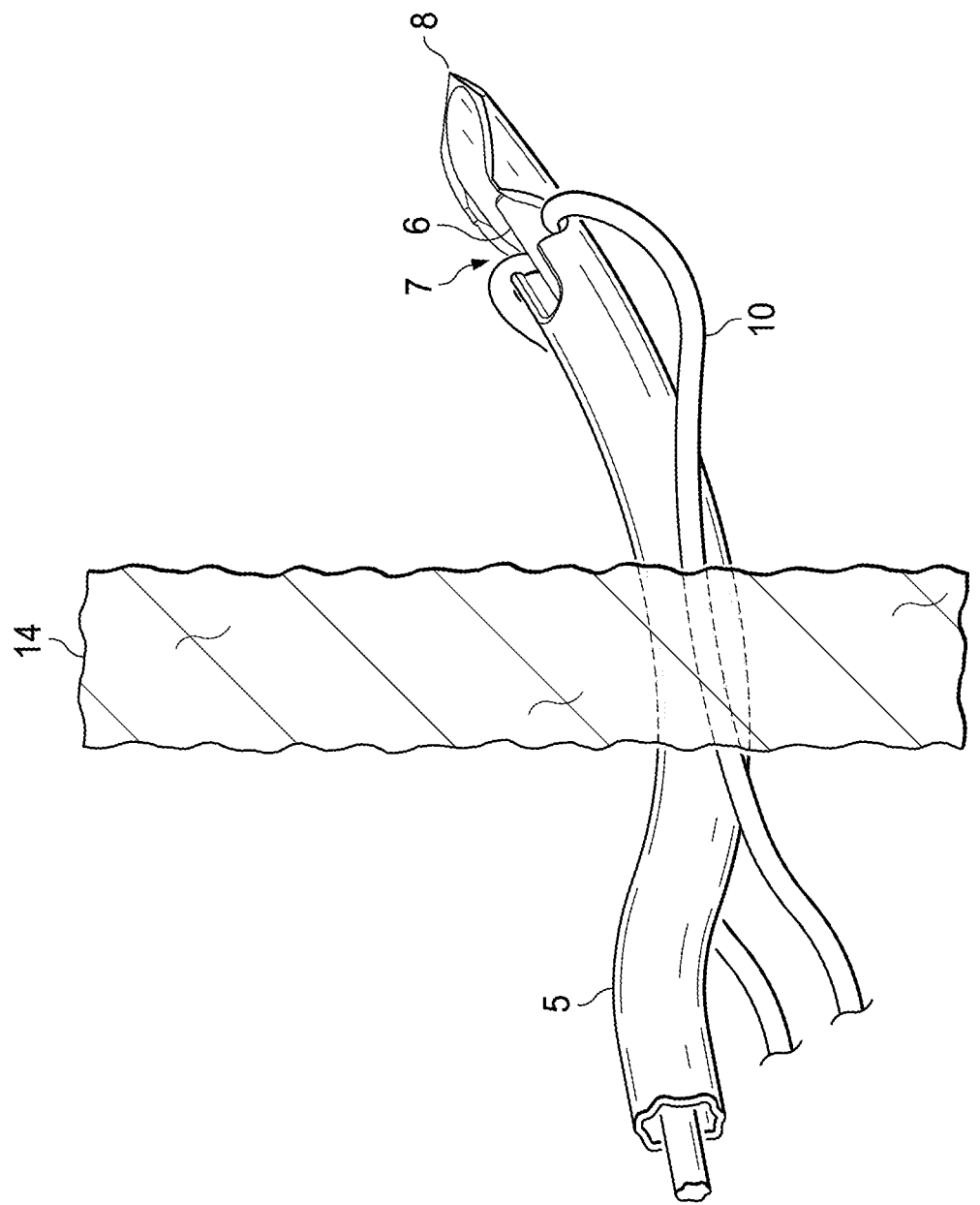

FIG. 11 shows piercing the tissue using the needle tip 8, thereby carrying the suture through the tissue.

Figure 12:
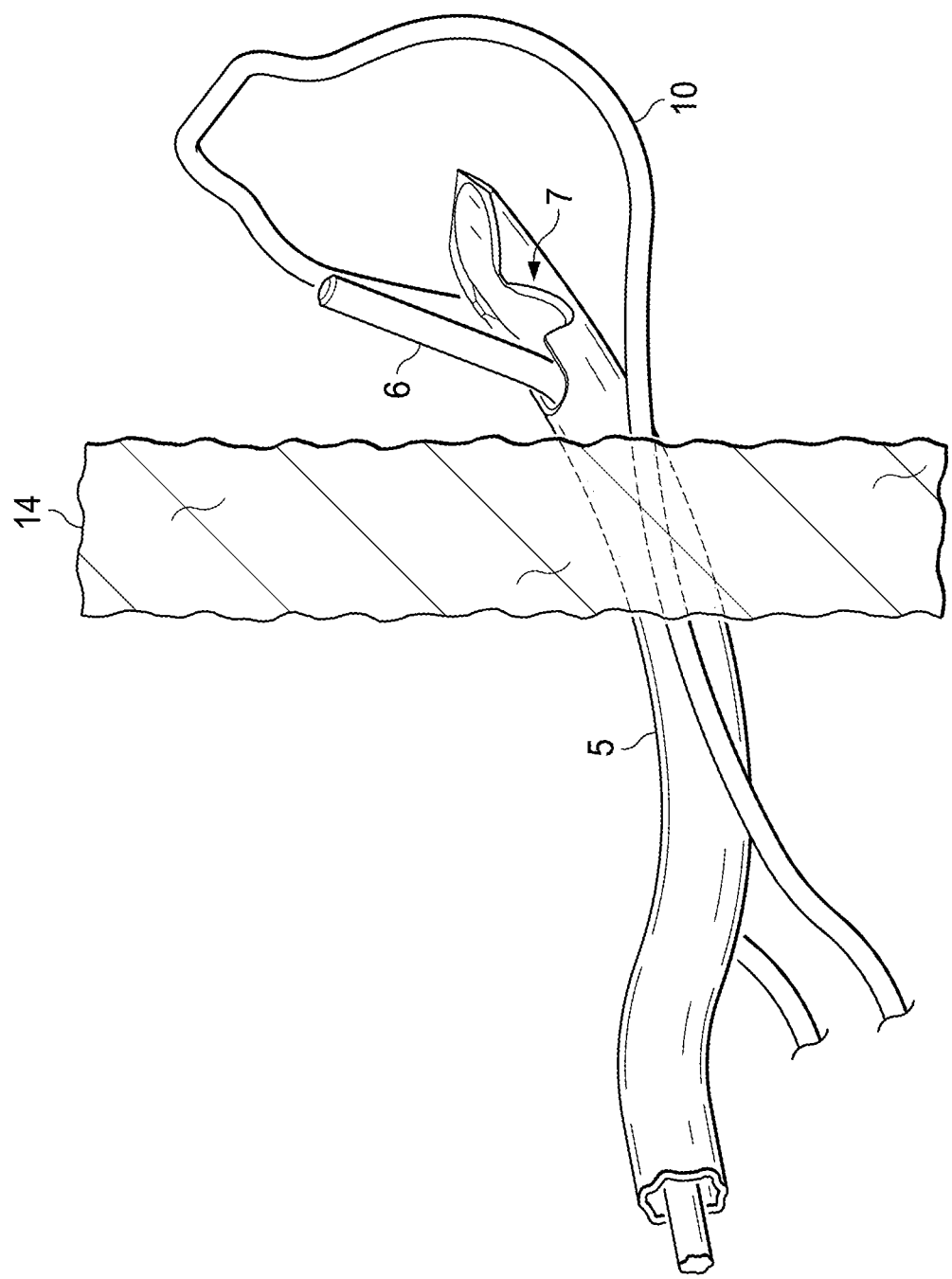
Figure 13:
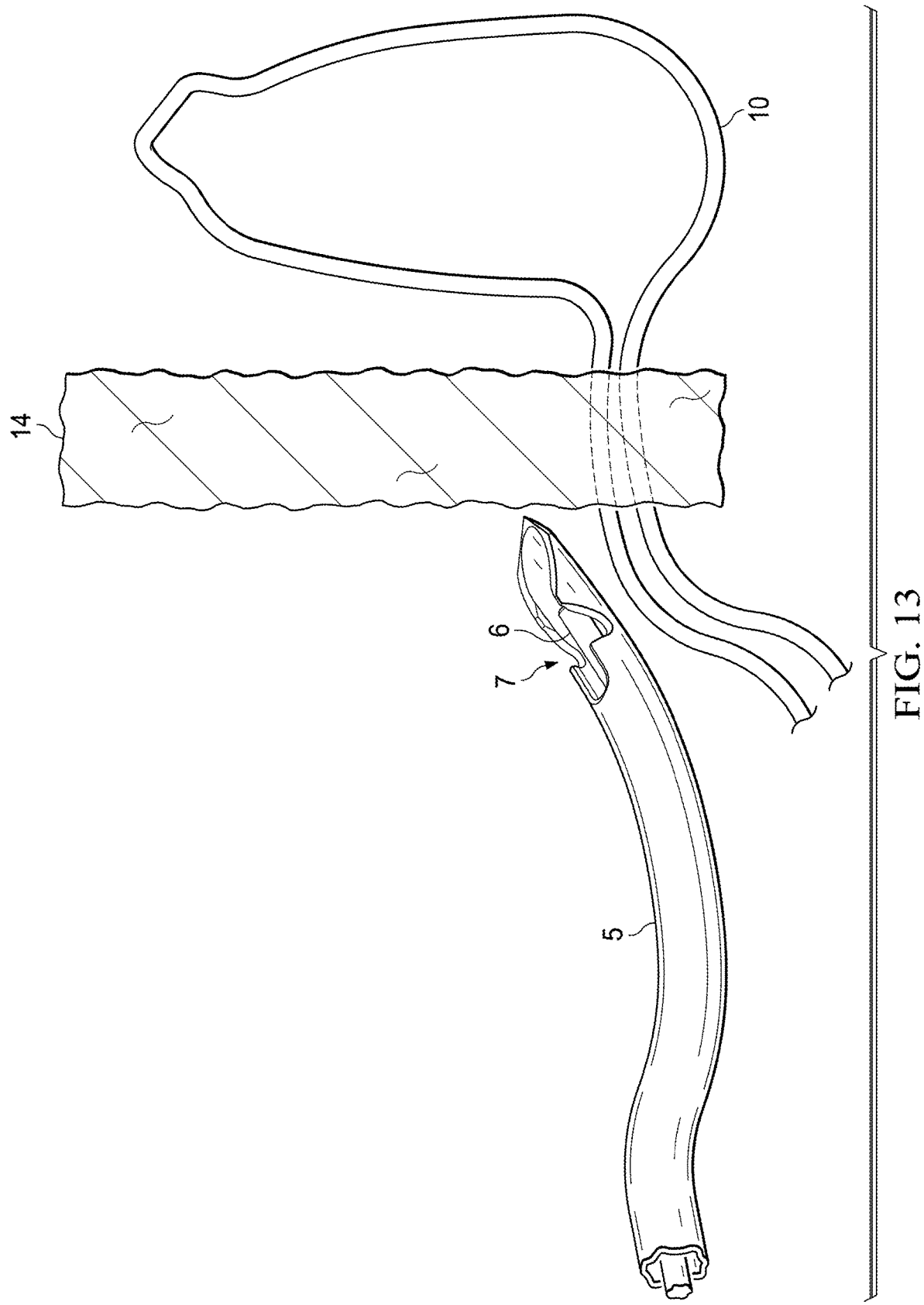
Figure 14:
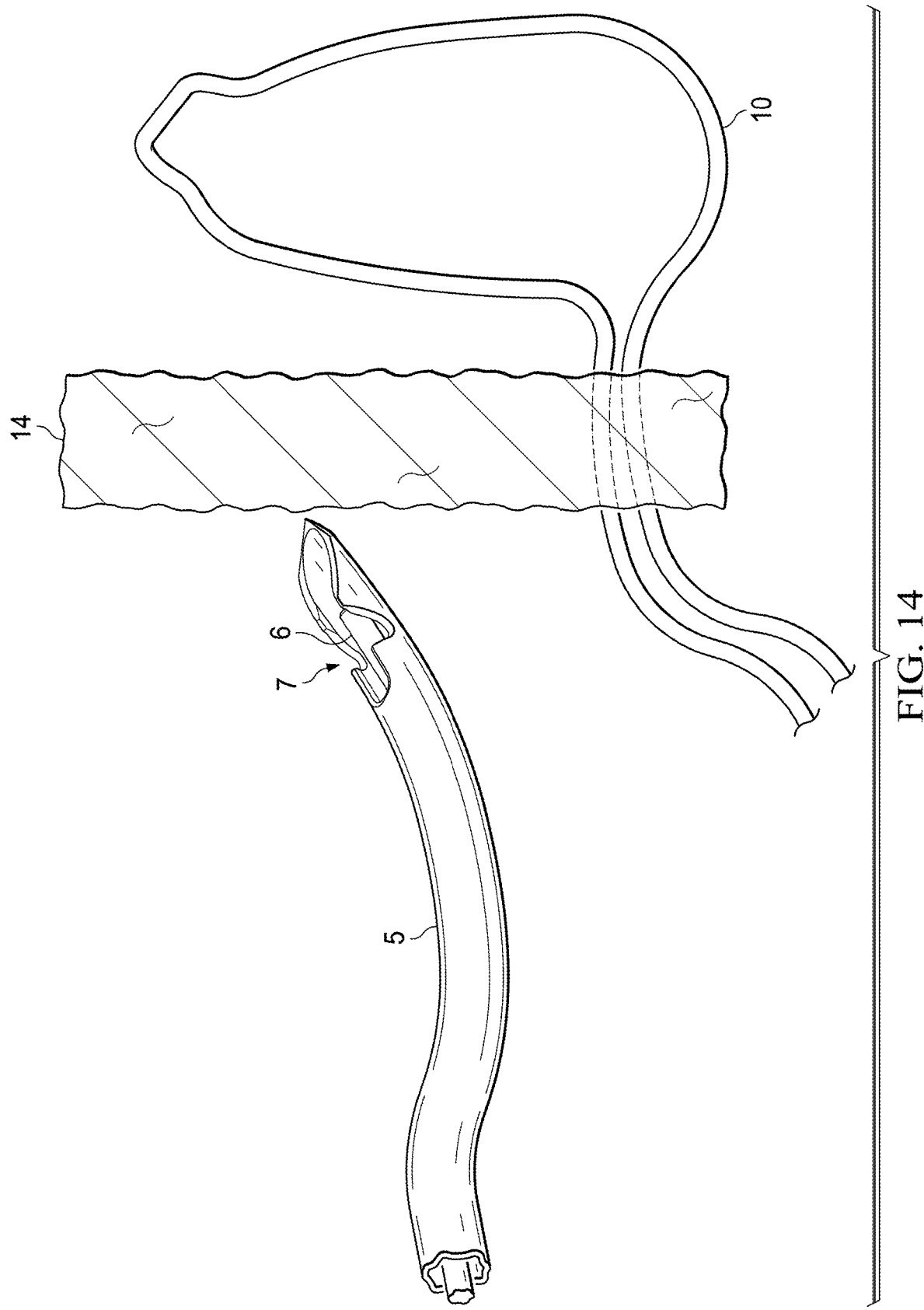

The inner wire 6 is then deployed to release the suture 10, retracted, and then the instrument is pulled back out of the tissue 14 as shown in FIGS. 12 and 13. Consequently, a section of suture is left extending through the tissue.

FIGS. 14 to 18 show one possible method of using the current embodiment to retrieve the suture that had previously been passed in order to form a stitch. Once the suture 10 has been passed through the tissue 14 the instrument is used to pierce the tissue 14 at a second location, different from the first location.

Figure 15:
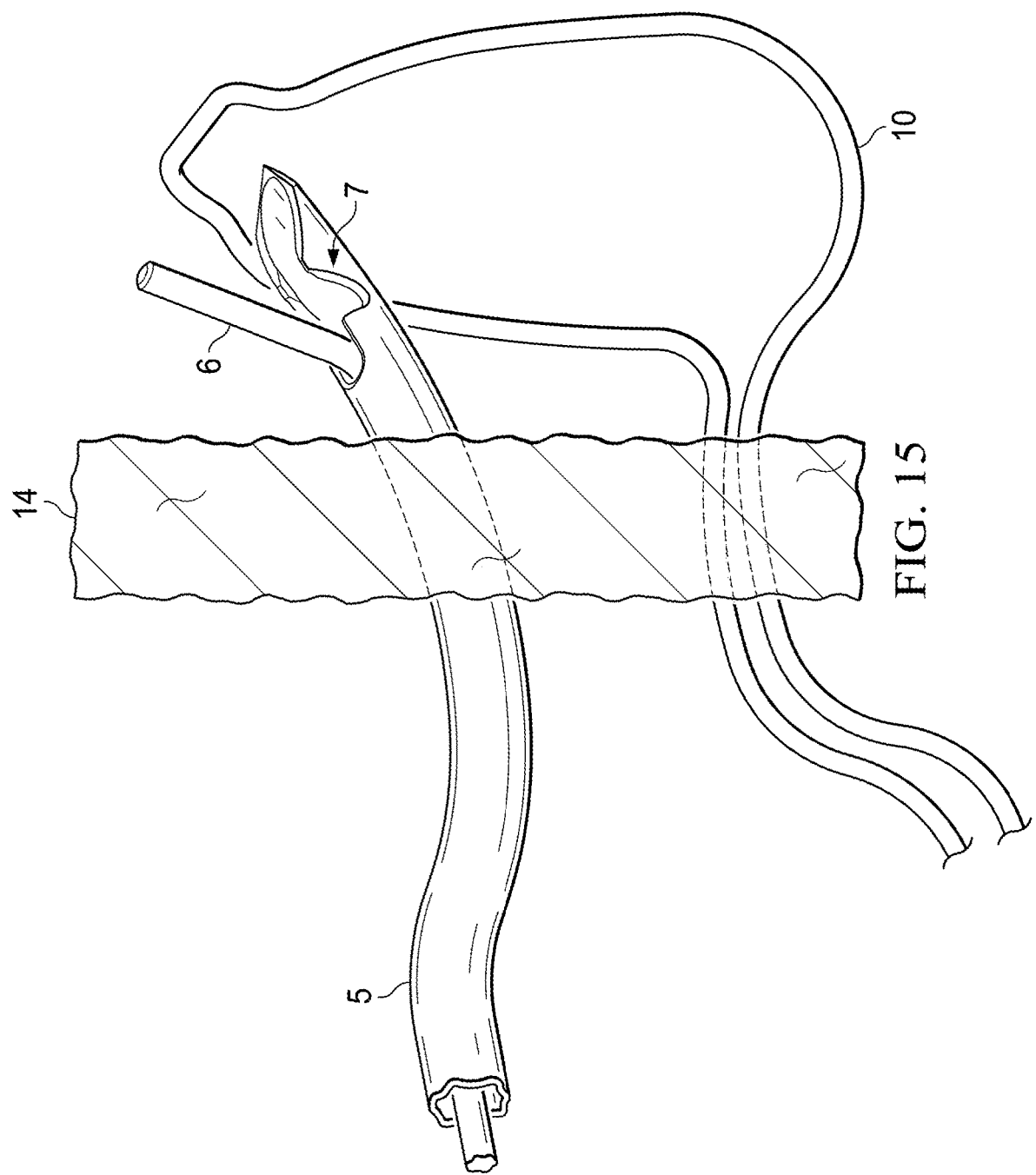

FIG. 15 shows the inner wire 6 deployed in order to create spacing between the inner wire 6 and suture slot 7.

With reference to FIG. 16, the device is manipulated in order to position the suture 10 between the inner wire 6 and the needle 5. The inner member 6 is then retracted to secure the suture 10.

FIG. 17 shows the distal working section of the needle 5 pulled back out of the tissue 14 creating a stitch in the tissue.

FIG. 18 shows the inner member in an extended position thereby releasing the suture 10 from the instrument.

Alternative Configurations

The working end 4 of the needle 5 can be formed into a variety of profiles including, but not limited to those illustrated in FIGS. 19 to 21.

Figure 19A:
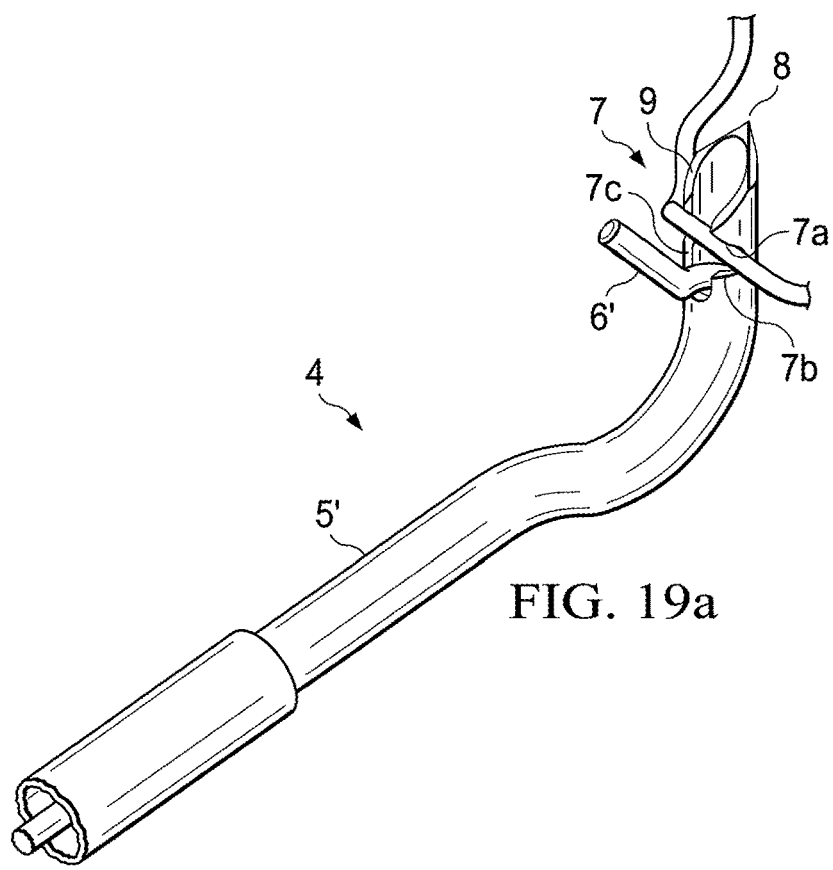
FIGS. 19*a*-19*b* are perspective views of the working end of another suture manipulating instrument in an extended configuration and a suture grasping configuration respectively.
Figure 19B:
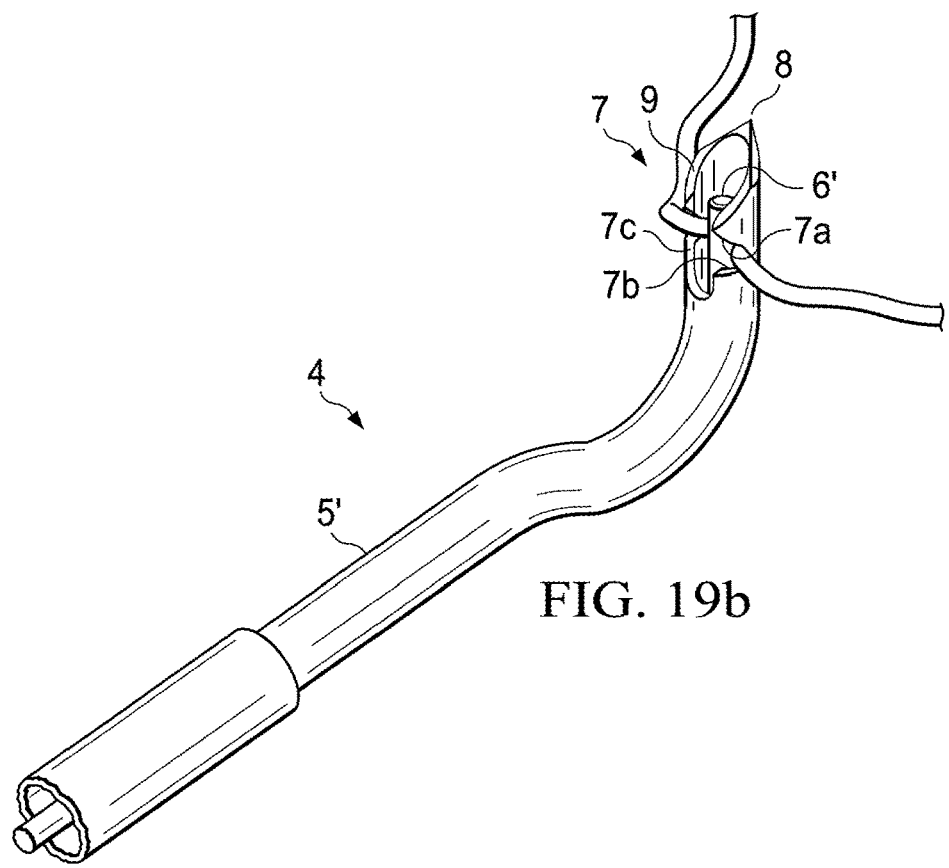

FIGS. 19a-19b show needle 5' having a relatively sharp upwards facing turn. This "Up" version is shown at about 90°. FIG. 19a shows inner wire 6' in a deployed or extended state. And FIG. 19b shows inner member 6' in a retracted suture clamping state.

Figure 20A:
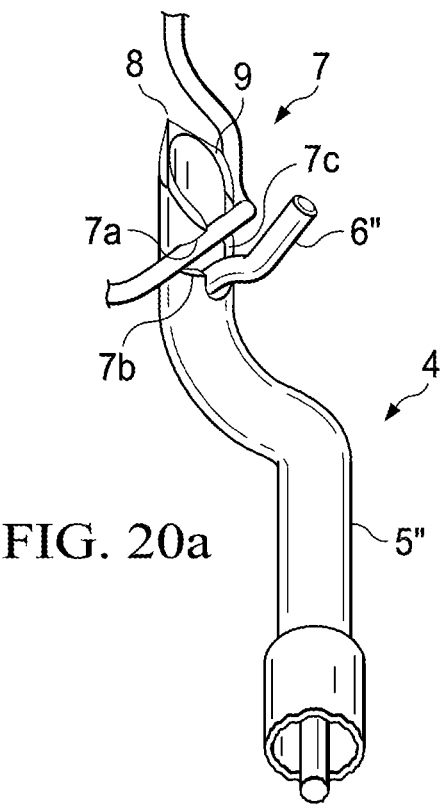
FIGS. 20*a*-20*b* are perspective views of the working end of another suture manipulating instrument in an extended configuration and a suture grasping configuration respectively.
Figure 20B:
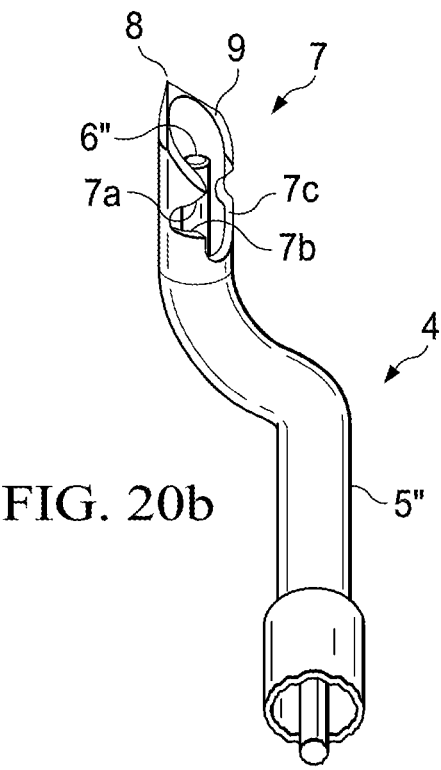

It is to be understood that the shape of the needle may vary. FIGS. 20a-20b, for example, show another needle shape. In particular, the embodiment shown in FIGS. 20a-20b is a 45° "Left" version. Inner member 6" is shown extended in FIG. 20a, and retracted in FIG. 20b.

Figure 21A:
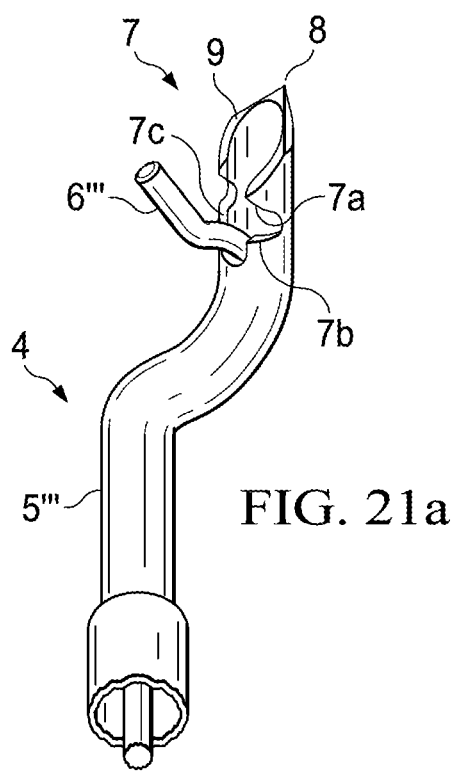
FIGS. 21*a*-21*b* are perspective views of the working end of another suture manipulating instrument in an extended configuration and a suture grasping configuration respectively.
Figure 21B:
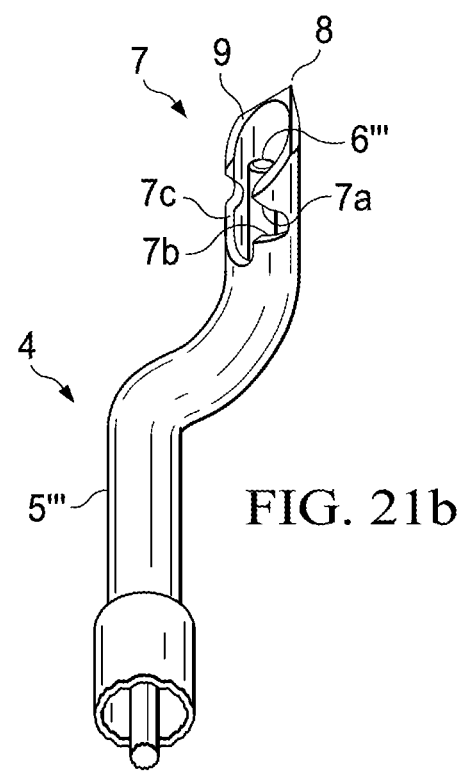

FIGS. 21a-21b show a 45° "Right" version. The inner member is shown extended in FIG. 21a, and retracted in FIG. 21b.

The suture slot 7 can be configured into a variety of profiles including, but not limited to those illustrated in FIGS. 22a to 22d.

Figure 22A:
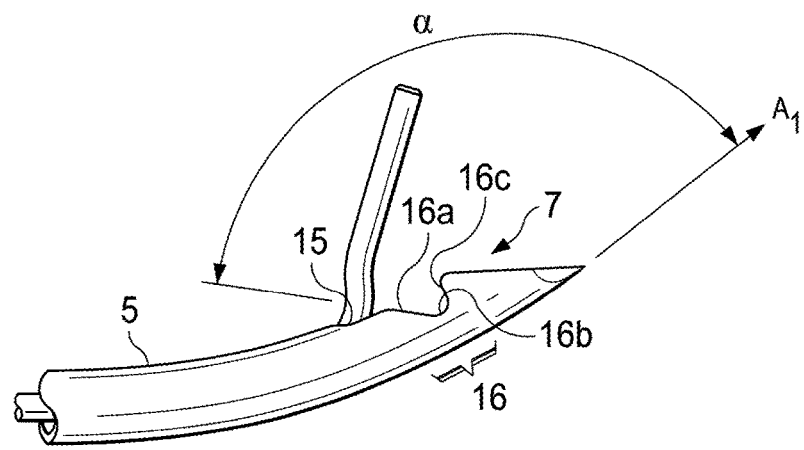
FIGS. 22*a*-22*d* are partial side views of suture manipulating instruments having various needle slot configurations.

FIG. 22a shows a suture slot 7 in the body of a needle 5. The slot 7 comprises a plurality of sections or regions. In particular, the suture slot 7 shown in FIG. 22a includes a wire relief area 15 (also shown, for example, in FIG. 34a and indicated by reference numeral 15') and a suture holding area 16. Suture holding area 16 comprises a proximal ramp 16a, a base 16b, and a distal surface 16c. Proximal ramp 16a is shown having an angle ($\alpha$) with needle axis (A1). Angle ($\alpha$) is shown having an angle of about 135 degrees, however, the angle ($\alpha$) may vary. Preferably, angle ($\alpha$) is equal to or greater than 90 degrees, and more preferably ranges from 90-135 degrees. Proximal ramp may be vertical.

Figure 22B:
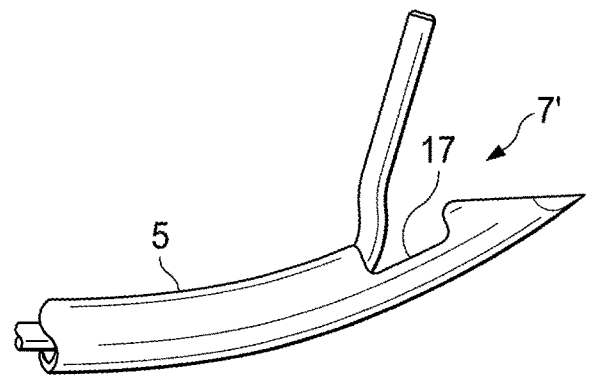

FIG. 22b shows another suture slot 7' with a rectangular profile and flat bottom or base 17.

Figure 22C:
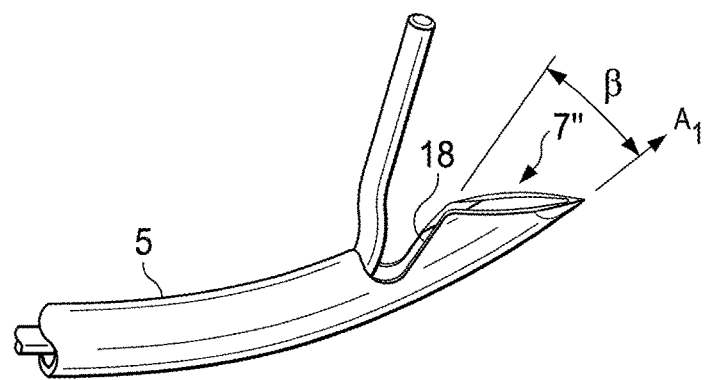

FIG. 22c shows a suture slot 7" with a distal ramp 18 and without a proximal slot or wire relief region. Distal ramp 18 is shown having an angle ($\beta$) with needle axis (A1). Angle ($\beta$) is shown having an angle of about 30 degrees, however, the angle ($\beta$) may vary. Preferably, angle ($\beta$) is less than 90 degrees, and more preferably from 20-65 degrees.

Additionally, though not shown in FIGS. 22a-22c, slot 7 may include both distal and proximal ramps.

Figure 22D:
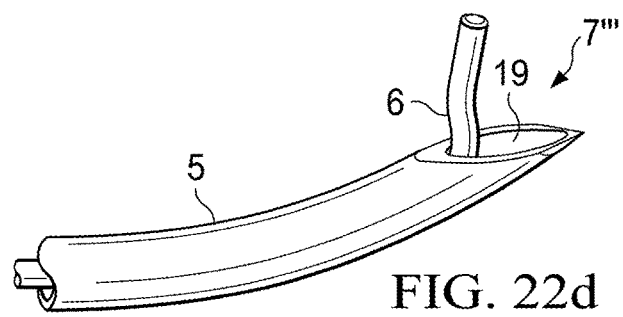

Additionally, although a preferred embodiment of the present invention includes a laterally disposed slot comprising a recess, the presence of such a slot is not essential. FIG. 22d, for example, shows an a needle 5 comprising an inner member 6 extending from an opening 19. A suture (not shown) may be clamped or pinned between the inner wire member 6 and the bevel opening 19. Bevel opening 19 does not include a suture holding region or recess in its side walls as shown in other embodiments described herein.

Figure 23A:
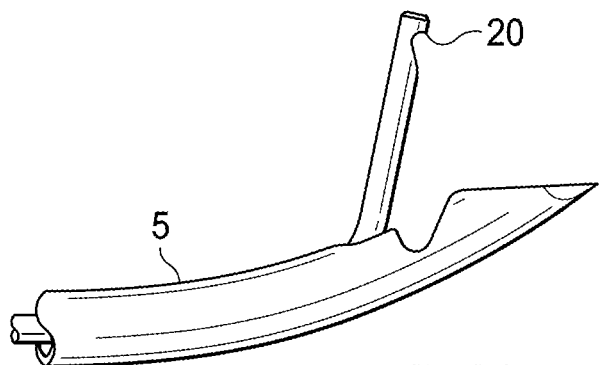
FIGS. 23*a*-23*c* are partial side views of suture manipulating instruments having various wire configurations.
Figure 23B:
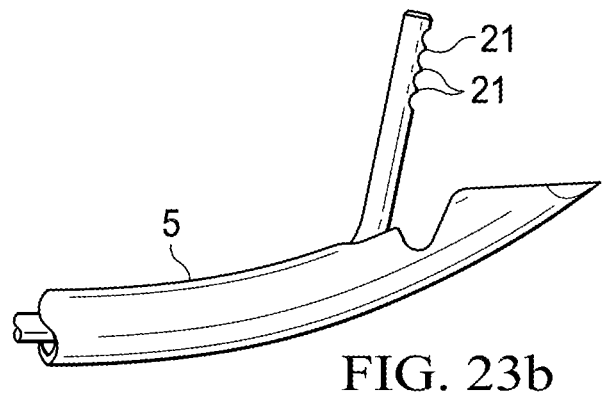
Figure 23C:
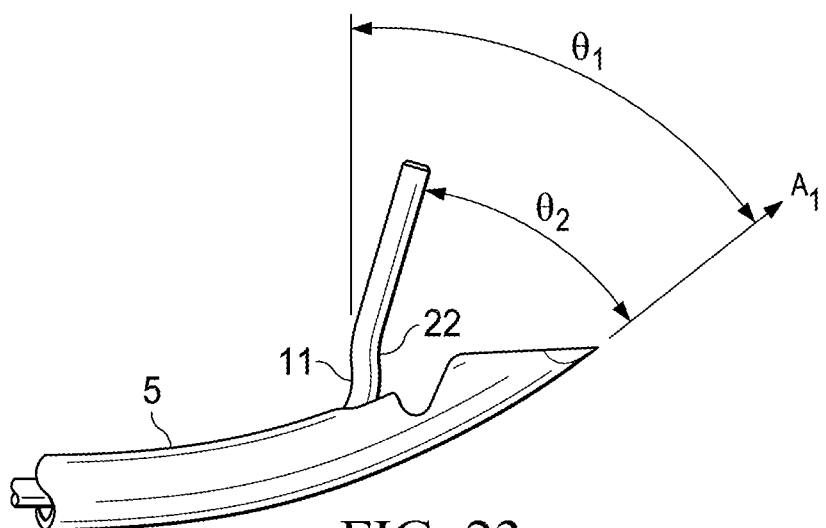

The distal end of the inner member can be configured into a variety of profiles including, but not limited to those illustrated in FIGS. 23a-23c. FIG. 23a shows the inner member as a single wire having a single tooth 20 proximal to the tip of the inner wire. FIG. 23b shows the inner wire with multiple teeth 21 proximal to the tip of the wire. The teeth pattern can be added to improve hold strength on the suture. Other options to improve grip on the suture include, but are not limited to surface treatments of the wire that may add or remove material to roughen the surface of the wire. The height of the teeth may range from 0.1-0.5 mm depending on the size of the inner member.

FIG. 23c shows another possible configuration for the working end of the inner wire in which the wire has two or more bends at the working end. In this instance the wire is configured with a first bend 11 and a second bend 22. First bend is shown being proximal to second bend 22. Preferably, but not necessarily, the first bend is proximal to the tip of the inner wire 6 by a first distance ranging from 2-7 mm. Preferably, but not necessarily, the second bend is proximal to the tip of the inner wire 6 by a second distance ranging from 0.5-3 mm.

First and second bends are shown forming angles $\theta_1$ and $\theta_2$ with the needle axis A1, respectively. $\theta_2$ is less than $\theta_1$. $\theta_1$ preferably ranges from 30-90 degrees. $\theta_2$ preferably ranges from 0-45 degrees.

Figure 24A:
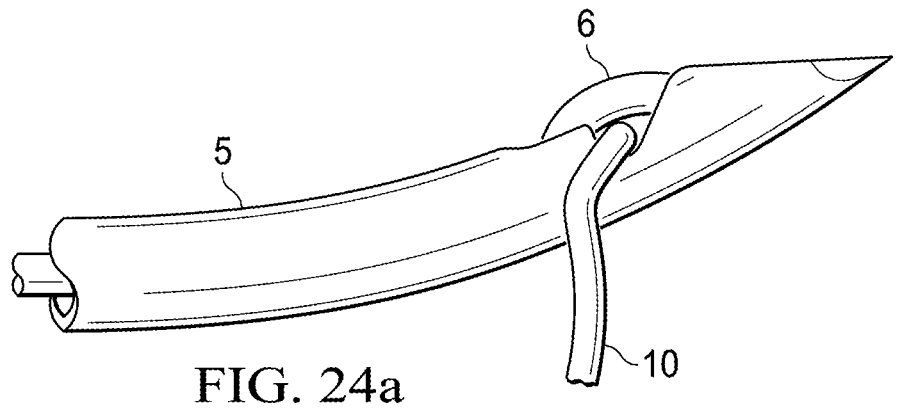
FIGS. 24*a*-24*b* are side and cross sectional views respectively of the working end of a suture manipulating instrument in a retracted configuration.
Figure 24B:
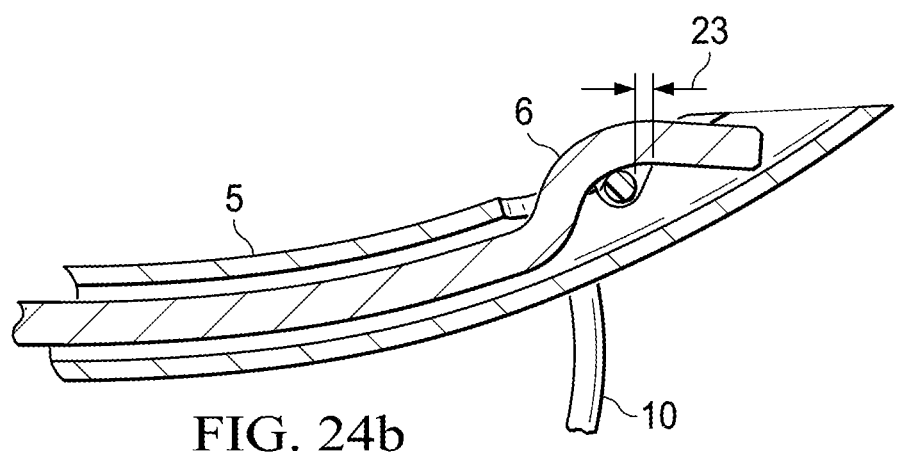

This configuration of the instrument can be used to produce a gap, space or clearance 23 between the inner wire, suture, and needle to allow the suture to slide while still being trapped in the working end for suture manipulation as shown in FIGS. 24a-24b.

In embodiments, the inner member is sufficiently flexible such that further retraction of the needle further clamps the suture within the slot such that the suture may not slide. The instrument in such embodiments comprises an extended configuration, a suture lock or clamping configuration, and an intermediate suture sliding configuration as shown in FIGS. 24a-24b.

Figure 27C:
FIGS. 27c-27d are side and cross sectional views respectively of the working end of the suture manipulating instrument shown in FIGS. 27a-27b in a suture grasping configuration.
Figure 27D:
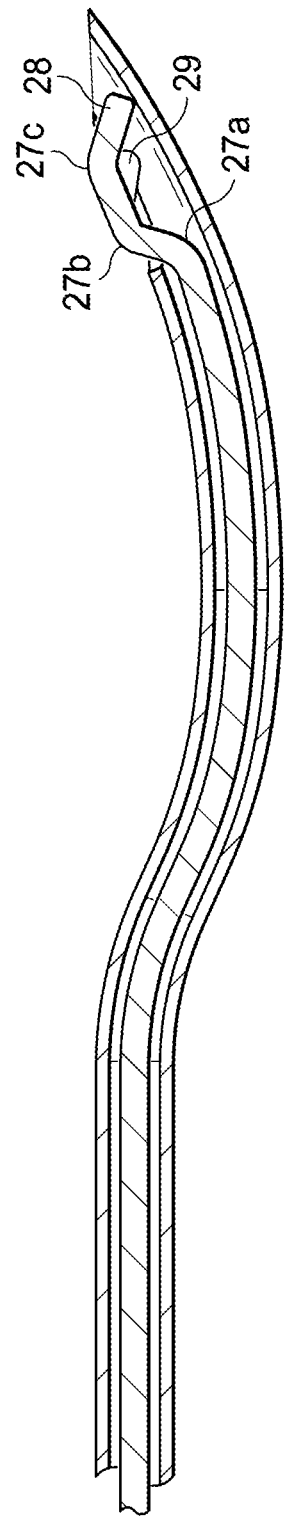
Figure 28A:
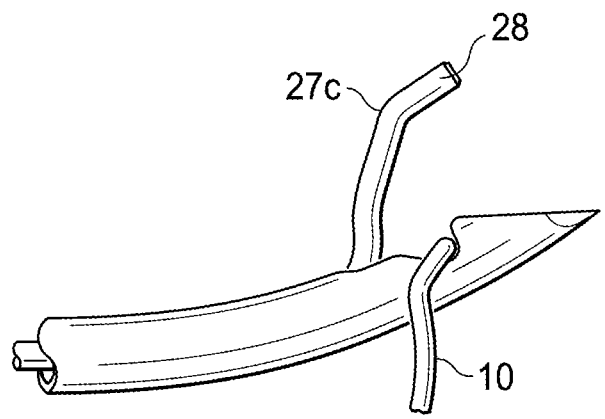
FIGS. 28a-28b are side views of the working end of another suture manipulating instrument in an extended configuration and a suture grasping configuration respectively.
Figure 28B:
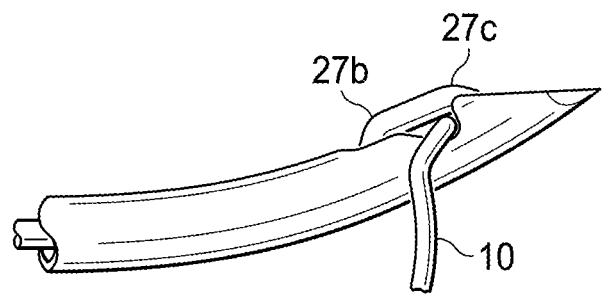
Figure 28C:
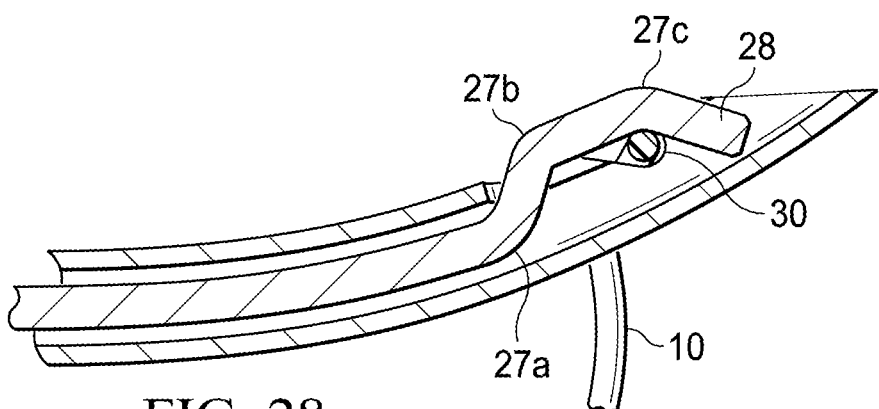
FIG. 28c is an enlarged cross sectional view of the suture instrument holding the suture shown in FIG. 28b.

With reference to FIGS. 27 to 28, a working distal section of an inner member is shown including three bends, 27a, 27b, and 27c. The $3^{rd}$ bend 27c being positioned near or at the distal tip. Wire member also includes a straight portion 28.

The implementation of multiple bends may be used to facilitate suture sliding. For example, while in the retracted state shown in FIGS. 27d and 28c, the working end of the inner wire and the needle slot could constrain the suture 10 while providing a clearance 29 and 30, respectively, necessary to allow the suture 10 to slide.

Further retracting the inner wire would force the wire to close further thereby pinning the suture. Consequently, in accordance with certain embodiments of the invention, a suture instrument is operable in a plurality of configurations including 1) a deployed or extended configuration in which the inner member extends from the needle creating a space between the inner member and needle, 2) an intermediate or suture sliding position in which the inner member is retracted to a degree such that the suture is slidably held across the needle slot, and 3) a pinned or suture clamped configuration in which the inner member is more fully retracted such that the suture is compressed into the slot and in a tortuous manner to firmly grasp the suture and prevent the suture from sliding. Amongst other things, adding multiple bends to the inner member serves to facilitate in deployment or retraction when implemented with various needle shapes.

Manufacture

The needle can be constructed from a variety of materials or combinations of materials, including but not limited to metals such as stainless steel and titanium, plastics such as polycarbonate and PEEK, or shape memory or super elastic Nitinol.

Similarly, the inner wire can be constructed from a variety of materials or combinations of materials, including but not limited to metals such as stainless steel and titanium or plastics such as polycarbonate and PEEK. The preferred embodiment is shape memory or superelastic Nitinol.

The working end of the needle and inner member preferable has circular cross-sections, though other cross-sectional shapes might also be employed. Other shapes include but are not limited to square, rectangular and ovalized cross-sections.

Figure 25:
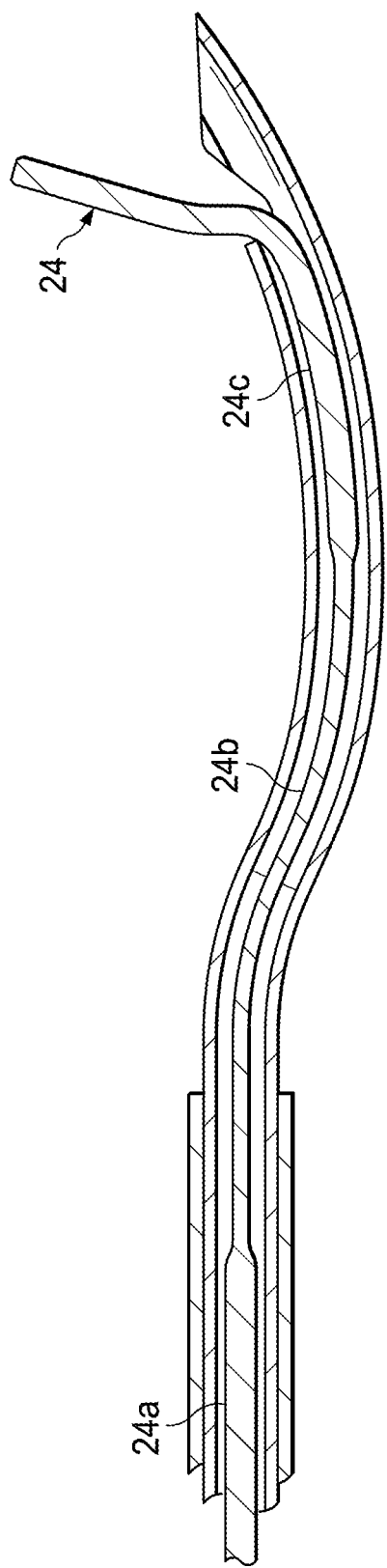
FIG. 25 is a cross sectional view of the working end of another suture manipulating instrument in an extended configuration.

The cross-sectional area of the inner member may be constant or vary along its length. For example, the inner member can be round at the proximal end and flat at the distal end. The inner member may start off at one diameter and taper down to a lower diameter. FIG. 25, for example, shows an embodiment of the invention comprising an inner member 24 having a proximal section or first diameter section 24a, a second or reduced diameter section 24b, and a third most distal section having an enlarged diameter 24c. In embodiments, the diameter of the inner member ranges from 0.75-2 mm. In embodiments, the ratio of the diameter of section 24a to section 24b ranges from 25-75%.

Figure 26:
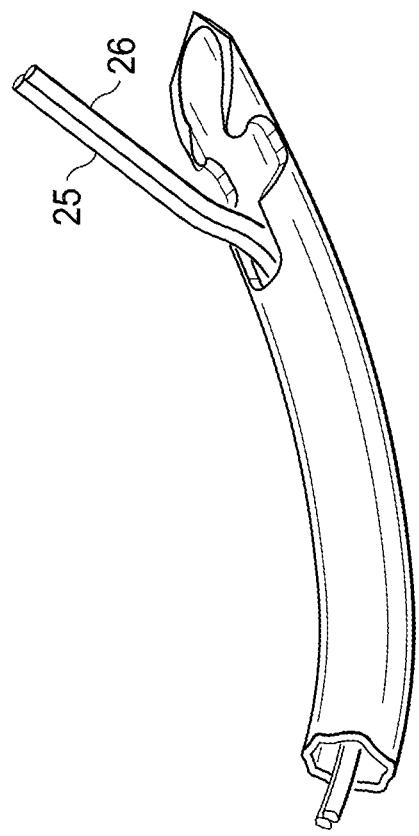
FIG. 26 is a perspective view of the working end of another suture manipulating instrument in an extended configuration.

The inner member can be a single wire or filament. Additionally, the inner member may comprise a wire bundle including two or more wires as shown in FIG. 26. For example, two wires 25 and 26 may be used to perform the same function as a single larger wire member. Implementing multiple wires would allow the wires to translate more easily through the needle while maintaining the rigidity necessary to retain suture. The wires can be attached or detached at the ends or along the length of the wire by adhesives, bonds, fusing, and other attachment techniques known to those of skill in the art.

Figure 29A:
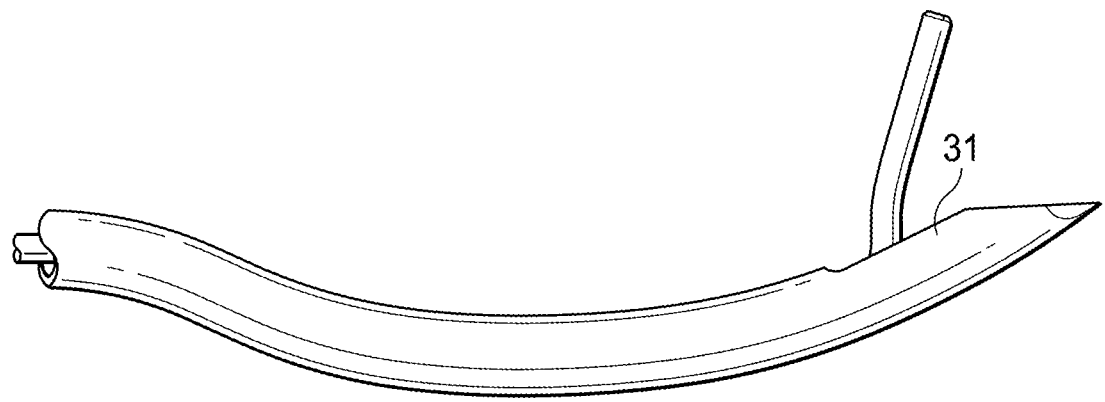
FIGS. 29a-29b are side and perspective views respectively of the working end of another needle distal section and inner member in an extended configuration.
Figure 29B:
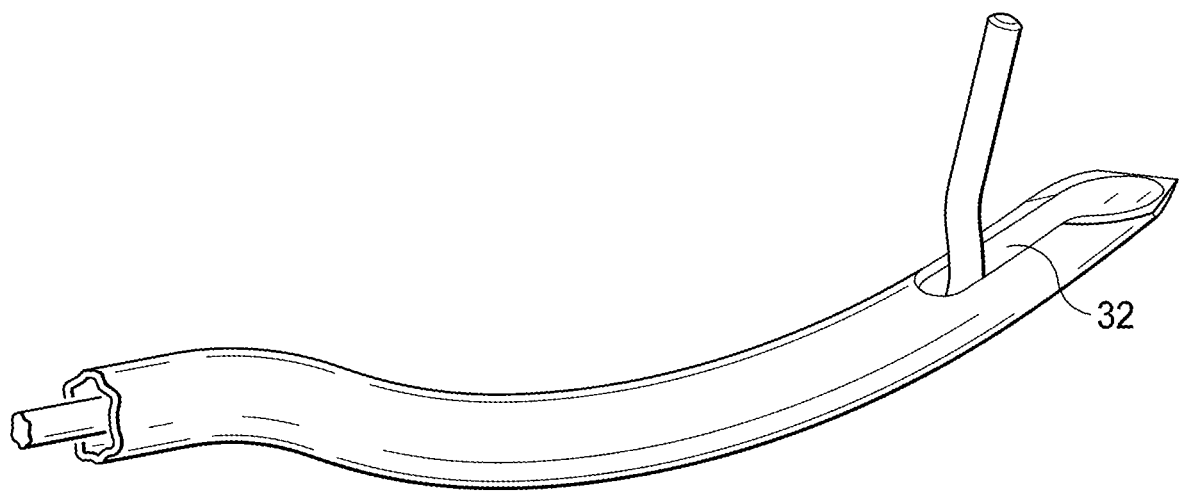

As described herein the working end of the needle may have a wide variety of shapes and configurations. FIGS. 29a-b show a needle body distal section 31 comprising a single slit 32 which would allow the inner wire to deploy from the needle. Single slit 32 preferably, but not necessarily, is wide enough to allow suture to engage with the inner wire and needle in a similar manner to that illustrated in FIGS. 6 and 7. Single slit 32 differs from some of the needle configurations described herein in that a suture holding region or recess in the needle walls is absent in the single slit (e.g., single slit lacks the suture holding region 16 of FIG. 22a).

Figure 30A:
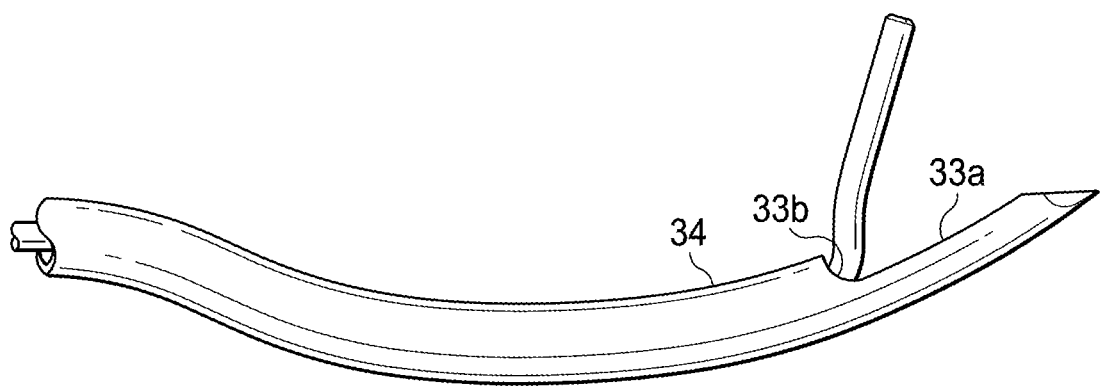
FIGS. 30a-b are side and perspective views respectively of the working end of another needle distal section and inner member in an extended configuration.
Figure 30B:
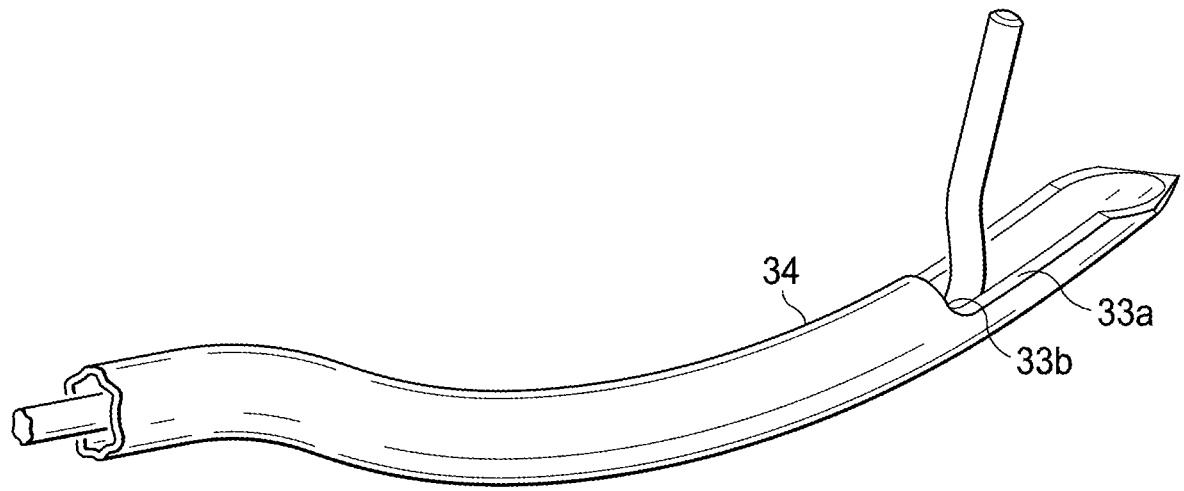
Figure 30C:
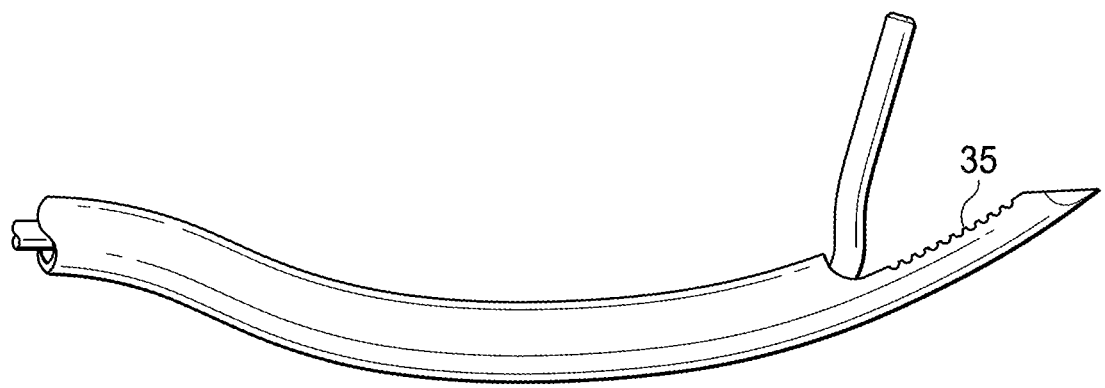
FIG. 30c is a side view of the working end of another needle distal section and inner member in an extended configuration.

FIGS. 30a-30b show a working end of the needle body 34 comprising a single cutoff 33a with a shoulder 33b. This configuration would allow relief for the inner wire while still providing a constraining path for the suture (see, e.g., FIGS. 6 to 7). Additionally, as shown in FIG. 30c, the cutoff may have serrations 35, a roughened surface via for example a surface treatment, or another grip feature in order to provide added suture retention force.

Figure 31A:
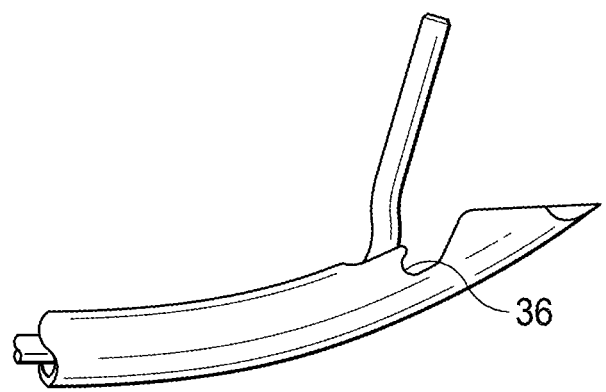
FIG. 31a is a side view of the working end of another needle distal section and inner member in an extended configuration having a proximal undercut.
Figure 31B:
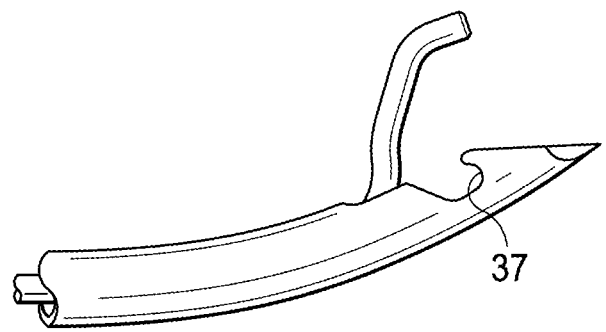
FIG. 31b is a side view of the working end of another needle distal section and inner member in an extended configuration having a distal undercut.
Figure 31C:
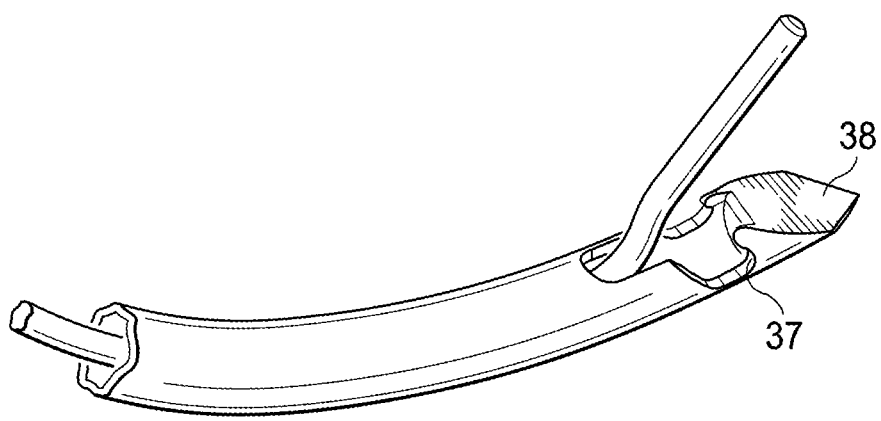
FIG. 31c is a perspective view of the working end of another needle distal section and inner member in an extended configuration having a distal undercut.

FIGS. 31a-31c illustrate additional possible configurations for the suture slot at the working end of the needle in which a hook or undercut may be used to facilitate suture retention and or manipulation. FIG. 31a shows a suture slot with a proximal hook/undercut 36. The undercut 36 is formed in the wall of the needle body. Inner member is shown having two bends in this embodiment.

FIG. 31b shows a suture slot comprising a distal hook/undercut 37. Inner member is shown having three bends in this embodiment.

In embodiments, the needle may comprise a hollow or solid tip or end. FIG. 31c shows a suture slot with a distal hook/undercut 37 and a solid needle tip 38. The solid tip may facilitate tissue penetration. The solid tip may also work in conjunction with the inner wire to form clearance for suture sliding with or without multiple bends at the working end of the inner wire. The solid tip can be formed by a variety of methods including but not limited to filling in the needle tip with a solder or epoxy. A plastic rod can be bonded or mechanically attached within the inner diameter of the needle to form the solid tip. A metal rod can also be welded, bonded or mechanically attached within the inner diameter of the needle to form the solid tip.

The inner member shown in FIG. 31c includes two bends. However, as described herein the inner member may have one or more bends depending on the desirability of suture clamping force, and whether an intermediate suture sliding position is desired.

Figure 32A:
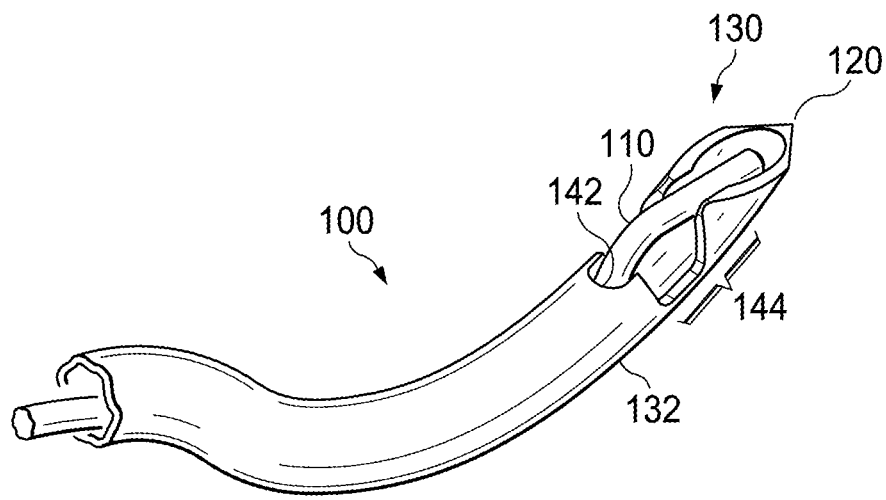
FIGS. 32a-32b are perspective and side views respectively of the working end of another needle distal section and inner member in a retracted configuration.
Figure 32B:
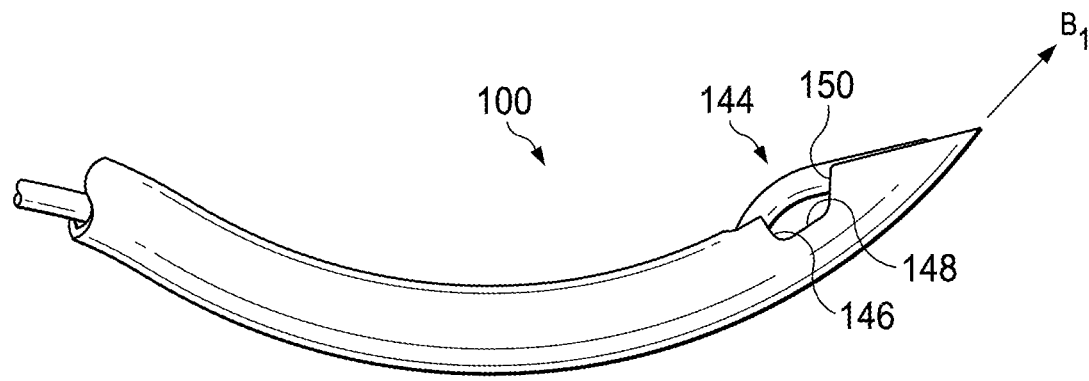
Figure 32C:
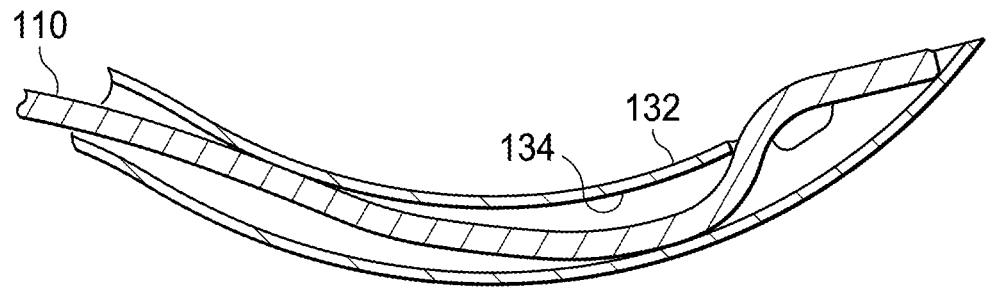
FIG. 32c is a cross sectional view of the needle distal section and inner member shown in FIG. 32b.

FIGS. 32a-32c illustrate another embodiment of a distal section of a needle 100 and inner member 110 in a retracted configuration. The distal section of the needle comprises a needle body 132 having a gently curved crescent shaped profile, a sharpened distal tip 120, and a lumen 134 extending therethrough.

As described herein the inner member 110 is operable to move from a retracted position to a deployed or extended position from the needle body. A suture not shown may be clamped or grasped between the inner member and needle when the inner member is in the retracted position.

The embodiment shown in FIGS. 32a-32c includes a suture slot 130. The suture slot 130 comprises a plurality of sections including a wire relief section 142, and a suture holding section 144. The inner member 110 is shown in a retracted position, and has an inner member tip portion disposed within slot 130.

With reference to FIG. 32b, suture holding section 144 is shown as a recess in the side walls or body of the needle 100. Suture holding section 144 comprises a proximal shoulder or surface 146, a base or trough section 148, and a distal ramp 150. The dimensions and angles and of the features are preferably in the range as described herein such as but not limited to the embodiments shown in FIG. 22.

As described herein, the suture holding region 144 serves to clamp the suture when the inner member is retracted. The degree of clamping may be bolstered by modifying the design including for example, material selection, increasing the width of the trough 148, increasing the number of bend angles present in the inner member, or increasing the degree of the bend angles of the inner member.

Additionally, suture release form the instrument may be facilitated by, amongst other things, decreasing the distal ramp angle so as to allow the suture to slide more freely out of the virtual jaw grip formed between the needle and the inner member. Many features of the described embodiments may be modified to achieve a desired design, result or application, and such modifications are intended to be part of the invention. The invention is intended only to be limited as set forth in the appended claims.

FIGS. 33-36 illustrate various constraining features to further hold the inner member, trapping the suture, when the suture instrument is in the retracted suture-clamping configuration.

Figure 33A:
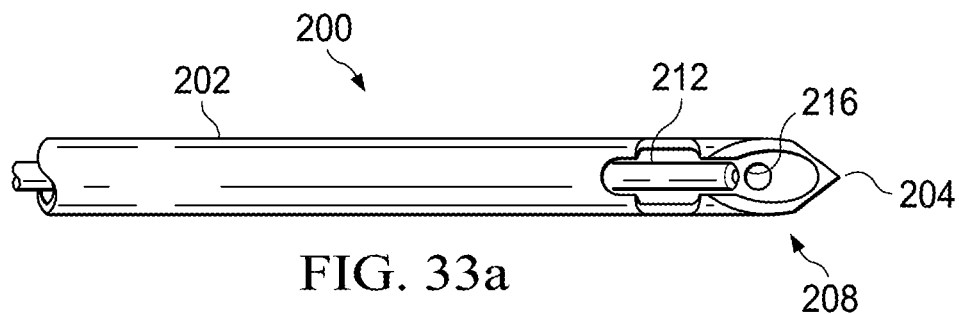
FIGS. 33a-b are top and cross sectional views respectively of the working end of another needle distal section and inner member in an extended configuration.
Figure 33B:
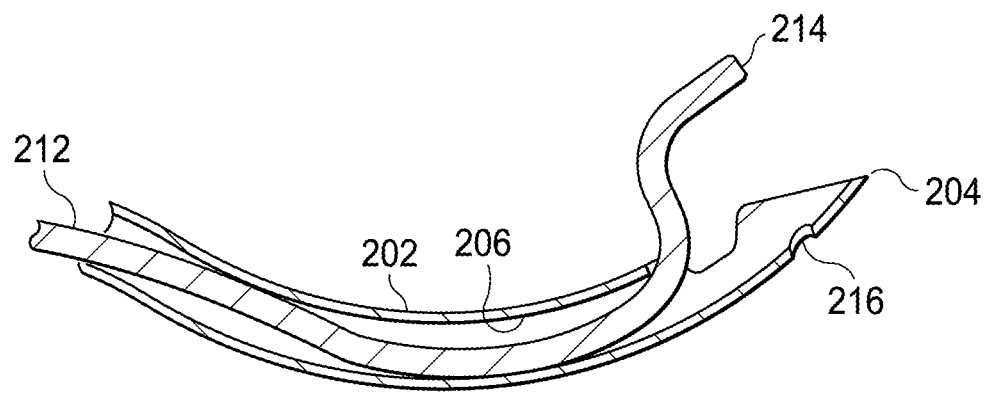

FIGS. 33a-33b illustrate a distal needle section 200 including a needle body 202, a tissue penetrating distal tip 204, a lumen 206 extending therethrough, and a suture slot 208. Inner member 212 is shown having a plurality of bends and in a deployed configuration. Inner member extends away from the needle body. As described herein, spacing the inner member away from the needle body as shown in FIGS. 33a-33b serves to create a space within which the suture (not shown) may be inserted or placed.

Figure 33C:
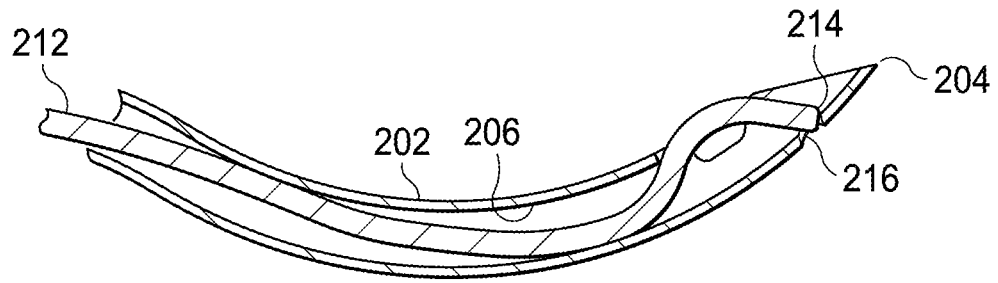
FIG. 33c is a cross sectional view of the needle distal section and inner member shown in FIG. 33b shown in a retracted configuration.

FIG. 33c shows inner member 212 in a retracted configuration. Distal section of the inner member is substantially disposed within the suture slot 208 and in particular, a distal tip or end 214 of the inner member is rotated or manipulated until it is fit within hole or aperture 216 in the needle body 202.

Figure 34A:
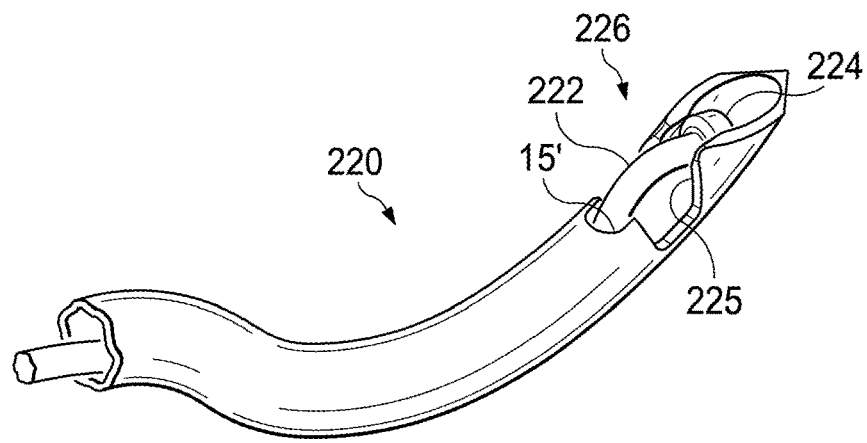
FIG. 34a is a perspective view of the working end of another needle distal section and inner member shown in a retracted configuration.
Figure 34B:
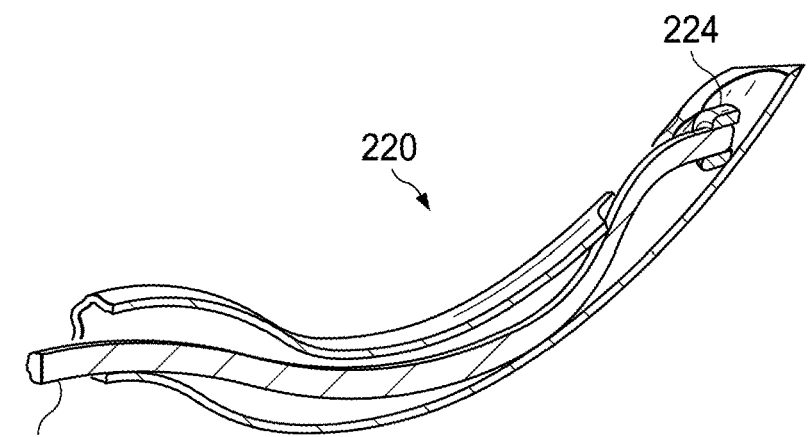
Figure 34C:
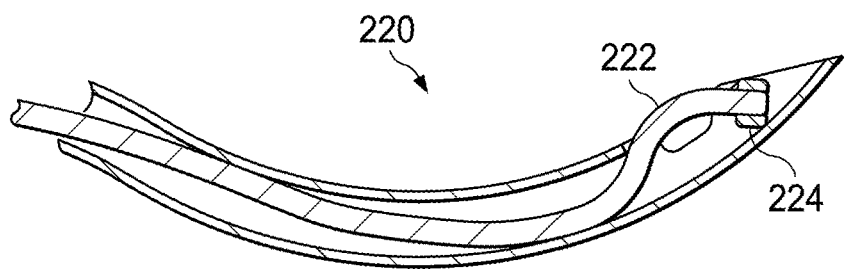
Figure 35A:
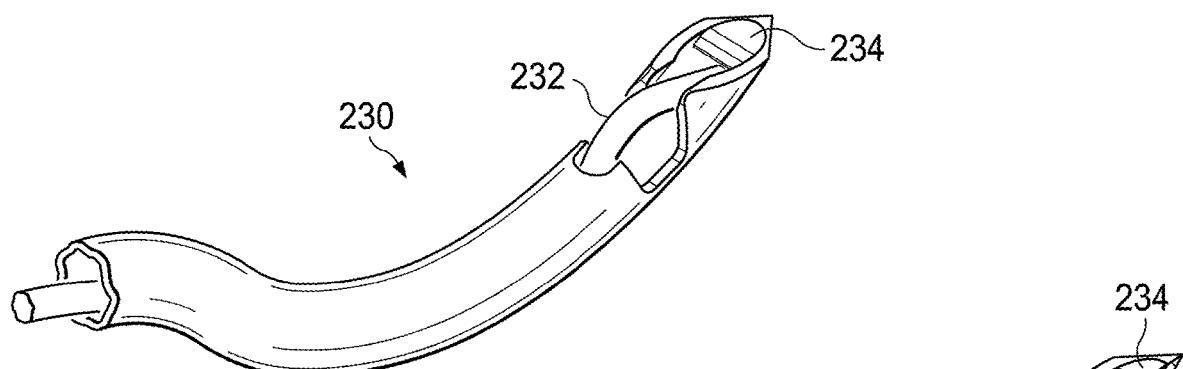
FIG. 35a is a perspective view of the working end of another needle distal section and inner member shown in a retracted configuration.
Figure 35B:
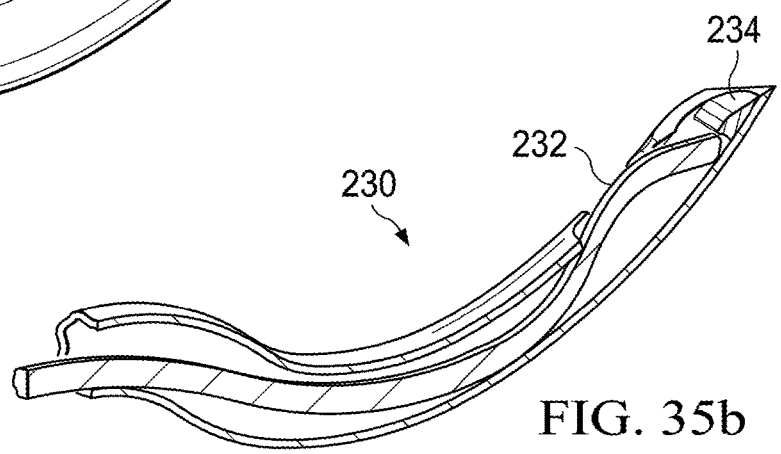
Figure 35C:
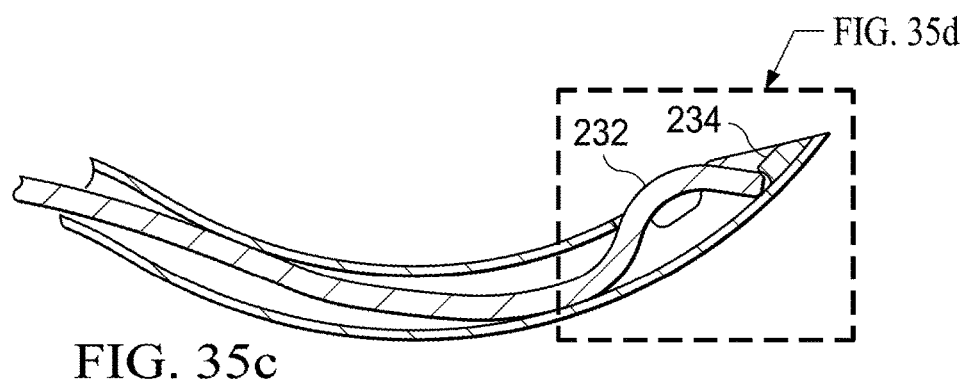
Figure 35D:
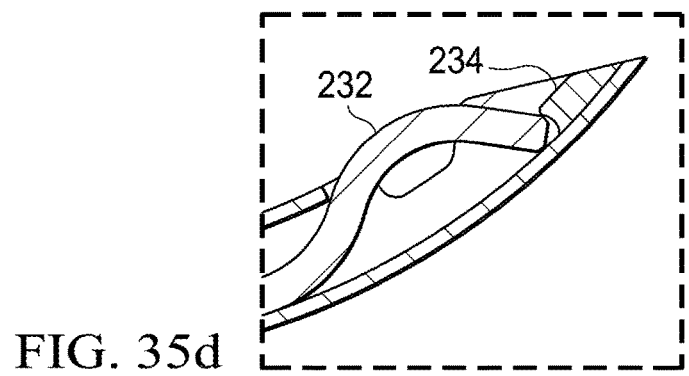
FIG. 35d is an enlarged view of a distal portion of the needle and inner shown in FIG. 35c.

FIGS. 34a-34c show another needle distal section and inner member in a retracted configuration. The embodiment shown in FIGS. 34a-34c differs from that shown in FIGS. 33a-33c in that the embodiment shown in FIGS. 34a-34c includes a ferrel type constraining feature. In particular, ferrel 224 comprises a cylindrical body having a cavity to receive the tip of the inner member 222. Ferrel 224 may be bonded or otherwise affixed within the slot 226 of the needle section. The ferrule 224 is attached to the wire 222 and is pulled into the tube such that the ferrule restricts the wire from being pulled perpendicular to the needle axis by having a larger diameter than the width of the narrowed portion (or neck 225) of the suture slot 226.

FIGS. 35a-35d show another needle distal section 230 and inner member 232 in a retracted configuration. The embodiment shown in FIGS. 35a-35d differs from that shown above in that the embodiment shown in FIGS. 35a-35d includes a cleat type constraining feature 234. Cleat 234 includes an abutment surface or lip which snugly holds the distal end of the inner member when the inner member is retracted.

Figure 36A:
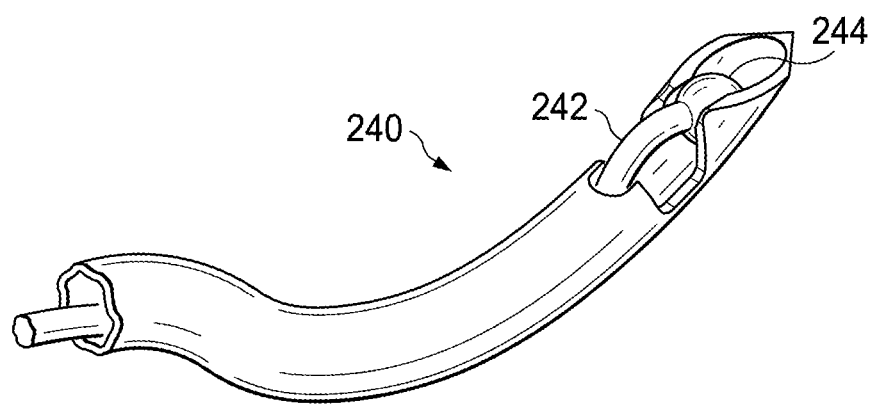
FIG. 36a is a perspective view of the working end of another needle distal section and inner member shown in a retracted configuration.
Figure 36B:
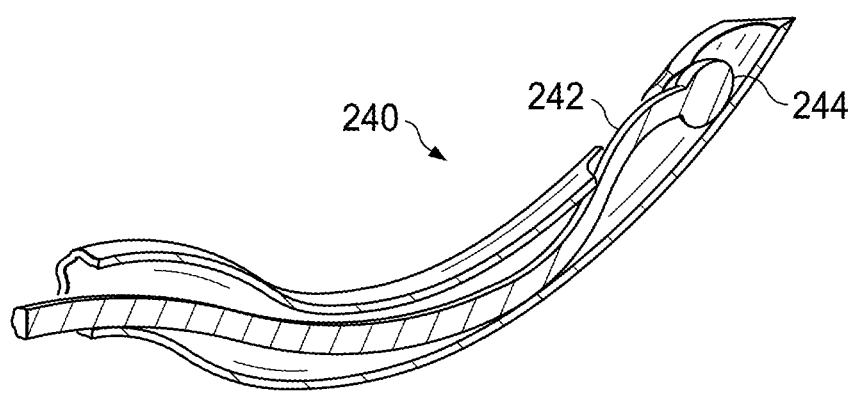
Figure 36C:
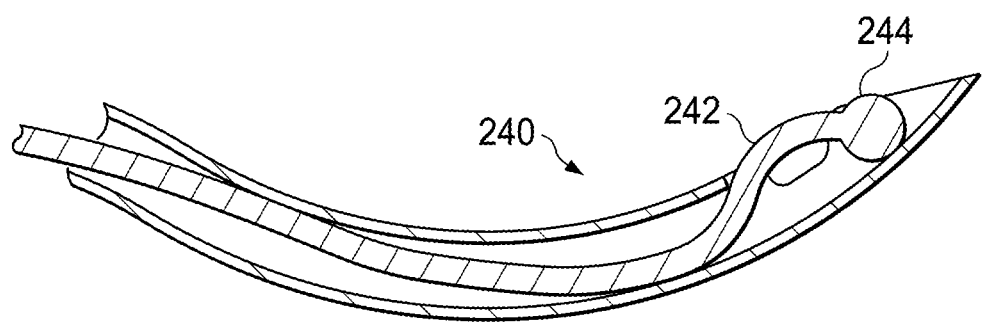

FIGS. 36a-36c show another needle distal section 240 and inner member 242 in a retracted configuration. The embodiment shown in FIGS. 36a-36c differs from that shown above in that the embodiment shown in FIGS. 36a-36c includes a bulbous constraining feature 244. In particular, the inner member 242 terminates in a rounded spherical shape 244. The bulb snugly fits within the needle slot (e.g., by interference fit). Bulb 244 may be bonded or otherwise affixed to inner member, or may be formed as part of the inner member.

The above described constraining features serve to further or redundantly secure inner member within the slot to prevent deployment of the inner member, and to prevent inadvertent release of the suture.

As described herein, embodiments of the invention facilitate suture release from the instrument after the suture has been clamped.

Figure 37:
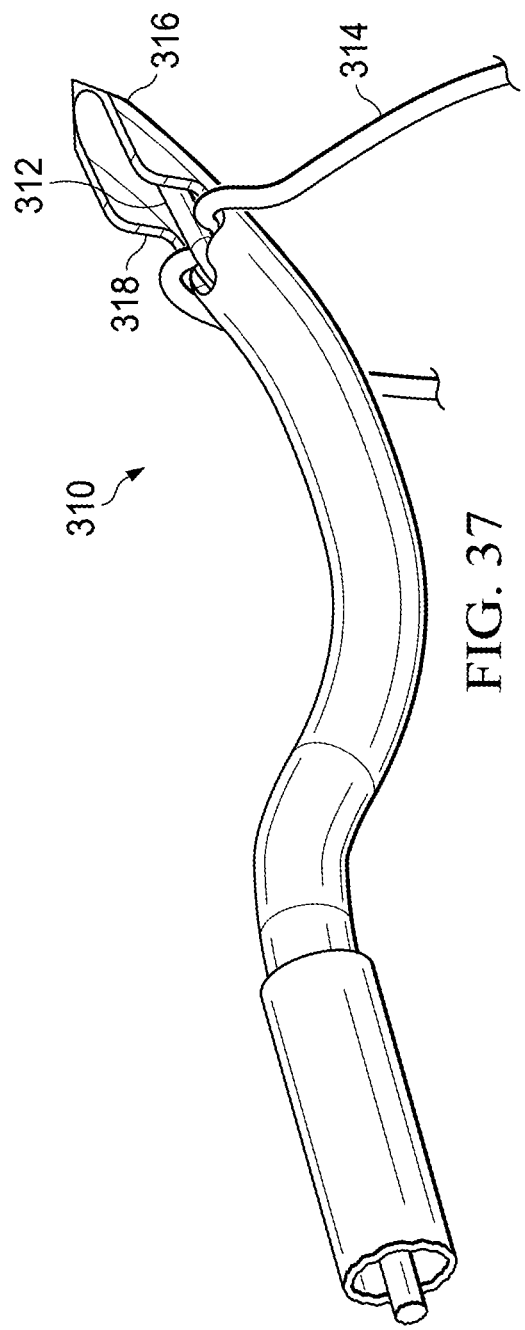
FIGS. 37-38 are perspective and cross sectional views respectively of the working end of a suture manipulating instrument in a suture grasping configuration.
Figure 38:
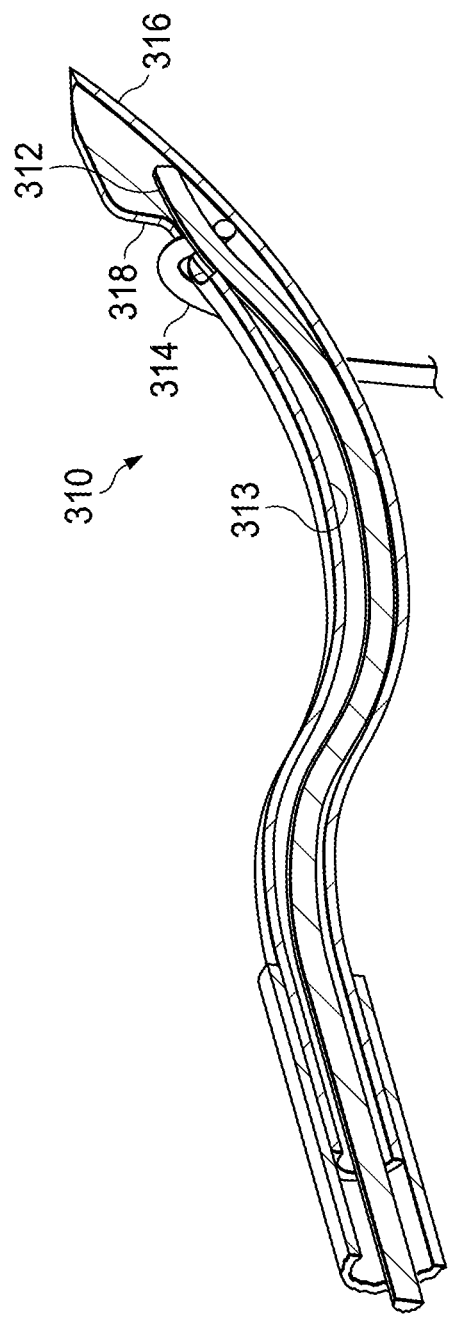

With reference to FIGS. 37-38, perspective and cross sectional views respectively of the working end of a suture manipulating instrument 310 in a suture clamping configuration is shown. Inner member 312 (e.g., a preformed wire) holds suture 314 in place by pinching it against needle 316. To release the suture, inner member 312 is moved distally. This unclamps the pinching force on the suture 314. Sometimes, however, the suture can remain in the suture recess or slot 318 of the needle 316, making it difficult to release the suture when performing an arthroscopic procedure.

In embodiments, the suture is released from the inner member despite the bias to remain in slot 318. With reference to FIGS. 39-40, inner member 312 is shown being retracted in the proximal direction and, as the inner member 312 is retracted, it rides over (and clears) the suture 314. Consequently, the suture remains within suture recess 318 and is not dragged into inner lumen 313. In a sense, the suture 314 is stripped from the inner member 312.

Once inner member is retracted and not pinching suture, the suture is free to move. However, it may still be positioned in the suture recess or slot 318. In embodiments, and as shown in FIG. 41, inner member 312 is pushed distally, thus ejecting the suture 314 out of the suture recess 318.

Figure 42A:
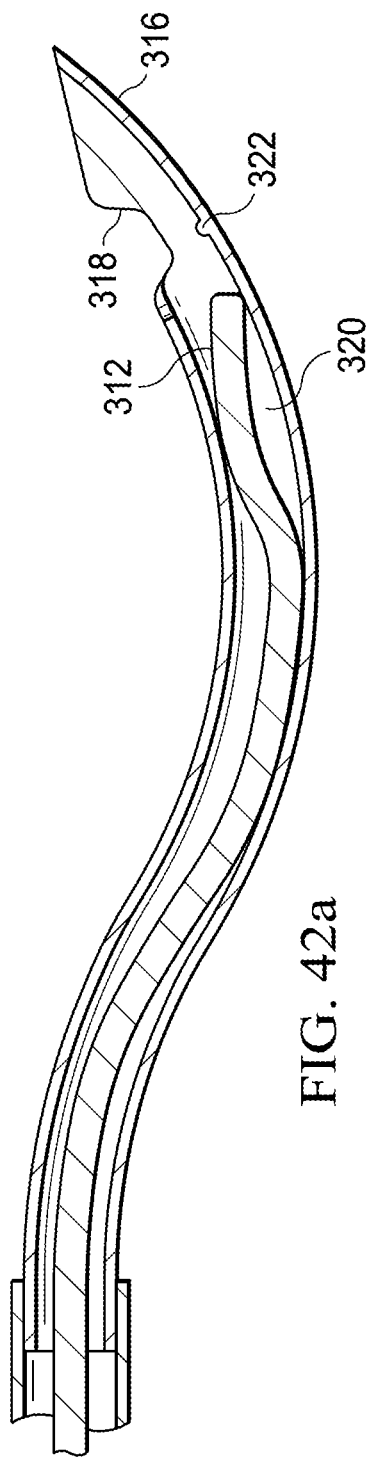
FIGS. 42a-42b are side and perspective views respectively of various needle distal sections in retracted configurations.
Figure 42B:
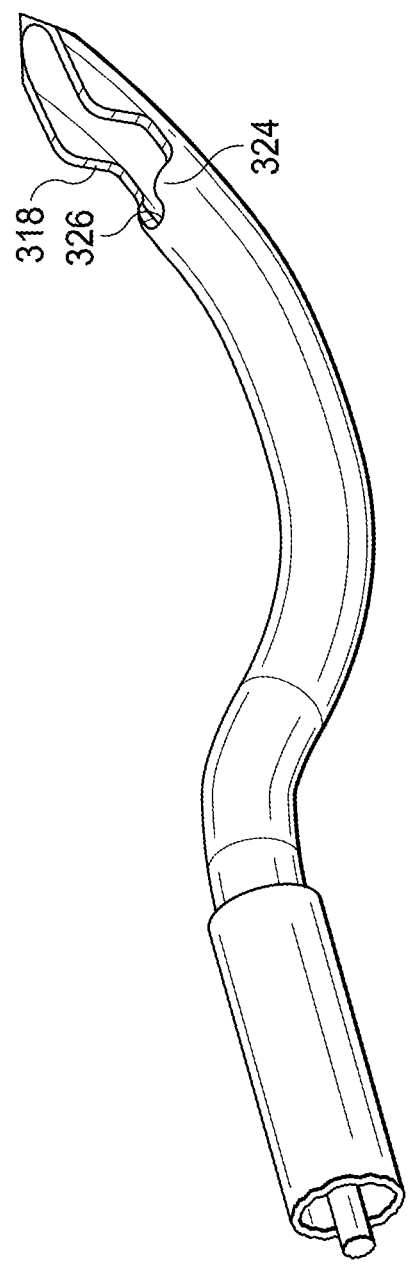

FIGS. 42a-42b show additional features serving to prevent the suture 314 from being drawn or sucked into the inner lumen tube 320. In certain embodiments it is desirable to prevent the suture from being sucked into the lumen 320 because doing so would restrict the ability of the operator to push the suture 314 (e.g., to eject the suture) from the instrument. In the embodiments shown in FIGS. 42a-42b, the size of the opening 326 leading to inner lumen 320 is restricted. In FIG. 42a, for example, a detent 322 is placed in the floor of the needle 316. In FIG. 42b, tabs 324 are deformed near the proximal portion of the opening 326. The features shown FIGS. 42a-42b serve to strip the suture 314 off inner member 312 as the inner member is pulled proximally into the inner lumen 320. The suture may then be more easily released or ejected from the instrument.

It is to be understood that the features described above to assist in stripping the suture from the inner member may vary widely. For example, a stripping means such as a tab or detent may be disposed at one or more locations along the needle lumen. Additionally, the feature may extend up to a full diameter of the inner lumen. Additionally, the feature may extend about the entire circumference. Or, the feature may be limited to an arcuate segment.

A protrusion to strip the suture may be positioned within the lumen, or at the entrance of the lumen. The suture may thus be stripped from the inner member inside the lumen or outside the lumen.

Figure 43:
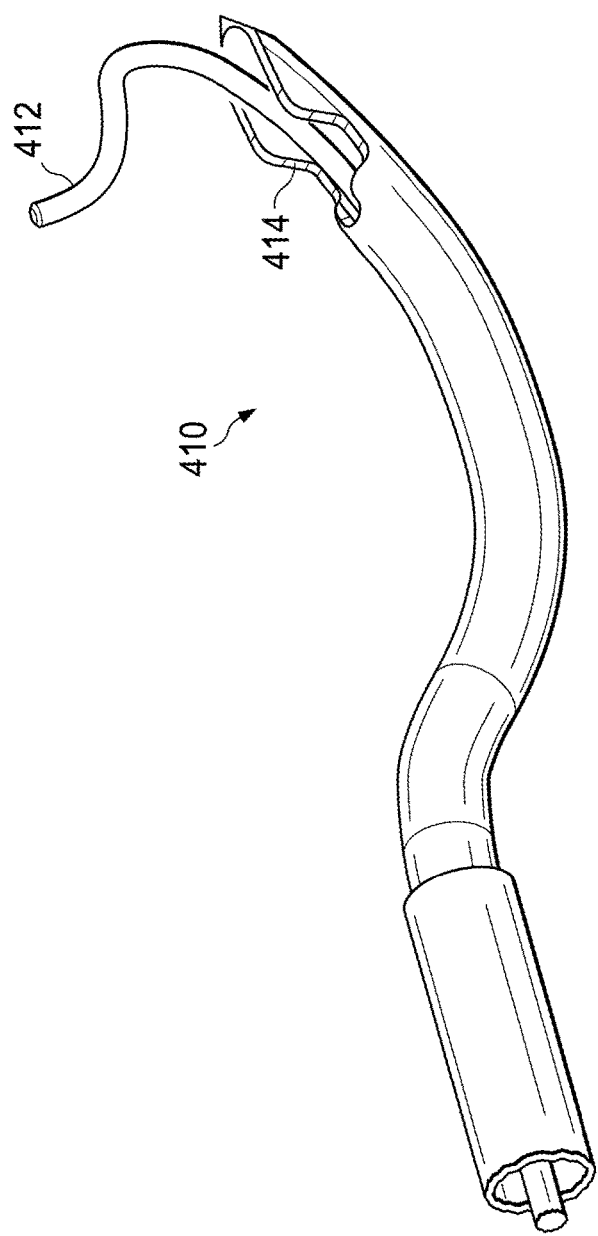
FIGS. 43-44 are perspective and cross sectional views respectively of another needle distal section and inner member shown in an extended configuration.
Figure 44:
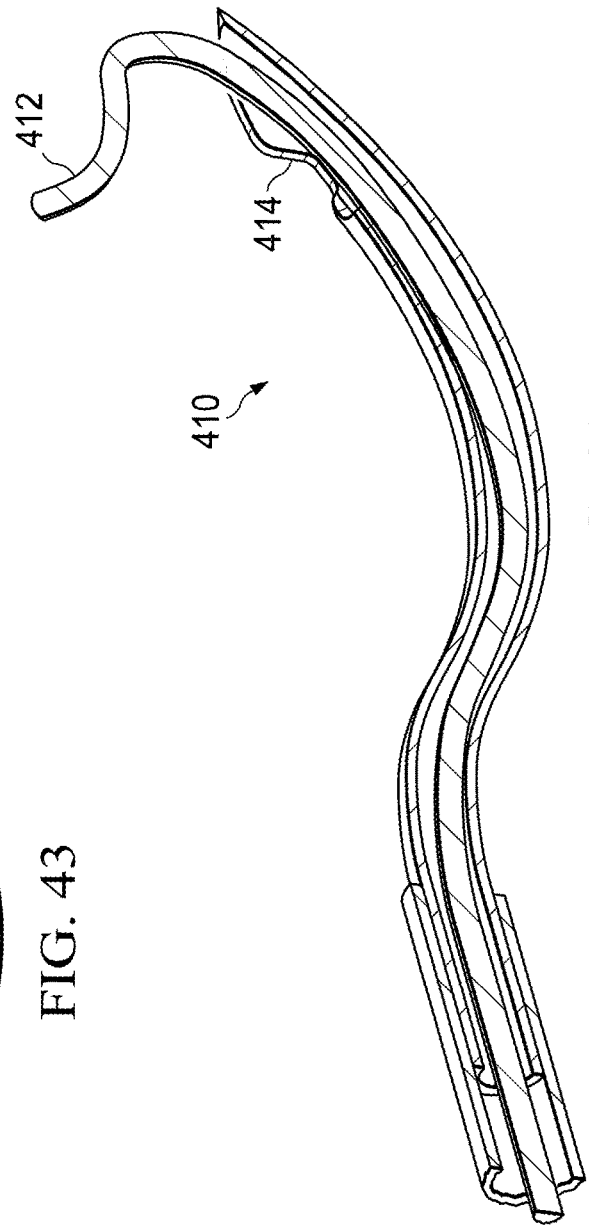
Figure 45:
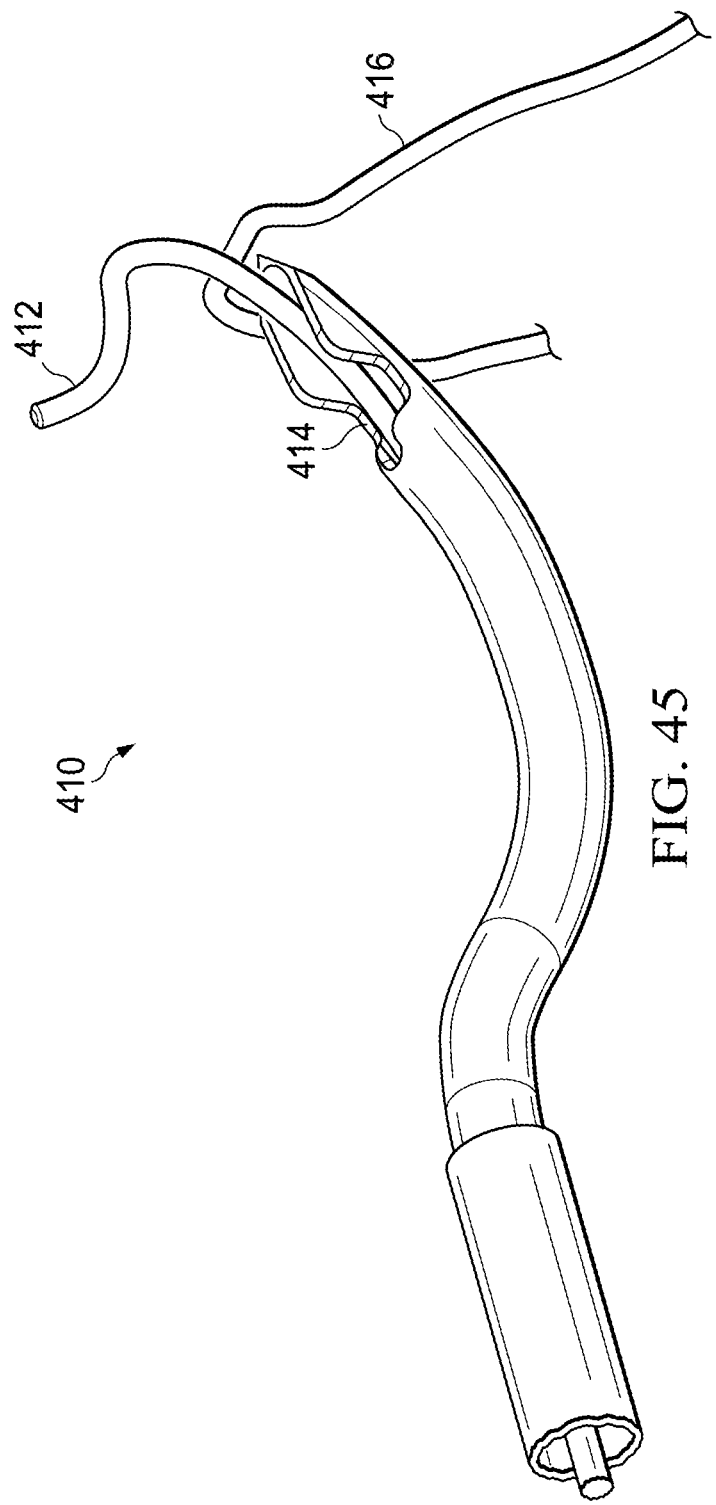
FIG. 45 is a perspective view of the needle distal section, suture, and inner member of FIGS. 43-44, shown in an extended configuration.

FIGS. 43-44 are perspective and cross sectional views respectively of the working end of another needle distal section 410 and inner member 412 shown in an extended configuration. More specifically, FIGS. 43-44 show a perspective and cross-sectional view of an inner member 412 that has been deployed more distally than the embodiments shown in FIGS. 37-42. As described herein, extending the inner member pushes the suture 416 out of the suture recess 414. FIG. 45 shows the suture 416 having been pushed out of the suture slot 414 by the distally deployed inner member 412.

FIGS. 46a-46b show embodiments of an instrument including features serving to facilitate the suture eject (or push-out) method described herein. FIG. 46a, for example, shows inner member 412 having a notch 418. Notch 418 aids in 'grabbing' the suture as the inner member 412 is being deployed distally. FIG. 46b shows another feature to facilitate ejecting or pushing out the suture as the inner member is pushed distally. In particular, FIG. 46b shows a sleeve 420 coaxially surrounding the inner member 412 thus creating a shoulder to catch the suture (not shown).

The features described above to assist in ejecting or pushing the suture may vary widely. For example, a pushing suture means may extend a full or partial diameter, and be located at one or more places along the wire.

Retracting Suture into Needle Lumen

Figure 47:
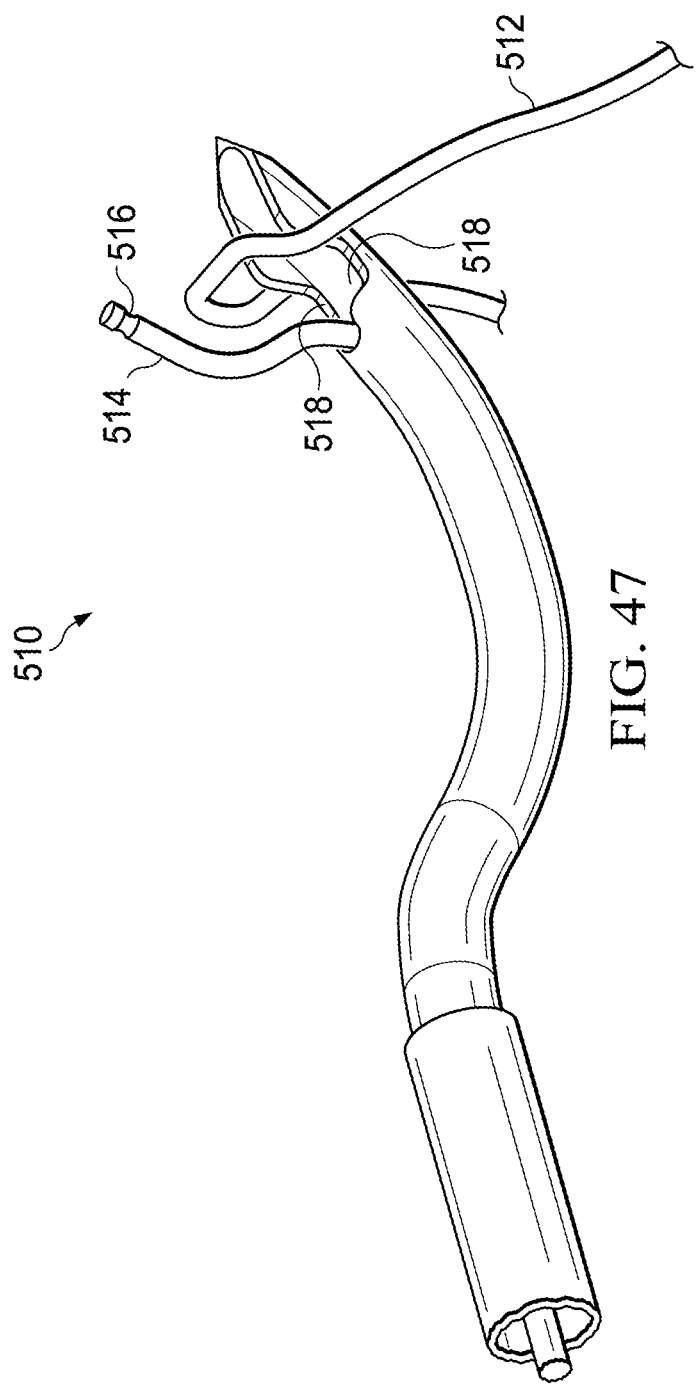
FIG. 47 is a perspective view of another needle distal section, suture, and inner member shown in an extended configuration.

FIG. 47 is a perspective view of the working end of another needle distal section 510 and inner member 514 in an extended configuration. The inner member 514 has been extended, deploying suture 512. The needle 510 and recess 518 may be the same shape as described herein except that the inner member 514 (shown as a wire) has a grasping ring 516 located near the distal end of the inner member.

Figure 48:
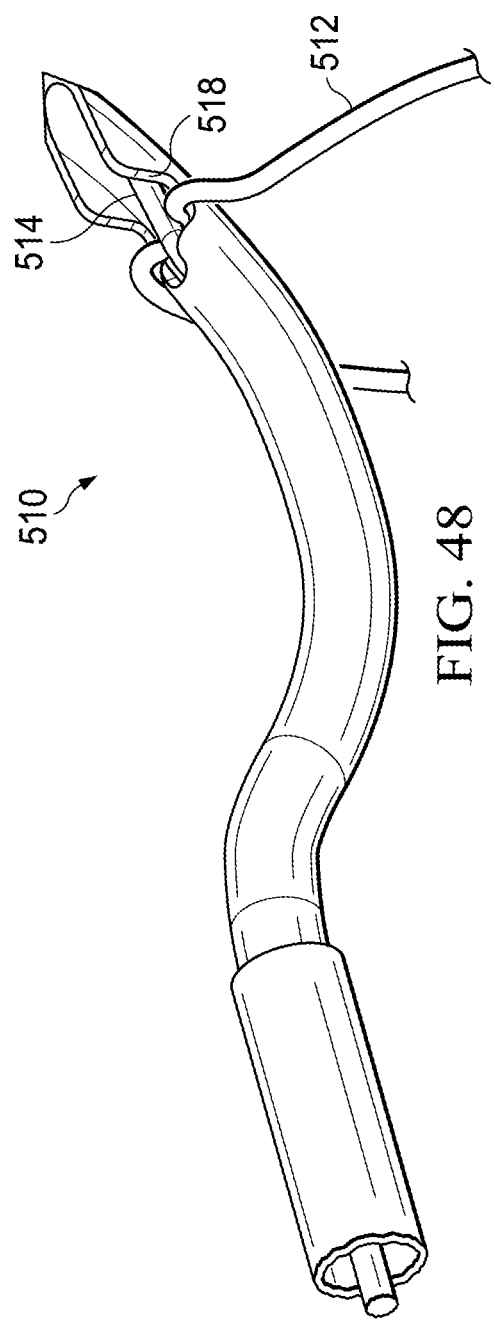
FIGS. 48-49 are perspective and cross sectional views respectively of the working end of a suture manipulating instrument in a suture grasping configuration.
Figure 49:
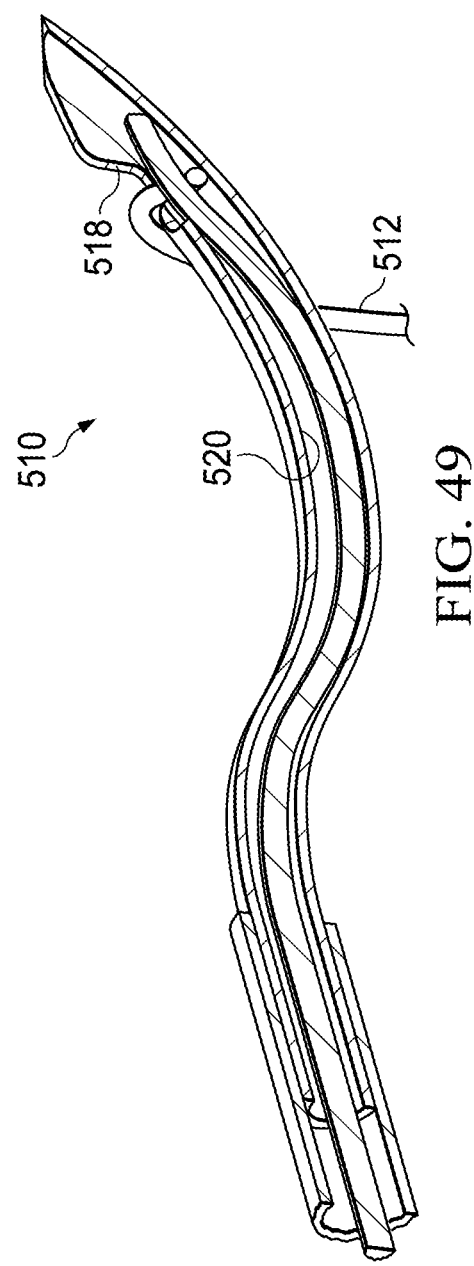

FIGS. 48-49 are perspective and cross sectional views respectively of the working end of the needle 510 shown in a suture grasping configuration. The inner member 514 is shown pinching the suture 512 to hold it in the suture slot 518. As will be described in more detail herein the suture may be subsequently drawn into the inner lumen 520 of needle 510 by further retracting the inner member 514 to a second or more proximal location.

Figure 50:
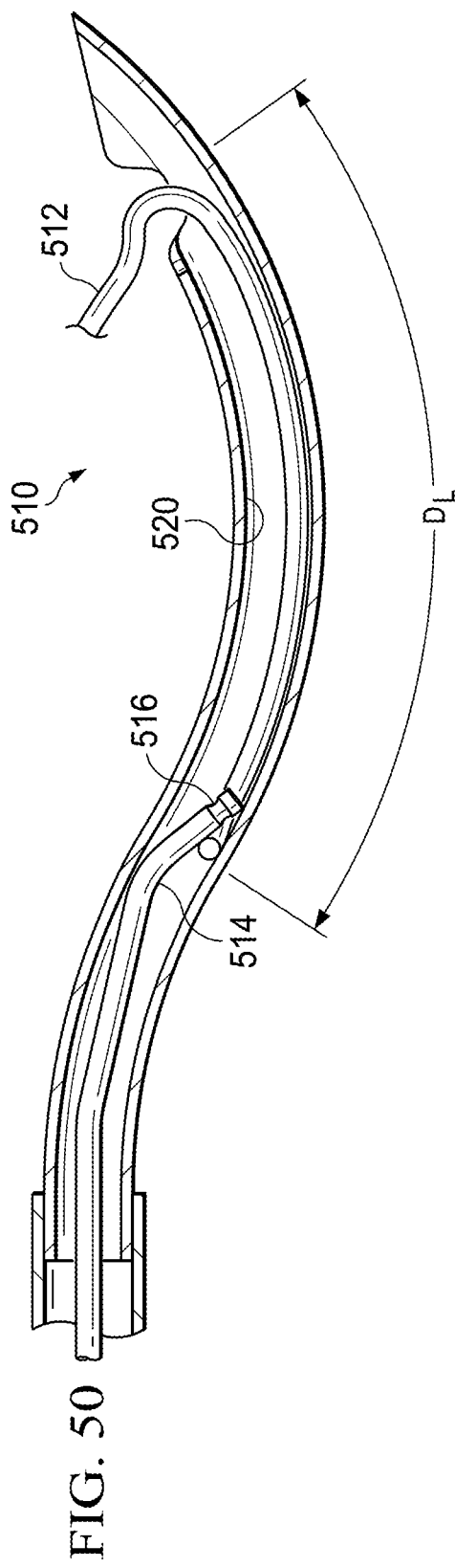
FIG. 50 is a side view of the working end of the suture manipulating instrument shown in FIGS. 48-49, in a further retracted configuration.

FIG. 50 is a cross sectional view of the needle distal section shown in FIGS. 48-49, shown with the inner member in a further retracted configuration. In particular, inner member 514 has been pulled proximally into the inner lumen 520, dragging the suture 512 into the inner lumen with the aid of the grasping ring 516.

Figure 51:
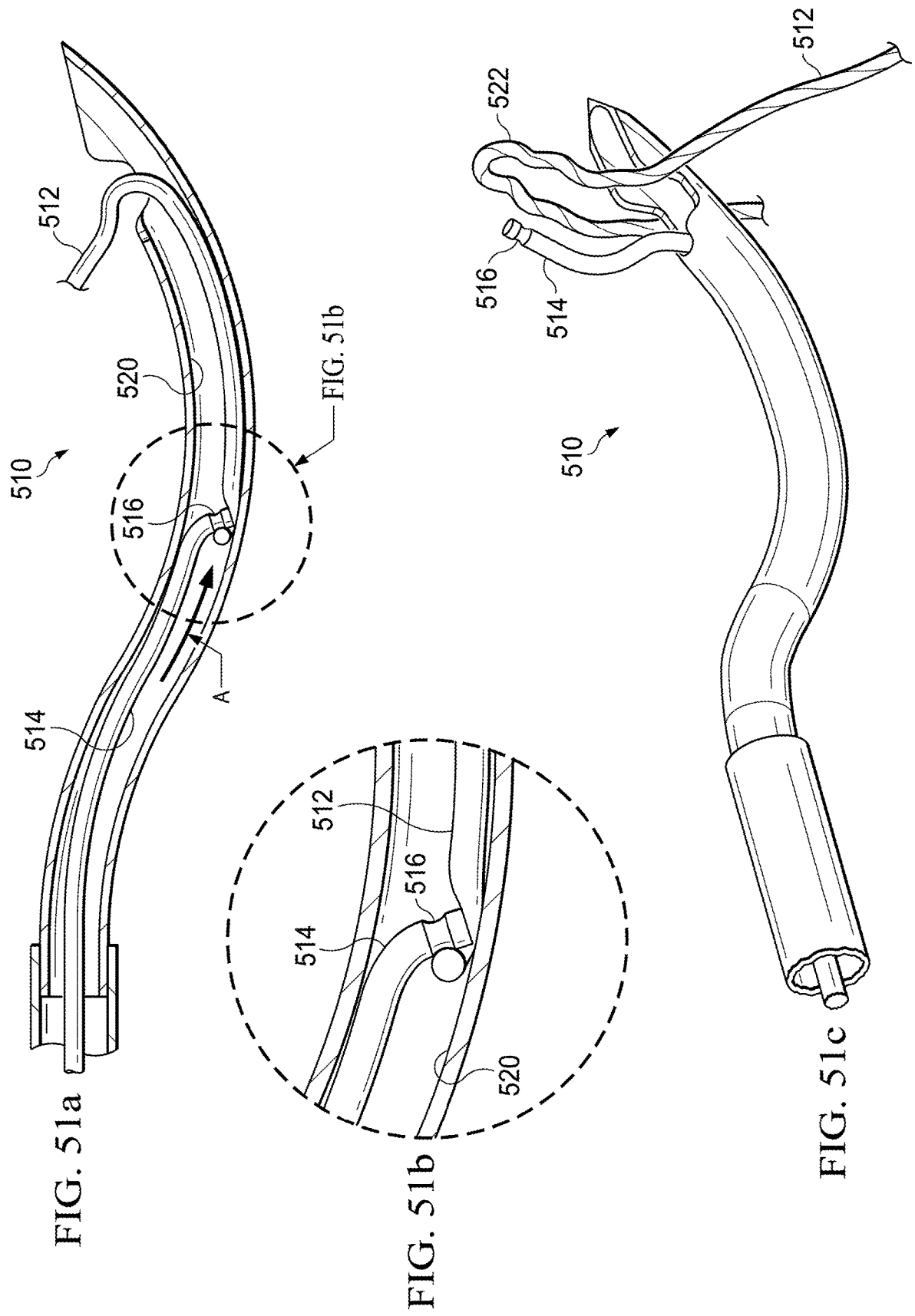
FIG. 51a is a cross sectional view of the needle distal section, suture, and inner member shown in FIG. 50, pushing the suture distally.
FIG. 51b is an enlarged view of the inner member gripping into the suture.
FIG. 51c is a perspective view of the needle distal section, suture, and inner member shown in FIG. 50, in an extended configuration.

FIG. 51a is a cross sectional view of the working end of the needle distal section, suture, and inner member 514 wherein the inner member is shown being moved distally within the lumen 520, and urging the suture in the direction (A).

FIG. 51b shows an enlarged view of a gripping feature 516 acting on the suture 512. In embodiments, the gripping features 516 partially press, compress, cut into, capture and/or pierce the suture. In embodiments, the gripping features may have serrations or corners that the suture fibers stick to, hang up on, or become entangled. These gripping features reliably serve to maneuver the suture 512 proximally and distally, and to eject the suture from the inner lumen 520. Such gripping features may vary widely and include serrations, corners, notches, rings or other structures and geometries.

FIG. 51c is a perspective view of the working end of the needle distal section, suture, and inner member shown in FIG. 50, in an extended or deployed configuration. In particular, FIG. 51c shows the suture 522 having been pushed out of the inner lumen 520 by grasping feature (and or pushing means) 516 located on inner member 514.

FIG. 51c also shows suture having a relatively large suture loop 522. The suture loop 522 is approximately equal to the length of suture ($D_L$) pulled into the inner lumen 520. This relatively large loop 522 is advantageous in arthroscopic surgery because it may be more easily grabbed by a surgeon than a smaller loop.

Figure 52:
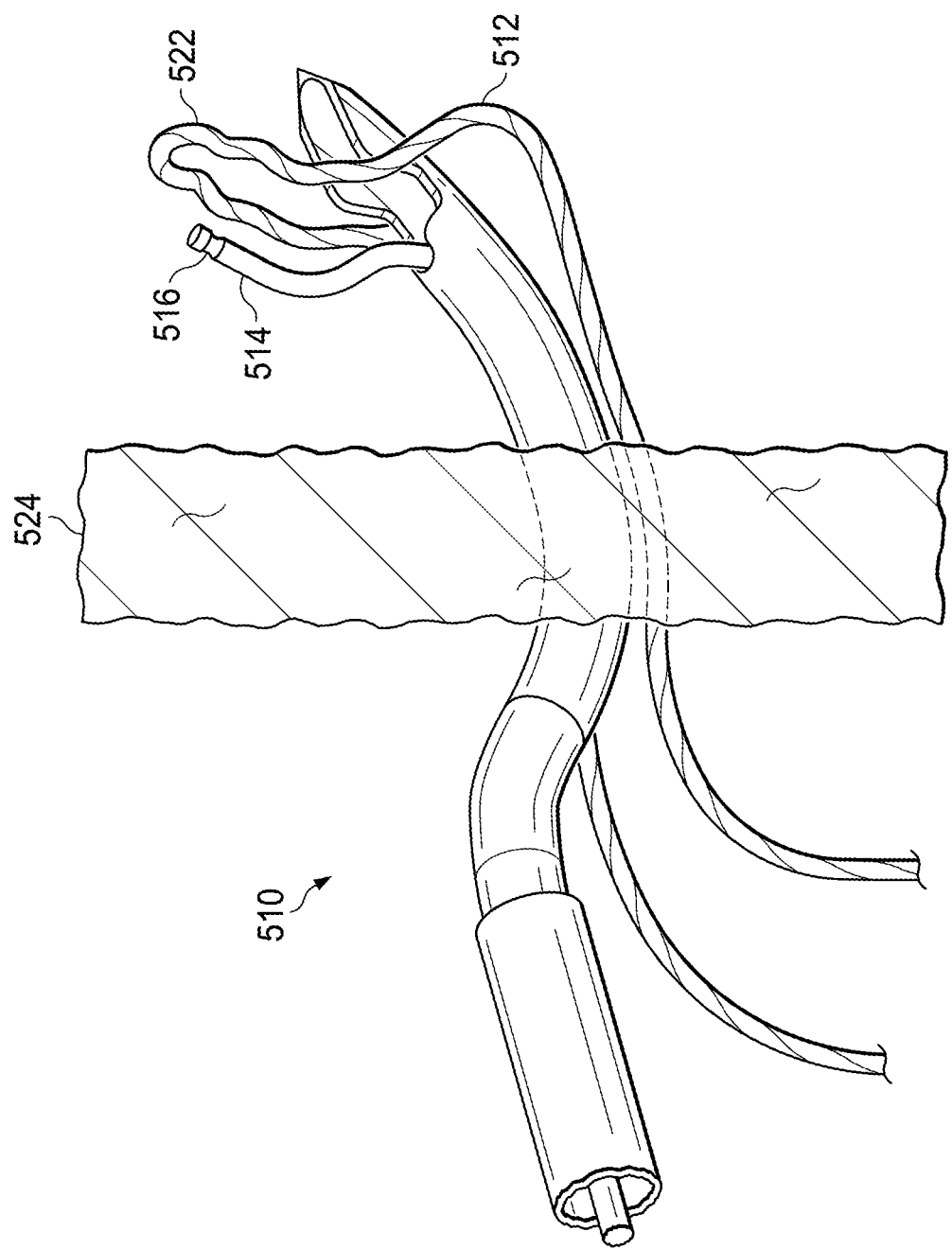
FIG. 52 is an illustration of a surgical instrument manipulating passing suture through tissue.

FIG. 52 shows suture passer 510 penetrating through tissue 524 and carrying the suture 512. Once through the tissue, the inner member 514 (with the aid of the grasping ring 516) pushes the suture out of the inner lumen. A relatively large loop 522 is thereby created that can be easily retrieved by the surgeon.

The size of the loop created by the instrument may be selectively set during a procedure, or predetermined. For example, in embodiments, the handle may include a lever as described herein and have a lever path or slot in the handle for the lever to move. The lever may be coupled to the inner member such that the length of travel through the lumen during the retraction step coincides with the length of travel of the lever. The handle and lever may be marked to indicate the loop-size increments. Additionally, the handle, lever and inner member may include hard stops and a limited range of motion to prevent undesirable-sized loops. For example a lever path may be shaped to limit the length that the lever may travel (e.g. a 0.3 to 0.5 inch and in some embodiments about 0.4 inch long rectangular slot).

An exemplary range for the length of the large loops ($L_L$) described herein are 0.3 to 0.5 inches, and more preferably between about 0.4 inches.

Figure 53:
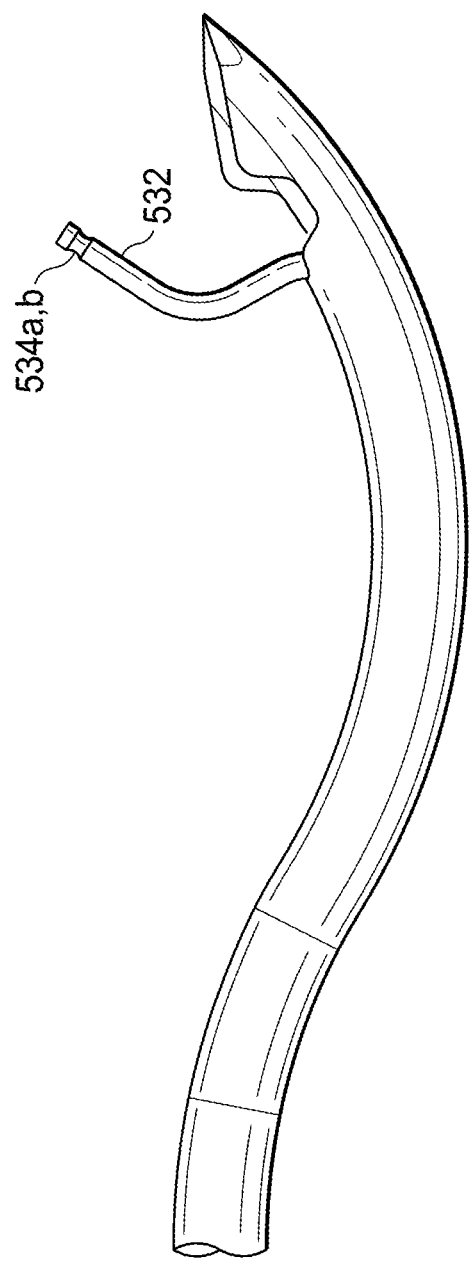
FIGS. 53-54 are side views of other needle distal sections and inner members in extended configurations.

The shape of the grasping or pushing feature may vary widely. FIG. 53, for example, shows a trough or detent 534 for catching and manipulating the suture in the proximal and distal direction. The protruding surfaces may be formed by two rings affixed to the shaft and spaced apart a small distance to form the trough.

Figure 54:
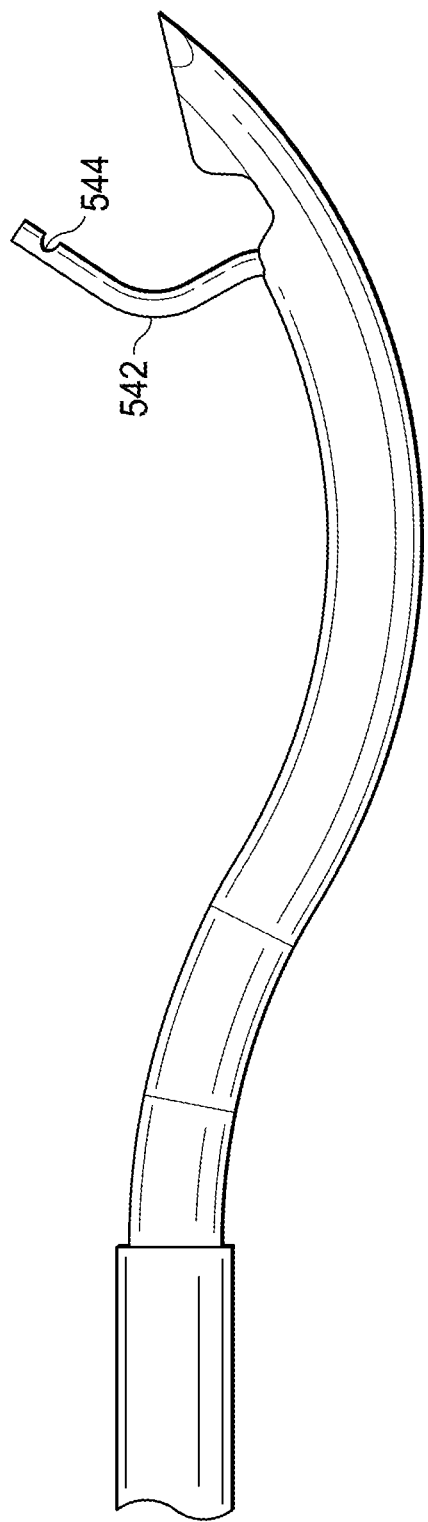

FIG. 54 shows a cut or notch 544. These features interact with, namely, grab, draw, and push the suture. Many variations of the grasping feature and means are intended to be included as part of the invention unless specifically excluded by the appended claims. For example, rings may extend partially around the circumference of the inner member. Protrusions, detents, cuts (e.g. a spiral cut), may be incorporated or formed into the distal end of the inner member. Additionally, the feature may comprise frictional means such as a surface roughening, asperity, burr, or frictional material which presents greater frictional force on the suture than on the wall of the inner lumen. Hence, when the inner member is moved, the suture follows.

FIG. 55 shows another structure adapted to grasp and draw the suture into the needle. In FIG. 55, the inner member comprises a dogleg distal section. The dogleg tip serves to assist in drawing the suture into the lumen during the retraction step of the procedure described above.

FIGS. 56a-56b are side and front views respectively of the inner member shown in FIG. 55. The inner member 552 is shown comprising an elongate section 554, terminating at a first bend 556. A non limiting exemplary range for the length of the elongate section 554 is between 8 and 9 inches. A non limiting exemplary range for the first angle of is between 70 and 85 degrees, and more preferably between 75 and 80 degrees. The dogleg is characterized by a lateral extending leg portion 558 and a second bend 560. An exemplary range for the length of the leg portion 558 is between 0.2 and 0.3 inches. The second bend angle may range from 80-90 degrees, and preferably from 85-89 degrees. The length of the tip segment 562 may range from 0.5 to 0.7 inches. Additionally, the diameter of the inner member may range from 0.015 to 0.025 inches.

FIG. 57 is a side view of another embodiment showing inner member 570 in an extended configuration. The inner member 570 comprises a crochet shaped distal section 572. The crochet tip serves to assist in drawing the suture into the lumen during the retraction step (as well as pushing the suture out of the lumen) during a procedure as described above.

FIGS. 58a-58b are side and front views respectively of the inner member 570 shown in FIG. 57. An elongate shaft extends to a first bend 571. A lateral segment extends from the first bend to second bend 573. A third bend 574 forms the crochet-shaped end portion. Many of the dimensions may be similar to that described above in connection with FIGS. 56a-56b except that the crochet tip extends and forms a smooth rounded semi circle. The semi circle shape is advantageous over a full circle hook because a full circle hook can have a tendency to fail to release the suture, and fail to smoothly fit within an arthroscopic needle.

A non-limiting exemplary inner radius 574 and outer radius 576 for the crochet tip is approximately 0.015 and 0.040 inches respectively. A non-limiting exemplary height 578 ranges from 0.2 to 0.3 inches.

Figure 59A:
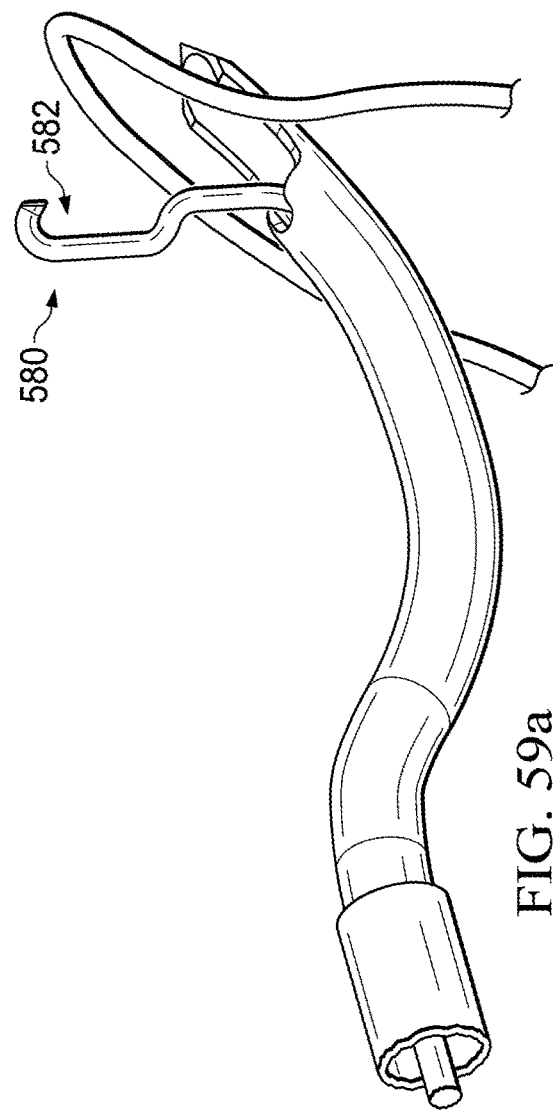
FIG. 59a is a side view of another needle distal section and inner member shown in an extended configuration.

FIG. 59a is a side view of the working end of another suture passing instrument showing inner member 580 in an extended configuration. The inner member comprises a box shaped distal section 582. The box shaped tip serves to assist drawing the suture into the lumen during the retraction step (as well as pushing the suture out of the lumen).

Figure 59B:
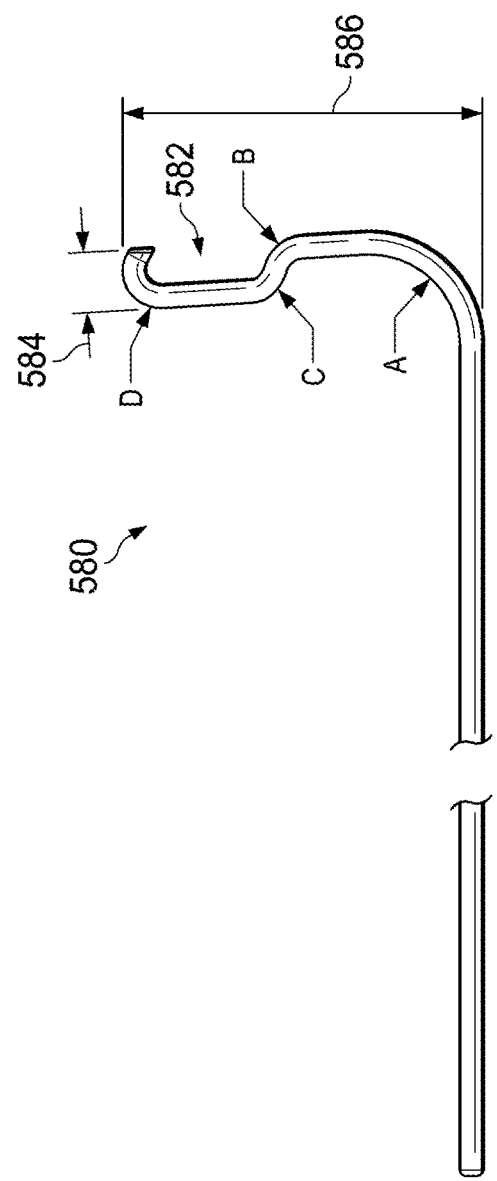

FIG. 59b is a side view of the inner member shown in FIG. 59a. An elongate shaft extends to a first bend (A). A lateral segment extends from the first bend to second bend (B). Second bend extends to a third bend (C). A base region forming the bottom of the box extends to fourth bend (D).

Many of the dimensions (e.g., shaft outer diameter [OD]) shown in FIGS. 59a-59b may be similar to that described above in connection with FIGS. 58a-58b except that the box shaped tip 582 comprises a pair of dog-legs or right angles to make a box-like shape instead of a rounded semi-circle or crochet end. A non-limiting exemplary depth 584 of box is approximately 0.04 to 0.06 inches respectively. A non-limiting exemplary height 586 ranges from 0.2 to 0.3 inches.

FIGS. 60a-60b are side and front views respectively of the working end of another embodiment showing inner member 594 shown in a deployed or extended configuration. The inner member 594 comprises an open trapezoidal-shaped (or parallelogram-shaped) suture grasping cavity 596. With reference to FIGS. 60c-60d, the grasping region may be defined by a pair of side walls separated by a width (W) and having a depth (D). The side walls are shown at different angles from one another. However, the side walls or portions of the side walls may be parallel or close to parallel with one another. Additionally, as shown, the shape or curvature of each of the side walls may vary and may be different from one another. For example, as shown, the distal most side wall has a greater curvature than the more proximal side wall. Similar to the crochet or box shaped grasping feature discussed above, the grasping space 596 serves to move the suture within the needle as will be described in more detail herein.

The inner member 594 shown in FIGS. 60a-60d may be made from a flat sheet. The inner member 594 is shown having a thickness ($t_1$) in the range from 0.01 to 0.03 inches, and more preferably about 0.02 inches. Its sides may be flat. The height (H) may range from 0.25 to 0.35 inches. Such an inner member may be machined to size, or otherwise formed by removing or cutting away material from a flat sheet. Exemplary materials include stainless steel, spring steel or Nitinol. No shape setting is required. The shapes may be cut using well know conventional machining techniques (such as EDM) or otherwise formed. Additionally, in certain embodiments, thin sheets may be stacked together and machined to shape as a batch.

The flat inner member 594 has varying stiffness along its length. The stiffness may be adjusted by varying the cross section, effective diameter or thickness of the member along its length. Preferably, in certain embodiments, the tip section 596 comprises a stiffness sufficient to grasp the suture whereas the elongate straight base sections are relatively more flexible to allow for these sections to elastically deform while advanced through the curves of the needle lumen in the distal section of the needle.

In certain embodiments the inner member's varying cross sectional size allows for only elastic deformation in certain portions of the inner member (e.g., proximal sections) while allowing other portions of the inner member (e.g., the distal tip) to be relatively stiff. In certain embodiments, the proximal section is narrower or thinner than the distal tip section. The distal tip section has a larger cross section than the proximal section in embodiments. Even when the distal section is placed under stress, it will not deform and can hold onto the suture.

In certain embodiments the inner member comprises a "flat wire" design, and has a larger distal cross section than the proximal section. However, the invention is not so limited and other cross sectional shapes may be employed.

Without being bound to theory, the inventors have found that the flat cross section can enable about two times or more the torsional stability of the inner member within the needle lumen than a round cross section while retaining substantially the same elastic deformation and flexibility of the inner member. By torsional stability, it is meant the ability to maneuver between obstacles such as suture and tissue without plastically deforming, buckling, or twisting. Additionally, the inventors have found that being able to vary the cross section of the inner member has enabled a three to four times greater functionality in suture retention.

In contemplated embodiments the cross section along the inner member varies. The cross section is relatively small along the proximal section. The smaller cross section allows for elastic deformation of the inner member as it is advanced through the needle lumen. The cross section of the inner member is larger towards the distal tip. The larger cross section at the distal tip provides enhanced stiffness to grab and pull the suture. In contrast, an inner wire having a uniform-sized cross section may be robust enough to sufficiently grasp a suture but is undesirably susceptible to plastic deformation due, to the influence of curves in the needle lumen. For example, if the entire cross section of the inner wire is enlarged such that the distal tip section is stiff and can adequately grab the suture limbs, the inner member is less likely to elastically deform and more likely to plastically deform due to the influence of the needle lumen. This effect is magnified in more tortuous versions of the needle tip such as the instruments shown in FIGS. 19 and 20.

If the entire cross section of the inner member is reduced such that the inner wire is highly flexible and can elastically deform as it advanced through the needle lumen, the distal tip section will lack the stiffness to grab the sutures and may ultimately plastically deform such that consistent suture grasping is difficult. For these reasons, a varying cross section is a preferred embodiment. However, the invention is only intended to be limited as recited in the appended claims, and in embodiments, the inner member wire has a cross section that is uniform along its length.

FIG. 60c also shows an atruamatic nose tip 596. Such a tip may be machined or otherwise formed on the tip of the hook. A pointed nose tip enables easier maneuvering of the instrument. A smooth pointed nose tip may serve to separate sutures extending from an anchor such that at least one of many suture tails may be selected and captured. A suture bundle may be more conveniently approached and separated with a nose tip as shown in FIG. 60c.

Figure 60E:
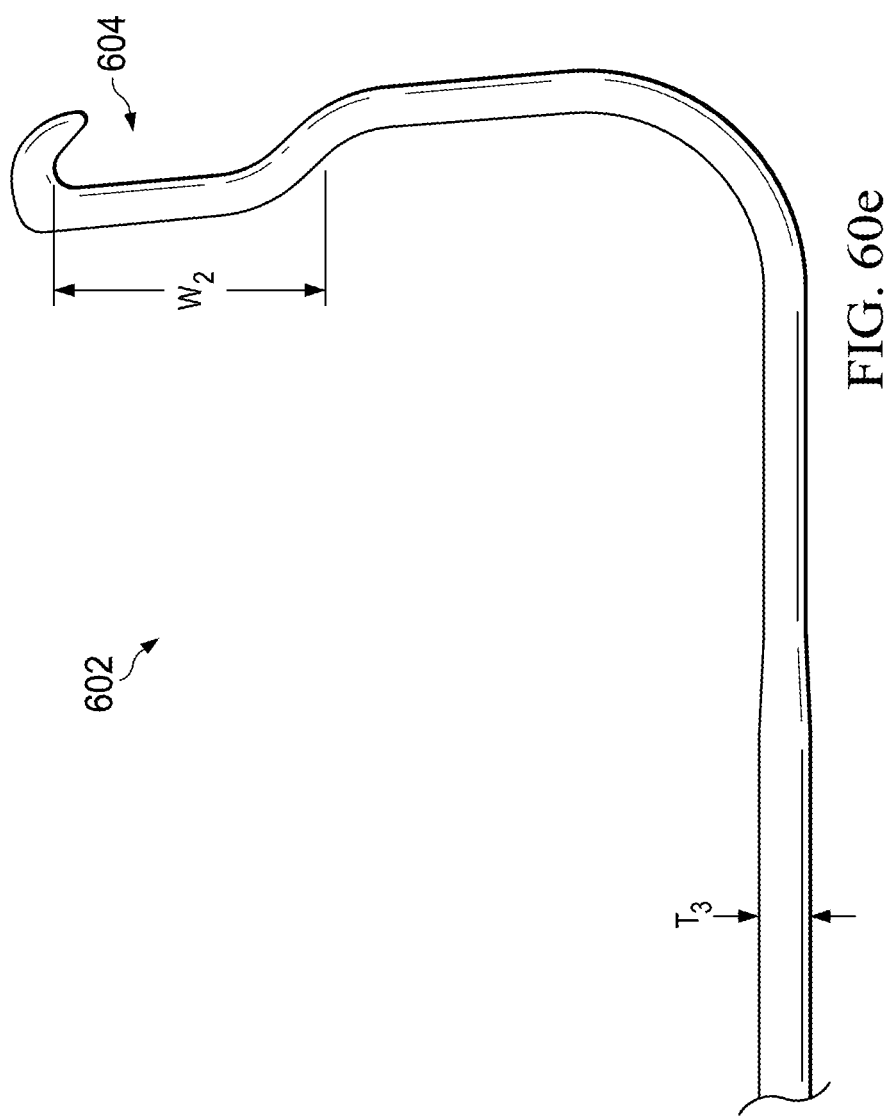
FIG. 60e is a side view of another inner member having an elongate distal section.

FIG. 60e shows a side view of another flat inner member 602 comprising an elongate box-shaped hook 604. In particular, the length of the base portion $W_2$ ranges from 0.02 to 0.12 inches. Additionally, the proximal section of the wire has thickness ($t_3$) of 0.015 to 0.045 inches (and in one embodiment $t_3$ is about 0.02 inches). Thickness ($t_3$) tapers to a smaller dimension towards the distal portion and is limited by the ID of the needle. In embodiments, the thickness ($t_3$) is such that the inner member fits snuggly in the ID of the needle.

Figure 60F:
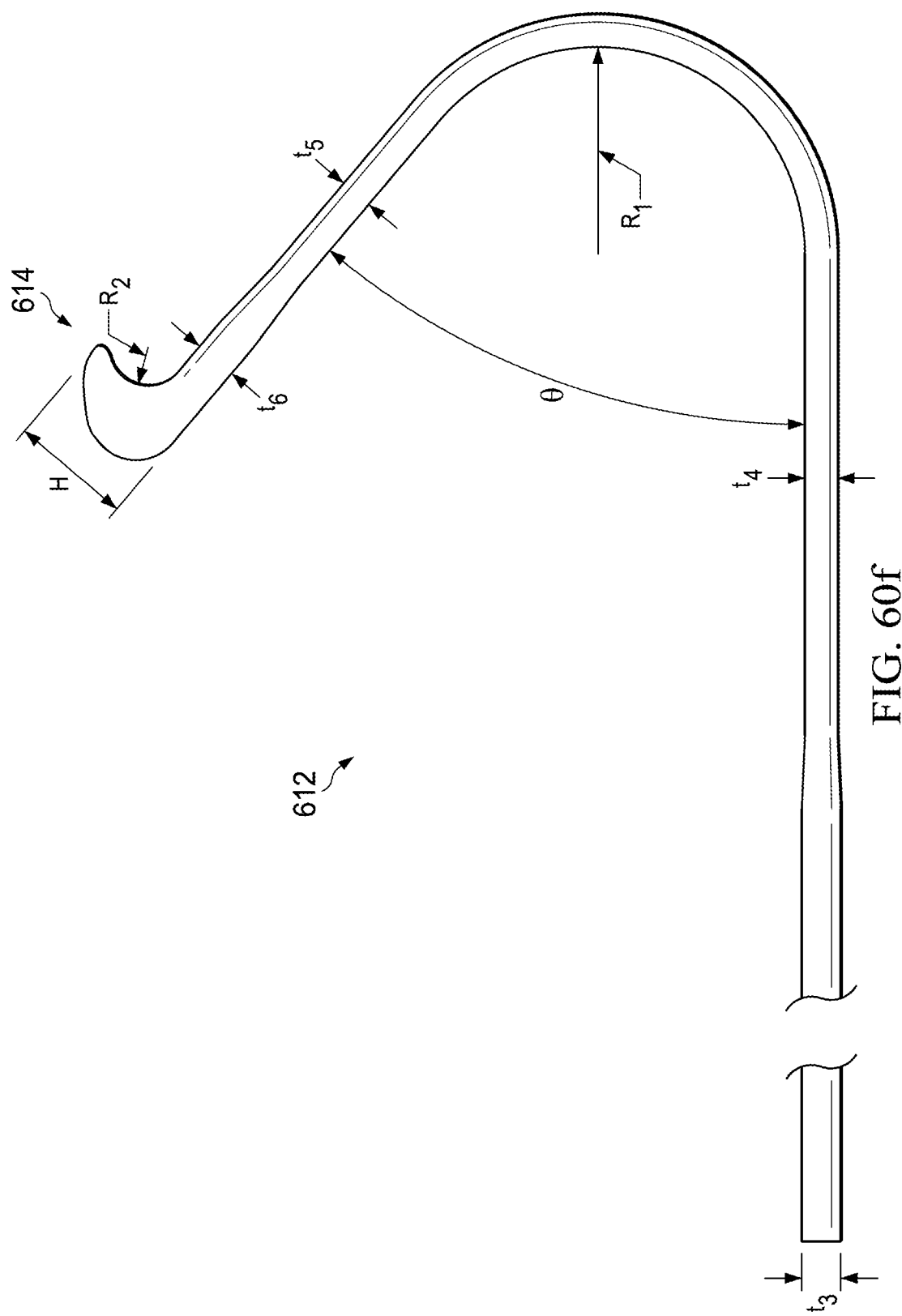
FIG. 60f is a side view of another inner member having a dog leg shaped distal section.

FIG. 60f shows a side view of another flat inner member 612 comprising an elongate dog leg-shaped hook 614. The length of the hook portion H ranges from 0.02 to 0.12 inches, and preferably is about 0.04-0.05 inches. Radius 1 ($R_1$) is about 0.08 inches (consequently forming an angle (theta) ranging from about 45-90 degrees, and more preferably between about 45-60 degrees. Radius 2 ($R_2$) is about 0.01-0.02 inches. Additionally, the proximal section of the wire has thickness ($t_3$) of 0.005 to 0.045 inches (and in one embodiment $t_3$ is about 0.02 inches). Thickness ($t_3$) tapers to a smaller dimension ($t_4$) towards the distal portion and is limited by the ID of the needle. In certain embodiments, the thickness ($t_3$) is such that the inner member fits snuggly in the ID of the needle. In the structure shown in FIG. 60f, ($t_4$) is about 0.05-0.2 inches. Thickness ($t_5$) is about the same as ($t_4$). Thickness ($t_6$) is shown being larger than ($t_5$) and in embodiments, ranges from 0.005-0.2 inches. As mentioned herein, the dimensions (e.g., angles, lengths, and thickness') of the embodiments may vary and be interchangeable with the dimensions of another embodiment except where such dimensions or features are mutually exclusive.

Figure 61A:
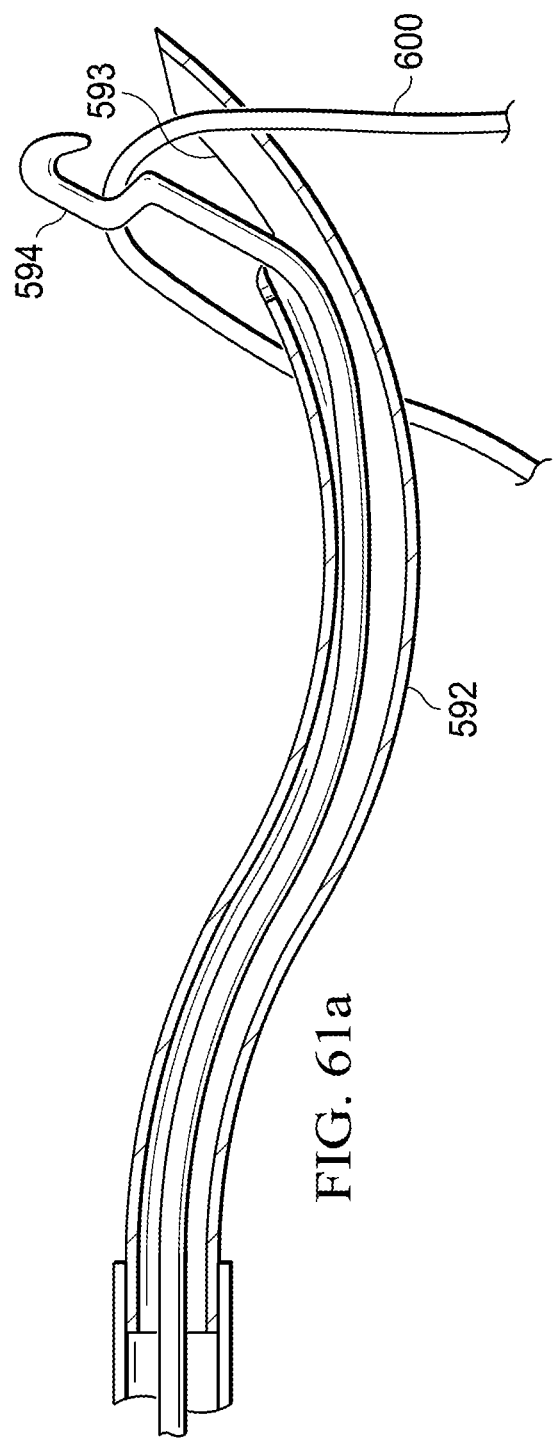
FIGS. 61a-61c are cross sectional views of the needle distal section and inner member shown in FIGS. 59a-59b, cooperating together to grab and draw a suture into the lumen of the needle.
Figure 61B:
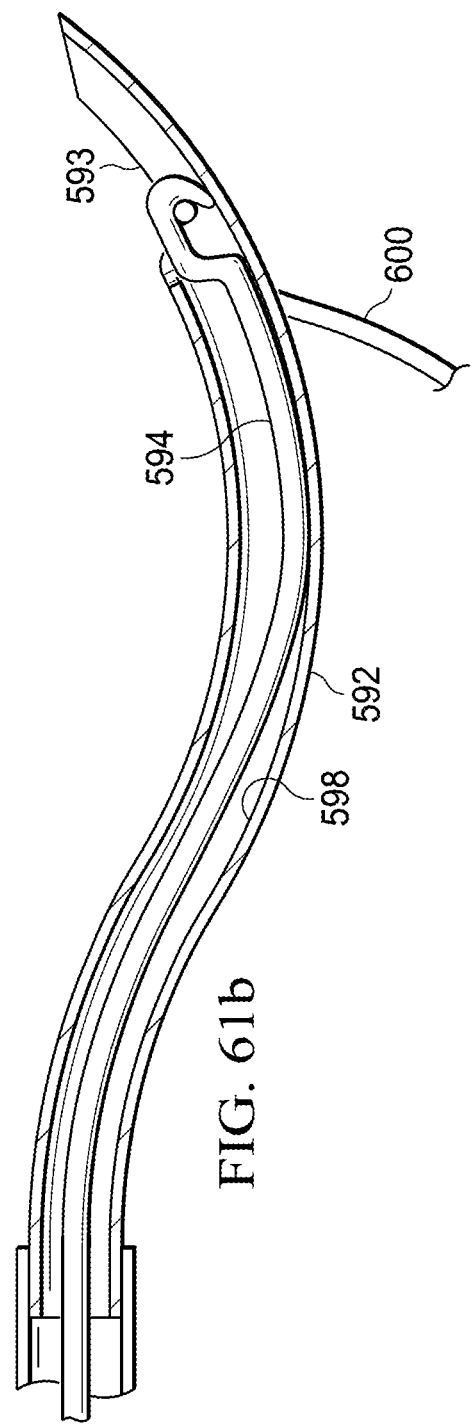
Figure 61C:
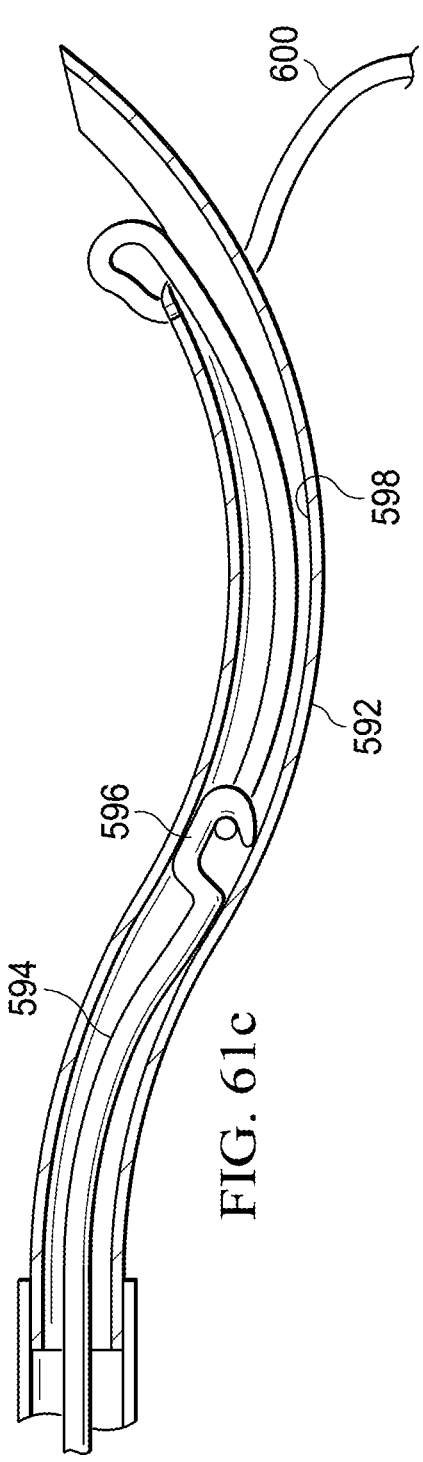

FIGS. 61a-61c are cross sectional views of the needle distal section 592 and inner wire member 594 shown in FIGS. 60a-60b, cooperating together to grab and draw a suture 600 into the needle lumen 598. The inner member 594 has been extended, creating a suture capture zone. The instrument is manipulated such that the suture 600 is positioned between the needle slot 593 and the inner member 594.

FIG. 61b is a cross sectional view of the needle distal section 592 shown in a suture grasping configuration. The inner member 594 is shown pinching the suture 600 to hold it in the suture slot 593.

FIG. 61c is a cross sectional view of the needle distal section 592 shown in a further retracted configuration. In particular, inner member 594 has been pulled proximally into the inner lumen 598, dragging the suture 600 into the inner lumen with the aid of the grasping feature 596.

A suture loop may be formed which is approximately equal to the length of suture pulled into the inner lumen 598. This relatively large loop is advantageous in arthroscopic surgery because it may be more easily grabbed by a surgeon than a smaller loop.

In embodiments of the invention, a method comprises the following steps: a) grasping the suture, b) drawing the suture into the lumen, and c) ejecting the suture from the instrument. Without being bound to theory, suture grasping and drawing forces may be compared to a suture pull out force. By pull out force, it is meant a maximum force applied to the suture until the suture is pulled out from the target material or instrument.

The drawing/grasping forces of various suture instruments were measured. In particular, various instruments as described herein were fabricated and manipulated to grab one suture tail, two suture tails and the pull out force was measured. Additionally, as the wire inner member was advanced through the needle lumen, a qualitative evaluation of the suture ejection was recorded ("1" being worst, not able to eject the suture, and "3" being best, full suture ejection and release).

Results are shown in the below table.

TABLE 1

| Description | One tail Pull out (grasping force, pounds) | Two tail Pull out (grasping force, pounds) | Suture Ejection (1-3, 3 being best) | Comments |
| --- | --- | --- | --- | --- |
| Nitinol Wire, One Ring | 2.8 | 2.8 | 3 | Relatively low pullout force. Highly navigable through needle lumen without plastic deformation. |
| Dogleg, Wire Nitinol | 4.5 | 6 | 2 | Relatively medium pullout force and suture ejection. |
| Crochet, Wire Nitinol | 4 | 5 | 3 | Highly navigable through needle lumen without plastic deformation. Medium pullout strength. |
| Trapezoid, Flat Nitinol | 12 | 22 | 3 | Highly navigable through needle lumen without plastic deformation, and excellent pull out force. |
| Full circle "Sheppard" hook, variable diameter | 0 | 7 | 1 | Spools single suture. Not able to eject suture from hook. |

Except for the full circle (or Sheppard's hook) design, the structures described above in the table operated to effectively navigate through an arthroscopic needle without any plastic deformation, grasp and pull the suture into the lumen with the forces listed above, and subsequently eject the suture from the needle to varying degrees of success.

The flat Nitinol wire with a trapezoid-shaped distal tip section showed a marked increase in suture pull out strength without any sacrifice in the ability to eject a suture, or suffer from plastic deformation. This data supports a conclusion that embodiments described herein (a) provide desirable suture pull out strength, (b) are easily navigable through the needle lumen without plastically deforming, and (c) predictably eject or release the suture from the instrument.

In embodiments, the described inner wires advantageously display a combination of stiffness at one region for firmly grasping the suture tail, but also a flexibility at other regions so as to avoid plastic deformation.

Without being bound to theory, embodiments of the invention described herein provide excellent suture pull out strength and suture ejection because of a combination of unique characteristics including but not limited to the cross sectional shape of the inner wire, the variation in cross section along its length, the number of bends along its length, the angle of the bends, and the shape of the suture capture zone.

Figure 62:
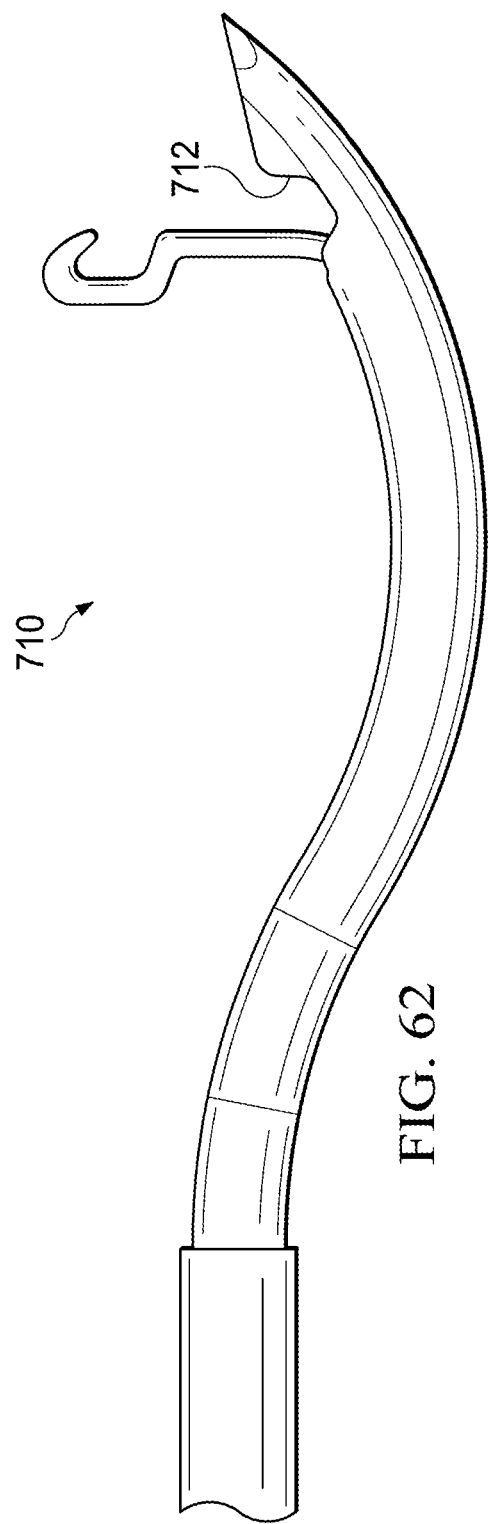
FIG. 62 is a side view of another needle distal section and inner wire member in an extended configuration.

Other modifications and variations can be made to the disclosed embodiments without departing from the subject invention. For example, FIG. 62 shows a side view of another needle distal section 710 and inner wire member combined in an extended configuration. The needle distal section 712 differs from the embodiment shown in FIGS. 61a-61c in that the slot profile is different. In particular, the needle wall shown in FIG. 62 includes a discrete cut out or recess whereas the slot profile shown in FIGS. 61a-61c has a shoulder or step design. Indeed, there are numerous potential shapes and features for the components of the invention, and numerous combinations of inner members and needle shapes, all of which are intended to be part of the invention except where excluded by the appended claims.

Additionally, other methods for suture manipulation and tissue repair will be apparent to the skilled artisan. Moreover, the instruments and methods described herein may be utilized in other regions of the body (e.g., knee, hip, etc.) and for other tissue treatment procedures. Thus, while the exemplary embodiments have been described in detail, by way of example and for clarity of understanding, a variety of changes, adaptations, and modifications will be obvious to those of skill in the art. Therefore, the scope of the present invention is limited solely by the appended claims.

What is claimed is:

1. An instrument for manipulating and passing suture through a tissue, said instrument comprising:
a handle end and a needle extending distally therefrom, the needle having a lumen extending therethrough, a distal tip, and an opening in communication with said lumen and the distal tip; and
an inner member movably disposed within said lumen, said inner member including a hook defined by a plurality of discrete bends and wherein the inner member is movable from a first retracted configuration in which at least a portion of the hook is situated within the lumen, and an extended configuration in which the hook extends from the opening; and wherein a distal section of the inner member has a preformed shape which directs the hook laterally away from a needle axis as the inner member moves towards the extended configuration, said needle axis extending through the needle towards the needle distal tip; and wherein the inner member distal section defines a first length having a first stiffness along a first bend and a second length extending from the first length and including the hook having a second stiffness, greater than the first stiffness distal to the first length; the first length configured so that the first bend may elastically deform while moving between the first retracted configuration and the extended configuration, and the second length, configured so that the hook resists deformation so as to maintain hold of the suture while manipulating the suture; and wherein the distal section of the inner member and the needle are configured to cooperate together to: (a) engage a suture disposed therebetween when the inner member is in the first retracted configuration, and (b) urge the clamped suture away from the suture instrument when the inner member is moved towards the extended configuration.

2. The instrument of claim 1 wherein the first length has a first cross sectional area and the second length has a second cross sectional area, and the first cross sectional area is smaller than the second cross sectional area.

3. The instrument of claim 1 wherein the hook of the inner member has a shape selected from the group consisting of a crochet hook, crescent curve, dogleg curve, and box hook.

4. The instrument of claim 1 wherein the distal section of the inner member and the needle are configured to cooperate together to engage a suture disposed therebetween when the inner member is in the first retracted configuration such that the suture is slideably encircled.

5. The instrument of claim 1 wherein the distal section of the inner member and the needle are configured to cooperate together to engage a suture disposed therebetween when the inner member is in the first retracted configuration such that the suture is pinned.

6. The instrument of claim 1 wherein the distal section of the inner member and the needle cooperate together to further draw the suture into the lumen so as to be proximally spaced from the entire opening subsequent to the engaging.

7. The instrument of claim 1 wherein the hook of the inner member is defined by three discrete curves defining a trapezoidal shaped cavity.

8. The instrument of claim 7 wherein a tip of the hook and a proximal-most curve of the three discrete curves both engage an inner surface of the needle lumen when in the first retracted configuration so as to enclose the trapezoidal shaped cavity with a length of the needle inner surface.

9. The instrument of claim 7 wherein a first and a second of the three discrete curves define a depth of the hook, the depth extending across a diameter of the needle lumen.

10. The instrument of claim 7 wherein the distal-most curve of the three discrete curves aims a tip of the hook proximally.

11. A suture instrument for manipulating and passing suture through a tissue, said instrument comprising:

a handle and a needle extending distally therefrom;
the needle end defining a lumen extending therethrough, a distal tip, and a laterally disposed opening along the needle end and in communication with said lumen; and
an inner member movably disposed within said lumen of said needle, between a first retracted configuration in which at least a portion of a distal section of the inner member is situated within the opening of the needle, a second retracted configuration in which a distal-most tip of the inner member is axially spaced away from the opening, and an extended configuration in which the distal section of the inner member extends from the opening of the needle; and wherein the distal section of the inner member has an engineered shape comprising a first curve which guides a hook of the inner member laterally away from a needle axis as the inner member moves towards the extended configuration, said axis extending through the needle towards the distal tip of the needle; wherein the hook is defined by a plurality of discrete curves and wherein the inner member first curve has a first stiffness, and the hook has a second stiffness, greater than the first stiffness so as to resist deformation of the hook portion during suture manipulation.

12. The suture instrument of claim 11 wherein the hook and the needle are configured to cooperate together to clamp a suture disposed therebetween when the inner member is in the first retracted configuration, and to eject the suture from the opening when the inner member is in the extended configuration.

13. The suture instrument of claim 11 further comprising a lever movably disposed in said handle and linked to the inner member to manipulate the inner member between the first retracted configuration, the second retracted configuration and the extended configuration.

14. The suture instrument of claim 11 wherein the distally disposed hook defines a trapezoidal shaped suture grasping cavity, defining a single opening that is covered by the lumen in the retracted configuration and thereby defining a trapezoidal shaped suture grasping cavity having a boundary including both the hook and lumen.

15. The instrument of claim 11 wherein the engineered shape is elastically deformed while disposed within the needle and reverts towards the engineered shape as the first curve extends from the opening, guiding the inner member laterally away from the needle as the inner member moves towards the extended configuration.

* * * * *